United States Patent
Daanen et al.

(10) Patent No.: US 9,682,985 B2
(45) Date of Patent: Jun. 20, 2017

(54) (INDAZOL-4-YL) HEXAHYDROPYRROLOPYRROLONES AND METHODS OF USE

(71) Applicant: AbbVie Inc., North Chicago, IL (US)

(72) Inventors: Jerome Daanen, Racine, WI (US); David DeGoey, Salem, WI (US); Jennifer M. Frost, Gurnee, IL (US); Tammie Jinkerson, Herington, KS (US); Steve Latshaw, Elijay, GA (US); Lei Shi, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/069,195

(22) Filed: Mar. 14, 2016

(65) Prior Publication Data

US 2016/0264582 A1    Sep. 15, 2016

Related U.S. Application Data

(60) Provisional application No. 62/132,953, filed on Mar. 13, 2015.

(51) Int. Cl.
  *C07D 487/04* (2006.01)
(52) U.S. Cl.
  CPC ................... *C07D 487/04* (2013.01)
(58) Field of Classification Search
  CPC .................................. C07D 487/04
  USPC ......................................... 514/338
  See application file for complete search history.

(56) References Cited

U.S. PATENT DOCUMENTS

2016/0075692 A1*  3/2016  Daanen ............... C07D 403/14
                                                       514/210.21

* cited by examiner

*Primary Examiner* — Yong Chu
(74) *Attorney, Agent, or Firm* — Michael J. Ward

(57) ABSTRACT

Compounds of formula (I)

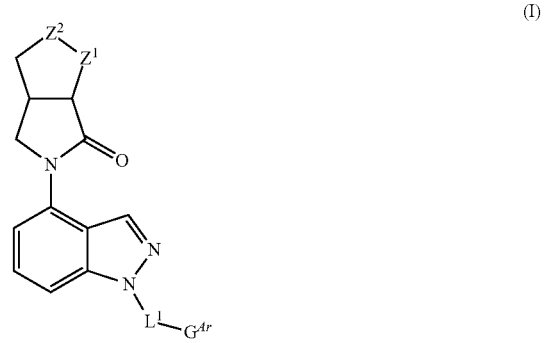

(I)

and pharmaceutically acceptable salts, esters, amides, or radiolabelled forms thereof, wherein $G^{Ar}$, $L^1$, $Z^1$ and $Z^2$ are as defined in the specification, are useful in treating conditions or disorders prevented by or ameliorated by voltage-gated sodium channels, e.g., $Na_v1.7$ and/or $Na_v1.8$. Methods for making the compounds are disclosed. Also disclosed are pharmaceutical compositions of compounds of formula (I), and methods for using such compounds and compositions.

19 Claims, No Drawings

(INDAZOL-4-YL) HEXAHYDROPYRROLOPYRROLONES AND METHODS OF USE

RELATED APPLICATION

This application claims the benefit of U.S. Provisional Application No. 62/132,953, filed Mar. 13, 2015. The contents of which are incorporated herein by reference.

BACKGROUND OF THE INVENTION

Technical Field

The invention relates to (indazol-4-yl)hexahydropyrrolopyrrolones that are sodium channel (e.g., $Na_v1.7$ and $Na_v1.8$) blockers, useful in treating diseases and conditions mediated and modulated by the voltage-gated sodium channels. Additionally, the invention relates to compositions containing compounds of the invention and processes of their preparation.

Description of Related Technology

The voltage-gated sodium channels (VGSCs, $Na_v1.x$) contribute to the initiation and propagation of action potentials in excitable tissues such as nerve and muscle by modulating the influx of sodium ions. $Na_v1.7$, one of nine sodium channel isoforms, is preferentially expressed in the peripheral nervous system where it acts as a threshold channel for action potential firing in neurons (Cummins T R, et al. Expert Rev Neurother 2007; 7:1597-1612. Rush A M, et al. J Physiol 2007; 579:1-14.). A wealth of evidence connects abnormal activity of sodium channels in the peripheral nervous system to the pathophysiology of chronic pain (Goldin A L, et al. Neuron 2000; 28:365-368. Dib-Hajj S D, et al. Annu Rev Neurosci 2010; 33:325-347.). Polymorphisms in SCN9A, the gene that encodes $Na_v1.7$, cause human pain disorders arising from either gain-of-function or loss-of-function mutations of the channel. Clinically, VGSC blockers have proven useful in the management of pain, but their utility is often limited by incomplete efficacy and poor tolerability. Local anesthetics (e.g., lidocaine), anti-arrhythmic agents (e.g., mexilitene), and anti-convulsants (e.g., lamotrigine) are all relatively weak ($IC_{50}$ values in the high micromolar range), non-selective (versus $Na_v1.x$ subtypes and other ion channels) VGSC blocking agents identified without prior knowledge of their molecular targets.

The VGSCs are integral plasma membrane proteins composed of a large (260 kDa) α-subunit and one or more smaller β-subunits (Hargus N J et al. Expert Opin Invest Drugs 2007; 16:635-646). Nine α-subunits ($Na_v1.1$-$Na_v1.9$) and four β-subunits (β1-β4) have been identified in mammals. The various VGSC subtypes exhibit diverse functional properties and distinct expression patterns, suggesting differential involvement in transmission of specific signals. $Na_v1.7$, $Na_v1.8$ and $Na_v1.9$ are expressed predominantly in the peripheral nervous system in humans and rodents (Waxman S G Brain 2010; 133:2515-2518). The biophysical characteristics of $Na_v1.7$ suggest a role in initiation of action potentials, while $Na_v1.8$ is a major contributor to the upstroke of action potentials in sensory neurons. $Na_v1.9$ produces a persistent current that is involved in setting the resting membrane potential.

The $Na_v1.7$ isoform is expressed in both small and large diameter dorsal root ganglion (DRG) neurons, as well as in sympathetic neurons, and in peripheral axonal termini of neurons processing pain. $Na_v1.7$ is up-regulated in preclinical models of inflammatory and neuropathic pain, including diabetic neuropathy (Dib-Hajj S D, et al. Nat Rev Neurosci. 2013; 14:49-62. Hong S, et al. Journal of Biological Chemistry. 2004; 279:29341-29350. Persson A K, et al. Exp Neurol. 2011; 230:273-279.). $Na_v1.7$ has been shown to accumulate in painful neuromas, such as those in amputees with phantom limb pain, and in painful dental pulp (Beneng K, et al. BMC Neurosci. 2010; 11:71. Dib-Hajj S D, et al. Nat Rev Neurosci. 2013; 14:49-62). Rare human genetic conditions involving single-nucleotide polymorphisms in SCN9A, the gene encoding for $Na_v1.7$ highlight its importance in pain pathways. Bi-allelic gain-of-function mutations (enhancing channel activity and increasing the excitability of DRG neurons) produce severe pain syndromes with dominant genetic inheritance. Mutations that hyperpolarize activation voltage dependence (i.e., facilitate channel opening and increase the excitability of DRG neurons) result in inherited erythromelalgia (IEM), a condition characterized by excruciating burning pain, attacks of edema, increased skin temperature and flushing of the skin affecting the distal extremities. Similarly, polymorphisms that impair inactivation of the channel and enhance persistent current lead to paroxysmal extreme pain disorder (PEPD), a condition wherein episodic severe perineal, perioccular and paramandibular pain is accompanied by autonomic manifestations such as skin flushing usually in the lower body (Waxman S G Nature 2011472:173-174. Dib-Hajj S D, et al. Brain 2005; 128:1847-1854.). By contrast, bi-allelic loss-of-function mutations preventing the production of functional $Na_v1.7$ channels produced channelopathy-associated congenital insensitivity to pain (CIP). CIP patients do not perceive or understand pain even when confronted with extreme pain stimuli such as bone fractures, surgery, dental extractions, burns, and childbirth.

The role of $Na_v1.7$ in pain has been confirmed in knockout studies. Global deletion of $Na_v1.7$ in knockout mice causes a disruption of normal eating behavior due to a deficit in olfaction, resulting in lethality shortly after birth (Nassar M A, et al. Proc Natl Acad Sci USA 2004; 101:12706-12711). A conditional $Na_v1.7$ knockout in $Na_v1.8$-expressing DRG neurons abrogated inflammation-induced pain and diminished responses to mechanical insult, but neuropathic pain development was not affected (Nassar M A, et al. Mol Pain 2005; 1:24-31). However, ablation of $Na_v1.7$ in both sensory and sympathetic neurons recapitulated the pain-free phenotype seen in CIP patients, abolishing inflammatory and neuropathic pain without causing any overt autonomic dysfunction (Minett M S, et al. Nat Commun 2012; 3:791). $Na_v1.7$-deficient sensory neurons also failed to release substance P in the spinal cord or to display synaptic potentiation in the dorsal horn of the spinal cord in response to electrical stimulation of the sciatic nerve (Minett M S, et al. Nat Commun 2012; 3:791).

The level of preclinical validation for the $Na_v1.8$ isoform as a target for pain is also compelling. Complementary to $Na_v1.7$ in its biophysical and functional profile, the $Na_v1.8$ isoform is expressed in nociceptive trigeminal neurons, in the vast majority of DRG neurons, and in peripheral free nerve endings (Shields S D, et al. Pain 2012; 32:10819-10832). An evaluation of $Na_v1.8$-null mice demonstrated that this channel carries the majority of current underlying the upstroke of the action potential in nociceptive neurons. Knockout studies further implicate $Na_v1.8$ in visceral, cold, and inflammatory pain, but not in neuropathic pain. However, assessment of $Na_v1.8$ antisense oligonucleotides, also suggested involvement of $Na_v1.8$ in the development and maintenance of neuropathic pain, in addition to confirming the relevance of the channel in inflammatory pain (Momin A, et al. Curr Opin Neurobiol 2008; 18:383-388. Rush A M, et al. J Physiol 2007; 579:1-14. Liu M et al. Pain Med 12 Suppl 2011; 3:593-99.). Human gain-of-function mutations in $Na_v1.8$ were recently identified in patients with small fiber neuropathy (SFN) who were all negative for mutations in $Na_v1.7$ (Faber C G, et al. Proc Natl Acad Sci USA. 2012; 109:19444-19449).

While the literature offers preclinical validation for $Na_v1.7$ and $Na_v1.8$ as pain targets, multiple challenges confront the discovery and development of small molecule blockers. The potency needed for efficacy, the levels of selectivity versus the various isoforms required for acceptable therapeutic index, and the relevance of state- and use-dependent activity are not well understood. For example, with respect to selectivity, the human ether-a-go-go-related gene (hERG, Kv11.1) is a potassium channel responsible for the rapidly activating repolarization current $I_{Kr}$ that has a critical role in cardiac electrophysiology and drug safety. hERG inhibition is the most common mechanism of drug-induced QT prolongation and torsades de pointes (TdP) arrhythmia. The study of hERG has become an important predictor of cardiac risk (Rampe, D, et al. Journal of Pharmacological and Toxicological Methods 2013; 68:13-22), and it is desirable to have selectivity for voltage-gated sodium channels over hERG.

Although compounds and mechanisms exist that are used clinically to treat pain, there is need for new compounds that can effectively treat different types of pain. Pain of various types (e.g., inflammatory pain, post-surgical pain, osteoarthritis pain, knee pain, lower back pain, neuropathic pain) afflicts virtually all humans and animals at one time or another, and a substantial number of medical disorders and conditions produce some sort of pain as a prominent concern requiring treatment. As such, it would be particularly beneficial to identify new compounds for treating the various types of pain.

SUMMARY

The invention is directed to (indazol-4-yl)hexahydropyrrolopyrrolones having a structure of formula (I):

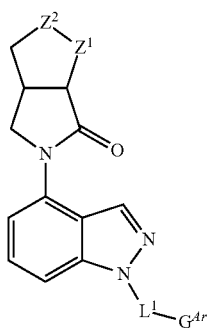

(I)

or a pharmaceutically acceptable salt or isotopically labelled form thereof, wherein:

one of $Z^1$ and $Z^2$ is $NR^1$ and the other of $Z^1$ and $Z^2$ is $CH_2$;
$R^1$ is selected from the group consisting of $-CH_2G^1$, $-CH_2G^2$, $-C(O)-G^1$, $-C(O)-G^2$, $-C(O)-R^2$, $-C(O)N(R^a)-R^2$, $-C(O)N(R^a)(R^b)$, $-SO_2-G^1$, $-SO_2-G^2$, $-SO_2-R^2$, $-SO_2N(R^a)-R^2$, and $-SO_2N(R^a)(R^b)$;

$R^2$ is selected from the group consisting of $C_1$-$C_6$-alkyl, $C_2$-$C_6$-alkenyl, $C_2$-$C_6$-alkynyl, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})$, $-(CR^{4a}R^{5a})_m-SR^{1a}$, $-(CR^{4a}R^{5a})_m-S(O)_2R^{2a}$, $-(CR^{4a}R^{5a})_m-S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)S(O)_2R^{2a}$, $-(CR^{4a}R^{5a})_m-N(R^a)C(O)O(R^{1a})$, $-(CR^{4a}R^{5a})_m-N(R^a)C(O)N(R^b)(R^{3a})$, $-(CR^{4a}R^{5a})_m-G^1$, $-(CR^{4a}R^{5a})_m-G^2$, cyano-$C_1$-$C_6$-alkyl, and halo-$C_1$-$C_6$-alkyl;

$R^a$ and $R^b$, at each occurrence, are each independently hydrogen, $C_1$-$C_6$-alkyl, or halo-$C_1$-$C_6$-alkyl;

$R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen;

$R^d$ at each occurrence, is independently $C_1$-$C_6$-alkyl or halo-$C_1$-$C_6$-alkyl;

$R^{1a}$ and $R^{3a}$, at each occurrence, are each independently hydrogen, $C_1$-$C_6$-alkyl, halo-$C_1$-$C_6$-alkyl, $-G^1$, or $-(CR^{4a}R^{5a})_n-G^1$;

$R^{2a}$, at each occurrence, is independently $C_1$-$C_6$-alkyl, halo-$C_1$-$C_6$-alkyl, $-G^1$, or $-(CR^{4a}R^{5a})_n-G^1$;

$R^{4a}$ and $R^{5a}$, at each occurrence, are each independently hydrogen, halogen, $C_1$-$C_6$-alkyl, or halo-$C_1$-$C_6$-alkyl;

$G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen;

$G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, $-N(R^c)_2$, $-N(R^c)C(O)R^c$, $-C(O)R^c$, $-C(O)OR^c$, $-C(O)N(R^c)_2$, $-SO_2R^a$, $-SO_2N(R^c)_2$, and $-CH_2G^3$;

$G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, $-N(R^c)_2$, $-N(R^c)C(O)R^c$, $-C(O)R^c$, $-C(O)OR^c$, $-C(O)N(R^c)_2$, $-SO_2R^a$, and $-SO_2N(R^c)_2$;

$G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, $-NO_2$, $-OR^{1a}$, $-OC(O)R^{1a}$, $-OC(O)N(R^b)(R^{3a})$, $-SR^{1a}$, $-S(O)_2R^{2a}$, $-S(O)_2N(R^b)(R^{3a})$, $-C(O)R^{1a}$, $-C(O)OR^{1a}$, $-C(O)N(R^b)(R^{3a})$, $-N(R^b)(R^{3a})$, $-N(R^a)C(O)R^{1a}$, $-N(R^a)S(O)_2R^{2a}$, $-N(R^a)C(O)O(R^{1a})$, $-N(R^a)C(O)N(R^b)(R^{3a})$, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})$, $-(CR^{4a}R^{5a})_m-SR^{1a}$, $-(CR^{4a}R^{5a})_m-S(O)_2R^{2a}$, $-(CR^{4a}R^{5a})_m-S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)S(O)_2R^{2a}$, $-(CR^{4a}R^{5a})_m-N(R^a)C(O)O(R^{1a})$, $-(CR^{4a}R^{5a})_m-N(R^a)C(O)N(R^b)(R^{3a})$, cyano-$C_1$-$C_6$-alkyl, and halo-$C_1$-$C_6$-alkyl;

$L^1$ is a bond or $-CH_2-$; and m and n, at each occurrence, are each independently 1, 2, 3, 4, or 5.

Another aspect of the invention relates to pharmaceutical compositions comprising compounds of the invention. Such compositions can be administered in accordance with a method of the invention, typically as part of a therapeutic regimen for treatment or prevention of conditions and disorders related to voltage-gated sodium channel (and particularly $Na_v1.7$ and $Na_v1.8$) activity.

Yet another aspect of the invention relates to a method of selectively blocking voltage-gated sodium channels (e.g., $Na_v1.7$ and $Na_v1.8$ channels). The method is useful for treating, or preventing conditions and disorders related to blocking voltage-gated sodium channels in mammals. More particularly, the method is useful for treating or preventing conditions and disorders related to pain, neuropathy, inflammation, auto-immune disease, fibrosis, chronic kidney disease, and cancer. Accordingly, the compounds and compositions of the invention are useful as a medicament for treating or preventing voltage-gated sodium channel modulated disease.

The compounds, compositions comprising the compounds, methods for making the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

Compounds of formula (I) are disclosed in this invention

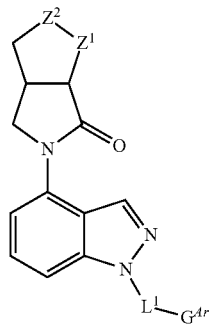

(I)

wherein $L^1$, $G^{Ar}$, $Z^1$ and $Z^2$ are as defined above in the Summary. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

DEFINITION OF TERMS

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon containing from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 1-phenylethyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo [3.1.1]heptane, bicyclo[2.2.1]heptane, bicyclo[2.2.2]octane, bicyclo[3.2.2]nonane, bicyclo[3.3.1]nonane, and bicyclo [4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1. $0^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

The term "cycloalkylalkyl" as used herein, means a cycloalkyl group appended to the parent molecular moiety through an alkyl group, as defined herein.

The term "halo" or "halogen" as used herein, means Cl, Br, I, or F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo [1,2-a]pyridinyl, indazolyl, indolyl, isoindolyl, isoquinolinyl, naphthyridinyl, pyridoimidazolyl, quinolinyl, thiazolo [5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heterocycle" or "heterocyclic" as used herein, means a monocyclic heterocycle, a bicyclic heterocycle, a tricyclic heterocycle, or a spirocyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1] heptyl (including 2-azabicyclo[2.2.1]hept-2-yl), 2,3- dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heteroatom" as used herein, means a nitrogen, oxygen, or sulfur atom.

The term "nitro" as used herein means a —NO$_2$ group.

The term "oxo" as used herein means (═O).

In some instances, the number of carbon atoms in a hydrocarbyl substituent (e.g., alkyl, alkenyl, alkynyl, or cycloalkyl) is indicated by the prefix "C$_x$-C$_y$-", wherein x is the minimum number and y is the maximum number of carbon atoms in the substituent. Thus, for example, "C$_1$-C$_6$-alkyl" refers to an alkyl substituent containing from 1 to 6 carbon atoms. Illustrating further, C$_3$-C$_6$-cycloalkyl means a saturated hydrocarbyl ring containing from 3 to 6 carbon ring atoms.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

Compounds of the Invention

Compounds of the invention can have the formula (I) as described in the Summary.

Particular values of variable groups in compounds of formula (I) are as follows. Such values can be used where appropriate with any of the other values, definitions, claims or embodiments defined hereinbefore or hereinafter.

In one embodiment, one of $Z^1$ and $Z^2$ is NR$^1$ and the other of $Z^1$ and $Z^2$ is CH$_2$, wherein R$^1$ is as defined in the Summary.

In an embodiment, $Z^1$ is NR$^1$ and $Z^2$ is CH$_2$, wherein R$^1$ is as defined in the Summary.

In an embodiment, $Z^1$ is CH$_2$ and $Z^2$ is NR$^1$, wherein R$^1$ is as defined in the Summary.

In one embodiment, R$^1$ is selected from the group consisting of —CH$_2$G$^1$, —CH$_2$G$^2$, —C(O)-G$^1$, —C(O)-G$^2$, —C(O)—R$^2$, —C(O)N(R$^a$)—R$^2$, —C(O)N(R$^a$)(R$^b$), —SO$_2$-G$^1$, —SO$_2$-G$^2$, —SO$_2$—R$^2$, —SO$_2$N(R$^a$)—R$^2$, and —SO$_2$N(R$^a$)(R$^b$), wherein G$^1$, G$^2$, R$^a$, R$^b$, and R$^2$ are as defined in the Summary.

In an embodiment, R$^1$ is selected from the group consisting of —CH$_2$G$^1$, —C(O)-G$^1$, —C(O)-G$^2$, —C(O)—R$^2$, —C(O)N(R$^a$)—R$^2$, —C(O)N(R$^a$)(R$^b$), —SO$_2$-G$^1$, —SO$_2$-G$^2$, and —SO$_2$—R$^2$, wherein G$^1$, G$^2$, R$^a$, R$^b$, and R$^2$ are as defined in the Summary.

In an embodiment, R$^1$ is selected from the group consisting of —CH$_2$G$^1$, wherein G$^1$ is as defined in the Summary.

In an embodiment, R$^1$ is selected from the group consisting of —C(O)-G$^1$, —C(O)-G$^2$, —C(O)—R$^2$, —C(O)N(R$^a$)—R$^2$, and —C(O)N(R$^a$)(R$^b$), wherein G$^1$, G$^2$, R$^a$, R$^b$, and R$^2$ are as defined in the Summary.

In an embodiment, R$^1$ is selected from the group consisting of —SO$_2$-G$^1$, —SO$_2$-G$^2$, and —SO$_2$—R$^2$, wherein G$^1$, G$^2$ and R$^2$ are as defined in the Summary.

In one embodiment, R$^2$ is selected from the group consisting of C$_1$-C$_6$-alkyl, C$_2$-C$_6$-alkenyl, C$_2$-C$_6$-alkynyl, —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)S(O)$_2$R$^{2a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^1$, —(CR$^{4a}$R$^{5a}$)$_m$-G$^2$, cyano-C$_1$-C$_6$-alkyl, and halo-C$_1$-C$_6$-alkyl, wherein G$^1$, G$^2$, R$^a$, R$^b$, R$^{1a}$, R$^{2a}$, R$^{3a}$, R$^{4a}$, R$^{5a}$, and m are as defined in the Summary.

In an embodiment, R$^2$ is selected from the group consisting of C$_1$-C$_6$-alkyl, —(CR$^{4a}$R$^{5a}$)$_m$—OR$^{1a}$, —(CR$^{4a}$R$^{5a}$)$_m$—C(O)N(R$^b$)(R$^{3a}$), —(CR$^{4a}$R$^{5a}$)$_m$-G$^1$, —(CR$^{4a}$R$^{5a}$)$_m$-G$^2$, and halo-C$_1$-C$_6$-alkyl, wherein G$^1$, G$^2$, R$^b$, R$^{1a}$R$^{3a}$, R$^{4a}$, R$^{5a}$, and m are as defined in the Summary.

In an embodiment, R$^a$, at each occurrence, is independently hydrogen, C$_1$-C$_6$-alkyl, or halo-C$_1$-C$_6$-alkyl.

In one embodiment, R$^a$, at each occurrence, is independently hydrogen or C$_1$-C$_6$-alkyl.

In one embodiment, R$^a$, at each occurrence, is independently hydrogen.

In one embodiment, R$^a$, at each occurrence, is independently C$_1$-C$_6$-alkyl.

In an embodiment, R$^b$, at each occurrence, is independently hydrogen, C$_1$-C$_6$-alkyl, or halo-C$_1$-C$_6$-alkyl.

In one embodiment, R$^b$, at each occurrence, is independently hydrogen or C$_1$-C$_6$-alkyl.

In one embodiment, R$^b$, at each occurrence, is independently hydrogen.

In one embodiment, R$^b$, at each occurrence, is independently C$_1$-C$_6$-alkyl.

In an embodiment, R$^c$ at each occurrence, is independently hydrogen, C$_1$-C$_6$-alkyl, aryl, aryl-C$_1$-C$_6$-alkyl, cycloalkyl, cycloalkyl-C$_1$-C$_6$-alkyl, or halo-C$_1$-C$_6$-alkyl; wherein said aryl, the aryl of aryl-C$_1$-C$_6$-alkyl, the cycloalkyl, and the cycloalkyl of cycloalkyl-C$_1$-C$_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen.

In one embodiment, $R^c$ at each occurrence, is independently hydrogen or $C_1$-$C_6$-alkyl.

In one embodiment, $R^c$ at each occurrence, is hydrogen.

In one embodiment, $R^c$ at each occurrence, is $C_1$-$C_6$-alkyl.

In an embodiment, $R^d$ at each occurrence, is independently $C_1$-$C_6$-alkyl or halo-$C_1$-$C_6$-alkyl.

In one embodiment, $R^d$ is $C_1$-$C_6$-alkyl.

In one embodiment, $R^d$ is halo-$C_1$-$C_6$-alkyl.

In an embodiment, $R^{1a}$, at each occurrence, is independently hydrogen, $C_1$-$C_6$-alkyl, halo-$C_1$-$C_6$-alkyl, -$G^1$, or —$(CR^{4a}R^{5a})_m$-$G^1$, wherein $G^1$, $R^{4a}$, $R^{5a}$ and n are as defined in the Summary.

In one embodiment, $R^{1a}$, at each occurrence, is hydrogen.

In an embodiment, $R^{3a}$, at each occurrence, is independently hydrogen, $C_1$-$C_6$-alkyl, halo-$C_1$-$C_6$-alkyl, -$G^1$, or —$(CR^{4a}R^{5a})_m$-$G^1$, wherein $G^1$, $R^{4a}$, $R^{5a}$ and n are as defined in the Summary.

In one embodiment, $R^{3a}$, at each occurrence, is hydrogen.

In an embodiment, $R^{2a}$, at each occurrence, is independently $C_1$-$C_6$-alkyl, halo-$C_1$-$C_6$-alkyl, -$G^1$, or —$(CR^{4a}R^{5a})_n$-$G^1$, wherein $G^1$, $R^{4a}$, $R^{5a}$ and n are as defined in the Summary.

In one embodiment, $R^{2a}$, at each occurrence, is independently $C_1$-$C_6$-alkyl or halo-$C_1$-$C_6$-alkyl.

In an embodiment, $R^{2a}$, at each occurrence, is independently -$G^1$ or —$(CR^{4a}R^{5a})_m$-$G^1$, wherein $G^1$, $R^{4a}$, $R^{5a}$ and n are as defined in the Summary.

In an embodiment, $R^{4a}$, at each occurrence, is independently hydrogen, halogen, $C_1$-$C_6$-alkyl, or halo-$C_1$-$C_6$-alkyl.

In an embodiment, $R^{4a}$, at each occurrence, is independently hydrogen or $C_1$-$C_6$-alkyl.

In one embodiment, $R^{4a}$, at each occurrence, is hydrogen.

In one embodiment, $R^{4a}$, at each occurrence, is $C_1$-$C_6$-alkyl.

In one embodiment, $R^{5a}$, at each occurrence, is independently hydrogen, halogen, $C_1$-$C_6$-alkyl, or halo-$C_1$-$C_6$-alkyl.

In an embodiment, $R^{5a}$, at each occurrence, is independently hydrogen or $C_1$-$C_6$-alkyl.

In one embodiment, $R^{5a}$, at each occurrence, is hydrogen.

In one embodiment, $R^{5a}$, at each occurrence, is $C_1$-$C_6$-alkyl.

In an embodiment, $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen.

In one embodiment, $G^{Ar}$ is phenyl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen.

In one embodiment, $G^{Ar}$ is phenyl; wherein $G^{Ar}$ is unsubstituted or substituted with 1, 2, 3, 4, or 5 halogen.

In one embodiment, $G^{Ar}$ is 2-fluorophenyl.

In one embodiment, $G^{Ar}$ is 6-membered heteroaryl; wherein $G^{Ar}$ is unsubstituted or substituted with 1, 2, 3, or 4 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen.

In one embodiment, $G^{Ar}$ is 6-membered heteroaryl; wherein $G^{Ar}$ is unsubstituted or substituted with 1, 2, 3, or 4 halogen.

In an embodiment, $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$OR^c$, —$C(O)R^c$, —$C(O)OR^c$, —$C(O)N(R^c)_2$, —$SO_2R^a$, —$SO_2N(R^c)_2$, and —$CH_2G^3$, wherein $G^3$, $R^c$, and $R^d$ are as defined in the Summary.

In one embodiment, $G^1$ is aryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R^c$, —$C(O)OR^c$, —$C(O)N(R^c)_2$, —$SO_2R^a$, —$SO_2N(R^c)_2$, and —$CH_2G^3$, wherein $G^3$, $R^c$, and $R^d$ are as defined in the Summary.

In one embodiment, $G^1$ is aryl; wherein $G^1$ is unsubstituted or substituted with 1, 2, 3, 4, or 5 substituents selected from the group consisting of $C_1$-$C_6$-alkyl and —$CH_2G^3$, wherein $G^3$ is as defined in the Summary.

In one embodiment, $G^1$ is heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$OR^c$, —$C(O)R^c$, —$C(O)OR^c$, —$C(O)N(R^c)_2$, —$SO_2R^a$, —$SO_2N(R^c)_2$, and —$CH_2G^3$, wherein $G^3$, $R^c$, and $R^d$ are as defined in the Summary.

In one embodiment, $G^1$ is heteroaryl; wherein $G^1$ is unsubstituted or substituted with 1, 2, 3, 4, or 5 substituents selected from the group consisting of $C_1$-$C_6$-alkyl and —$CH_2G^3$, wherein $G^3$ is as defined in the Summary.

In an embodiment, $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$, wherein $R^c$, and $R^d$ are as defined in the Summary.

In one embodiment, $G^2$ is cycloalkyl or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$, wherein $R^c$ and $R^d$ are as defined in the Summary.

In one embodiment, $G^2$ is cycloalkyl; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$, wherein $R^c$ and $R^d$ are as defined in the Summary.

In one embodiment, $G^2$ is cycloalkyl; wherein $G^2$ is unsubstituted or substituted with 1, 2, 3, 4, or 5 substituents selected from the group consisting of halogen, —$OR^c$, and —$C(O)OR^c$, wherein $R^c$ is as defined in the Summary.

In one embodiment, $G^2$ is heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$, wherein $R^c$ and $R^d$ are as defined in the Summary.

In one embodiment, $G^2$ is heterocycle; wherein $G^2$ is unsubstituted or substituted with 1, 2, 3, 4, or 5 substituents selected from the group consisting of halogen, —$OR^c$, and —$C(O)OR^c$, wherein $R^c$ is as defined in the Summary.

In an embodiment, $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OC(O)R^{1a}$, —$OC(O)N(R^b)(R^{3a})$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl, wherein $R^a$, $R^b$, $R^{1a}$, $R^{2a}$, $R^{3a}$, $R^{4a}$, $R^{5a}$, and m are as defined in the Summary.

In one embodiment, $G^3$ is aryl or heteroaryl; wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl, wherein $R^a$, $R^{1a}$, $R^{2a}$, $R^{3a}$, $R^{4a}$, $R^{5a}$, and m are as defined in the Summary.

In one embodiment, $G^3$ is heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl, wherein $R^a$, $R^b$, $R^{2a}$, $R^{3a}$, $R^{4a}$, $R^{5a}$, and m are as defined in the Summary.

In one embodiment, $G^3$ is heterocycle, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl, wherein $R^a$, $R^b$, $R^{1a}$, $R^{2a}$, $R^{3a}$, $R^{4a}$, $R^{5a}$, and m are as defined in the Summary.

In one embodiment, $G^3$ is heterocycle, wherein each $G^3$ is independently unsubstituted or substituted with 1, 2, 3, 4 or 5 substituents selected from the group consisting of $C_1$-$C_6$-alkyl, halogen, —$OR^{1a}$,—and halo-$C_1$-$C_6$-alkyl, wherein $R^{1a}$ is as defined in the Summary.

In an embodiment, $L^1$ is a bond or —$CH_2$—.

In one embodiment, $L^1$ is a bond.

In one embodiment, $L^1$ is a —$CH_2$—.

In an embodiment, m, at each occurrence, is independently 1, 2, 3, 4, or 5.

In one embodiment, m, at each occurrence, is independently 1 or 2.

In one embodiment, n, at each occurrence, is independently 1, 2, 3, 4, or 5.

In one embodiment, n, at each occurrence, is independently 1 or 2.

In an embodiment, a compound of formula (I) is selected from compounds of formula (Ia), (Ib), or (Ic), wherein $L^1$, $G^{Ar}$, $Z^1$ and $Z^2$ are as defined in the Summary.

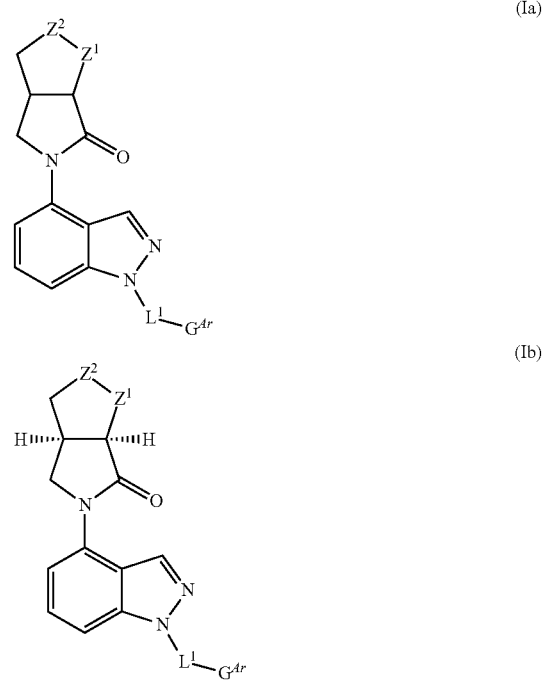

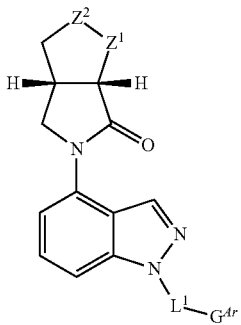
(Ic)

In one embodiment, a compound of formula (I) is selected from compounds of formula (Ia-1), (Ib-1), or (Ic-1), wherein $L^1$, $G^{Ar}$, and $R^1$ are as defined in the Summary.

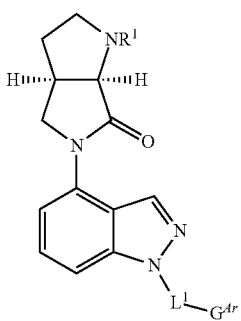
(Ia-1)

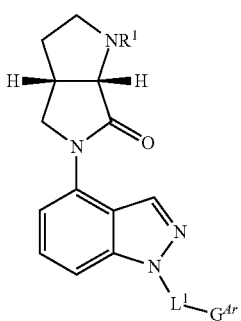
(Ib-1)

(Ic-1)

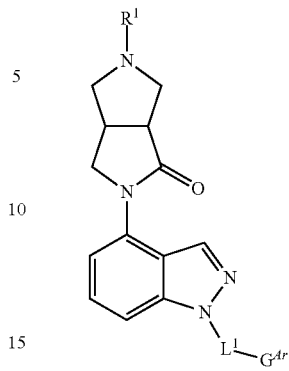
(Ia-2)

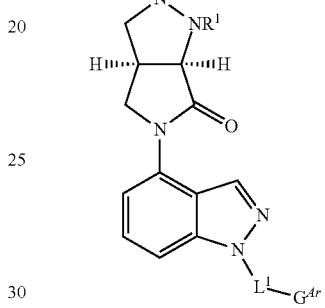
(Ib-2)

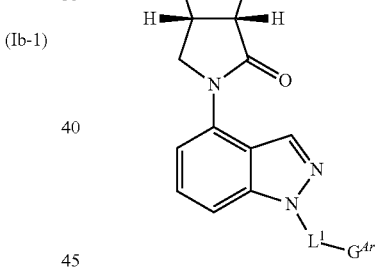
(Ic-2)

In one embodiment, a compound of formula (I) is selected from compounds of formula (Ia-2), (Ib-2), or (Ic-2), wherein $L^1$, $G^{Ar}$, and $R^1$ are as defined in the Summary.

In an embodiment, $Z^1$ is $NR^1$; $Z^2$ is $CH_2$; $R^1$ is selected from the group consisting of —$CH_2G^1$, —$CH_2G^2$, —C(O)-$G^1$, —C(O)-$G^2$, —C(O)—$R^2$, —C(O)N($R^a$)—$R^2$, —C(O)N($R^a$)($R^b$), —$SO_2$-$G^1$, —$SO_2$-$G^2$, —$SO_2$—$R^2$, —$SO_2$N($R^a$)—$R^2$, and —$SO_2$N($R^a$)($R^b$); $R^2$ is selected from the group consisting of $C_1$-$C_6$-alkyl, $C_2$-$C_6$-alkenyl, $C_2$-$C_6$-alkynyl, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$(CR^{4a}R^{5a})_m$-$G^2$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl;

wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^{1-}$, or —$(CR^{4a}R^{5a})_n$-$G^1$; $R^{2a}$, at each occurrence, is independently $C_1$-$C_6$-alkyl, halo-$C_1$-$C_6$-alkyl, or —$(CR^{4a}R^{5a})_n$-$G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, and halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R^c$, —$C(O)OR^c$, —$C(O)N(R^c)_2$, —$SO_2R^a$, —$SO_2N(R^c)_2$, and —$CH_2G^3$; $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl; $L^1$ is a bond or —$CH_2$—; and m and n, at each occurrence, are each independently 1, 2, 3, 4, or 5.

In an embodiment, $Z^1$ is $NR^1$; $Z^2$ is $CH_2$; $R^1$ is selected from the group consisting of —$CH_2G^1$, —$CH_2G^2$, —$SO_2$-$G^2$, —$SO_2$—$R^2$, —$SO_2N(R^a)$—$R^2$, and —$SO_2N(R^a)(R^b)$; $R^2$ is selected from the group consisting of $C_1$-$C_6$-alkyl, $C_2$-$C_6$-alkenyl, $C_2$-$C_6$-alkynyl, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$(CR^{4a}R^{5a})_m$-$G^2$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^{1-}$, or —$(CR^{4a}R^{5a})_n$-$G^1$; $R^{2a}$, at each occurrence, is independently $C_1$-$C_6$-alkyl, halo-$C_1$-$C_6$-alkyl, -$G^1$, or —$(CR^{4a}R^{5a})_n G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R^c$, —$C(O)OR^c$, —$C(O)N(R^c)_2$, —$SO_2R^a$, —$SO_2N(R^c)_2$, and —$CH_2G^3$; $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R$, —$C(O)OR^c$, —$C(O)N(R^c)_2$, —$SO_2R^a$, and —$SO_2N(R^c)_2$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl; C is a bond or —$CH_2$—; and m and n, at each occurrence, are each independently 1, 2, 3, 4, or 5.

In an embodiment, $Z^1$ is $NR^1$; $Z^2$ is $CH_2$; $R^1$ is selected from the group consisting of —$C(O)$-$G^1$, —$C(O)$-$G^2$, —$C(O)$—$R^2$, —$C(O)N(R^a)$—$R^2$, and —$C(O)N(R^a)(R^b)$; $R^2$ is selected from the group consisting of $C_1$-$C_6$-alkyl, $C_2$-$C_6$-alkenyl, $C_2$-$C_6$-alkynyl, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$(CR^{4a}R^{5a})_m$-$G^2$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^1$-, or —$(CR^{4a}R^{5a})_n G^1$; $R^{2a}$, at each occurrence, is independently $C_1$-$C_6$-alkyl, halo-$C_1$-$C_6$-alkyl, or —$(CR^{4a}R^{5a})_n G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R$, —$C(O)OR^c$, —$C(O)N(R^c)_2$, —$SO_2R^a$, —$SO_2N(R^c)_2$, and —$CH_2G^3$; $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl; $L^1$ is a bond or —$CH_2$—; and m and n, at each occurrence, are each independently 1, 2, 3, 4, or 5.

In an embodiment, $Z^1$ is $NR^1$; $Z^2$ is $CH_2$; $R^1$ is —$C(O)$-$G^2$; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen or $C_1$-$C_6$-alkyl; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^1$, or —$(CR^{4a}R^{5a})_n G^1$; $R^{2a}$, at each occurrence, is independently $C_1$-$C_6$-alkyl, halo-$C_1$-$C_6$-alkyl, -$G^1$, or —$(CR^{4a}R^{5a})_n$-$G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl; wherein $G^{Ar}$ is unsubstituted or substituted with 1, 2, or 3 substituents selected from the group consisting of $C_1$-$C_6$-alkyl, halo-$C_1$-$C_6$-alkyl, and halogen; $G^{1-}$ is aryl or heteroaryl; wherein $G^{1-}$is unsubstituted or substituted with 1, 2, 3, 4, or 5 substituents consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R^c$, —$C(O)OR^c$, —$C(O)N(R^c)_2$, —$SO_2R^a$, —$SO_2N(R^c)_2$, and —$CH_2G^3$; $G^2$ is cycloalkyl or heterocycle; wherein $G^2$ is unsubstituted or substituted with 1, 2, 3, 4, or 5 substituents selected from the group consisting of $C_1$-$C_6$-alkyl, cyano, halo-$C_1$-$C_6$-alkyl, halogen, and —$OR^c$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N$ $(R^a)C(O)R^{1a}$, $-(CR^{4a}R^{5a})_m-N(R^a)S(O)_2R^{2a}$, $-(CR^{4a}R^{5a})_m-N(R^a)C(O)O(R^{1a})$, $-(CR^{4a}R^{5a})_m-N(R^a)C(O)N(R^b)(R^{3a})$, cyano-$C_1$-$C_6$-alkyl, and halo-$C_1$-$C_6$-alkyl; $L^1$ is a bond or $-CH_2-$; and m and n, at each occurrence, are each independently 1, 2, 3, 4, or 5.

In an embodiment, $Z^1$ is $NR^1$; $Z^2$ is $CH_2$; $R^1$ is $-C(O)-R^2$; $R^2$ is $C_1$-$C_6$-alkyl or $-(CR^{4a}R^{5a})_m-OR^{1a}$; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ is hydrogen or $C_1$-$C_6$-alkyl; $R^{2a}$, at each occurrence, is independently $C_1$-$C_6$-alkyl, halo-$C_1$-$C_6$-alkyl, or $-(CR^{4a}R^{5a})_n$-$G^1$; $R^{3a}$, at each occurrence, is independently hydrogen, $C_1$-$C_6$-alkyl, halo-$C_1$-$C_6$-alkyl, -$G^1$, or $-(CR^{4a}R^{5a})_m$-$G^1$; $R^{4a}$ and $R^{5a}$, at each occurrence, are each independently hydrogen, $C_1$-$C_6$-alkyl, or halo-$C_1$-$C_6$-alkyl; $G^{Ar}$ is phenyl; wherein $G^{Ar}$ is unsubstituted or substituted with 1, 2, or 3 substituents selected from the group consisting of $C_1$-$C_6$-alkyl, halo-$C_1$-$C_6$-alkyl, and halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, $-N(R^c)_2$, $-N(R^c)C(O)R^c$, $-C(O)R^c$, $-C(O)OR^c$, $-C(O)N(R^c)_2$, $-SO_2R^a$, $-SO_2N(R^c)_2$, and $-CH_2G^3$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, $-NO_2$, $-OR^{1a}$, $-OC(O)R^{1a}$, $-OC(O)N(R^b)(R^{3a})$, $-SR^{1a}$, $-S(O)_2R^{2a}$, $-S(O)_2N(R^b)(R^{3a})$, $-C(O)R^{1a}$, $-C(O)OR^{1a}$, $-C(O)N(R^b)(R^{3a})$, $-N(R^b)(R^{3a})$, $-N(R^a)C(O)R^{1a}$, $-N(R^a)S(O)_2R^{2a}$, $-N(R^a)C(O)O(R^{1a})$, $-N(R^a)C(O)N(R^b)(R^{3a})$, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})$, $-(CR^{4a}R^{5a})_m-SR^{1a}$, $-(CR^{4a}R^{5a})_m-S(O)_2R^{2a}$, $-(CR^{4a}R^{5a})_m-S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)S(O)_2R^{2a}$, $-(CR^{4a}R^{5a})_m-N(R^a)C(O)O(R^{1a})$, $-(CR^{4a}R^{5a})_m-N(R^a)C(O)N(R^b)(R^{3a})$, cyano-$C_1$-$C_6$-alkyl, and halo-$C_1$-$C_6$-alkyl; $L^1$ is a bond; m at each occurrence, is independently is 1, 2, 3 or 4; and n at each occurrence, is independently 1, 2, 3, 4, or 5.

In an embodiment, $Z^1$ is $CH_2$; $Z^2$ is $NR^1$; $R^1$ is selected from the group consisting of $-CH_2G^1$, $-CH_2G^2$, $-C(O)-G^1$, $-C(O)-G^2$, $-C(O)-R^2$, $-C(O)N(R^a)-R^2$, $-C(O)N(R^a)(R^b)$, $-SO_2-G^2$, $-SO_2-R^2$, $-SO_2N(R^a)-R^2$, and $-SO_2N(R^a)(R^b)$; $R^2$ is selected from the group consisting of $C_1$-$C_6$-alkyl, $C_2$-$C_6$-alkenyl, $C_2$-$C_6$-alkynyl, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})$, $-(CR^{4a}R^{5a})_m-SR^{1a}$, $-(CR^{4a}R^{5a})_m-S(O)_2R^{2a}$, $-(CR^{4a}R^{5a})_m-S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)S(O)_2R^{2a}$, $-(CR^{4a}R^{5a})_m-N(R^a)C(O)O(R^{1a})$, $-(CR^{4a}R^{5a})_m-N(R^a)C(O)N(R^b)(R^{3a})$, $-(CR^{4a}R^{5a})_m$-$G^1$, $-(CR^{4a}R^{5a})_m$-$G^2$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^1$, or $-(CR^{4a}R^{5a})_n$-$G^1$; $R^{2a}$, at each occurrence, is independently $C_1$-$C_6$-alkyl, halo-$C_1$-$C_6$-alkyl, -$G^1$, or $-(CR^{4a}R^{5a})_n$-$G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, $-N(R^c)_2$, $-N(R^c)C(O)R^c$, $-C(O)R^c$, $-C(O)OR^c$, $-C(O)N(R^c)_2$, $-SO_2R^a$, $-SO_2N(R^c)_2$, and $-CH_2G^3$; $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, $-N(R^c)_2$, $-N(R^c)C(O)R^c$, $-C(O)R^c$, $-C(O)OR^c$, $-C(O)N(R^c)_2$, $-SO_2R^a$, and $-SO_2N(R^c)_2$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, $-NO_2$, $-OR^{1a}$, $-OC(O)R^{1a}$, $-OC(O)N(R^b)(R^{3a})$, $-SR^{1a}$, $-S(O)_2R^{2a}$, $-S(O)_2N(R^b)(R^{3a})$, $-C(O)R^{1a}$, $-C(O)OR^{1a}$, $-C(O)N(R^b)(R^{3a})$, $-N(R^b)(R^{3a})$, $-N(R^a)C(O)R^{1a}$, $-N(R^a)S(O)_2R^{2a}$, $-N(R^a)C(O)O(R^{1a})$, $-N(R^a)C(O)N(R^b)(R^{3a})$, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})$, $-(CR^{4a}R^{5a})_m-SR^{1a}$, $-(CR^{4a}R^{5a})_m-S(O)_2R^{2a}$, $-(CR^{4a}R^{5a})_m-S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)S(O)_2R^{2a}$, $-(CR^{4a}R^{5a})_m-N(R^a)C(O)O(R^{1a})$, $-(CR^{4a}R^{5a})_m-N(R^a)C(O)N(R^b)(R^{3a})$, cyano-$C_1$-$C_6$-alkyl, and halo-$C_1$-$C_6$-alkyl; Cis a bond or $-CH_2-$; and m and n, at each occurrence, are each independently 1, 2, 3, 4, or 5.

In an embodiment, $Z^1$ is $CH_2$; $Z^2$ is $NR^1$; $R^1$ is selected from the group consisting of $-CH_2G^1$ and $-CH_2G^2$; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^1$, or $-(CR^{4a}R^{5a})_n$-$G^1$; $R^{2a}$, at each occurrence, is independently $C_1$-$C_6$-alkyl, halo-$C_1$-$C_6$-alkyl, -$G^1$, or —$(CR^{4a}R^{5a})_n G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R^c$, —$C(O)OR^c$, —$C(O)N(R^c)_2$, —$SO_2R^a$, —$SO_2N(R^c)_2$, and —$CH_2G^3$; $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R^c$, —$C(O)OR^c$, —$C(O)N(R^c)_2$, —$SO_2R^a$, and —$SO_2N(R^c)_2$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, cyano-$C_1$-$C_6$-alkyl, and halo-$C_1$-$C_6$-alkyl; $L^1$ is a bond or —$CH_2$—; and m and n, at each occurrence, are each independently 1, 2, 3, 4, or 5.

In an embodiment, $Z^1$ is $CH_2$; $Z^2$ is $NR^1$; $R^1$ is —$CH_2G^1$; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen or $C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^{1a}$ and $R^{3a}$, at each occurrence, are each independently hydrogen, $C_1$-$C_6$-alkyl, halo-$C_1$-$C_6$-alkyl, -$G^1$, or —$(CR^{4a}R^{5a})_n G^1$; $R^{2a}$, at each occurrence, is independently $C_1$-$C_6$-alkyl, halo-$C_1$-$C_6$-alkyl, -$G^1$, or —$(CR^{4a}R^{5a})_n$-$G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl; wherein $G^{Ar}$ is unsubstituted or substituted with 1, 2, or 3 substituents selected from the group consisting of $C_1$-$C_6$-alkyl, halo-$C_1$-$C_6$-alkyl, and halogen; $G^1$ is aryl or heteroaryl; wherein $G^1$ is unsubstituted or substituted with 1, 2, 3, or 4 substituents selected from the group consisting of $C_1$-$C_6$-alkyl, halo-$C_1$-$C_6$-alkyl, halogen, and —$OR^c$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$(CR^{4a}R^{5a})_m$-$G^2$, cyano-$C_1$-$C_6$-alkyl, and halo-$C_1$-$C_6$-alkyl; $R^a$ and $R^b$, at each occurrence, are each independently hydrogen, $C_1$-$C_6$-alkyl, or halo-$C_1$-$C_6$-alkyl; $R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen; $R^d$ at each occurrence, is independently $C_1$-$C_6$-alkyl or halo-$C_1$-$C_6$-alkyl; $R^{1a}$ and $R^{3a}$, at each occurrence, are each independently hydrogen, $C_1$-$C_6$-alkyl, halo-$C_1$-$C_6$-alkyl, -$G^1$, or —$(CR^{4a}R^{5a})_n$-$G^1$; $R^{2a}$, at each occurrence, is independently $C_1$-$C_6$-alkyl, halo-$C_1$-$C_6$-alkyl, -$G^1$, or —$(CR^{4a}R^{5a})_n$-$G^1$; $R^{4a}$ and $R^{5a}$, at each occurrence, are each independently hydrogen, halogen, $C_1$-$C_6$-alkyl, or halo-$C_1$-$C_6$-alkyl; $G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, or halogen; $G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —$N(R^c)_2$, —$N(R^c)C(O)R^c$, —$C(O)R$, —$C(O)OR^c$, —$C(O)N(R^c)_2$, —$SO_2R^a$, —$SO_2N(R^c)_2$, and —$CH_2G^3$; $G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —$N(R^c)_2$, —$N(R^c)C(O)R^c$, —$C(O)R$, —$C(O)OR^c$, —$C(O)N(R^c)_2$, —$SO_2R^a$, and —$SO_2N(R^c)_2$; $G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —$OR^{1a}$, —$OC(O)R^{1a}$, —$OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)S(O)$_2$R$^{2a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), cyano-C$_1$-C$_6$-alkyl, and halo-C$_1$-C$_6$-alkyl; L$^1$ is a bond or —CH$_2$—; and m and n, at each occurrence, are each independently 1, 2, 3, 4, or 5.

In an embodiment, Z$^1$ is CH$_2$; Z$^2$ is NR$^1$; R$^1$ is selected from the group consisting of —C(O)-G$^1$, —C(O)-G$^2$, —C(O)—R$^2$, —C(O)N(R$^a$)—R$^2$, and —C(O)N(R$^a$)(R$^b$); R$^2$ is selected from the group consisting of C$_1$-C$_6$-alkyl, —(CR$^{4a}$R$^{5a}$)$_m$—OR$^{1a}$, —(CR$^{4a}$R$^{5a}$)$_m$—C(O)R$^{1a}$, —(CR$^{4a}$R$^{5a}$)$_m$—C(O)N(R$^b$)(R$^{3a}$), —(CR$^{4a}$R$^{5a}$)$_m$—N(R$^a$)C(O)R$^{1a}$, —(CR$^{4a}$R$^{5a}$)$_m$-G$^1$, —(CR$^{4a}$R$^{5a}$)$_m$-G$^2$, and halo-C$_1$-C$_6$-alkyl; R$^a$ and R$^b$, at each occurrence, are each independently hydrogen, C$_1$-C$_6$-alkyl or halo-C$_1$-C$_6$-alkyl; R$^c$ at each occurrence, is independently hydrogen or C$_1$-C$_6$-alkyl; R$^{1a}$ and R$^{3a}$, at each occurrence, are each independently hydrogen, C$_1$-C$_6$-alkyl, or halo-C$_1$-C$_6$-alkyl; R$^{2a}$, at each occurrence, is independently C$_1$-C$_6$-alkyl, halo-C$_1$-C$_6$-alkyl, -G$^1$, or —(CR$^{4a}$R$^{5a}$)$_m$-G$^1$; R$^{4a}$ and R$^{5a}$, at each occurrence, are each independently hydrogen or C$_1$-C$_6$-alkyl, or halo-C$_1$-C$_6$-alkyl; G$^{Ar}$ is phenyl; wherein G$^{Ar}$ is unsubstituted or substituted with 1, 2, or 3 substituents selected from the group consisting of C$_1$-C$_6$-alkyl, halo-C$_1$-C$_6$-alkyl, and halogen; G$^1$ is aryl or heteroaryl; wherein G$^1$ is unsubstituted or substituted with 1, 2, 3, or 4 substituents selected from the group consisting of C$_1$-C$_6$-alkyl, halo-C$_1$-C$_6$-alkyl, halogen and —CH$_2$G$^3$; G$^2$ is cycloalkyl or heterocycle; wherein G$^2$ is unsubstituted or substituted with 1, 2, 3, or 4 substituents selected from the group consisting of C$_1$-C$_6$-alkyl, halo-C$_1$-C$_6$-alkyl, halogen, and —OR$^c$; G$^3$ is aryl, heteroaryl, heterocycle, or cycloalkyl, wherein each G$^3$ is independently unsubstituted or substituted with 1, 2, 3, 4 or 5 substituents selected from the group consisting of C$_1$-C$_6$-alkyl, halogen, —OR$^{1a}$, and halo-C$_1$-C$_6$-alkyl; L$^1$ is a bond; m, at each occurrence, is independently 1, 2, 3, or 4; and n, at each occurrence, is independently 1, 2, 3, 4, or 5.

In an embodiment, Z$^1$ is CH$_2$; Z$^2$ is NR$^1$; R$^1$ is selected from the group consisting of —SO$_2$-G$^1$, —SO$_2$-G$^2$, —SO$_2$—R$^2$, —SO$_2$N(R$^a$)—R$^2$, and —SO$_2$N(R$^a$)(R$^b$); R$^2$ is selected from the group consisting of C$_1$-C$_6$-alkyl, C$_2$-C$_6$-alkenyl, C$_2$-C$_6$-alkynyl, —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)S(O)$_2$R$^{2a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$G$^1$, —(CR$^{4a}$R$^{5a}$)$_m$-G$^2$, cyano-C$_1$-C$_6$-alkyl, and halo-C$_1$-C$_6$-alkyl; R$^a$ and R$^b$, at each occurrence, are each independently hydrogen, C$_1$-C$_6$-alkyl, or halo-C$_1$-C$_6$-alkyl; R$^c$ at each occurrence, is independently hydrogen, C$_1$-C$_6$-alkyl, aryl, aryl-C$_1$-C$_6$-alkyl, cycloalkyl, cycloalkyl-C$_1$-C$_6$-alkyl, or halo-C$_1$-C$_6$-alkyl; wherein said aryl, the aryl of aryl-C$_1$-C$_6$-alkyl, the cycloalkyl, and the cycloalkyl of cycloalkyl-C$_1$-C$_6$-alkyl are independently unsubstituted or substituted with 1, 2 3, 4, or 5 substituents independently selected from the group consisting of C$_1$-C$_6$-alkyl, halo-C$_1$-C$_6$-alkyl, and halogen; R$^d$ at each occurrence, is independently C$_1$-C$_6$-alkyl or halo-C$_1$-C$_6$-alkyl; R$^{1a}$ and R$^{3a}$, at each occurrence, are each independently hydrogen, C$_1$-C$_6$-alkyl, halo-C$_1$-C$_6$-alkyl, -G$^1$, or —(CR$^{4a}$R$^{5a}$)$_n$-G$^1$; R$^{2a}$, at each occurrence, is independently C$_1$-C$_6$-alkyl, halo-C$_1$-C$_6$-alkyl, -G$^1$, or —(CR$^{4a}$R$^{5a}$)$_n$-G$^1$; R$^{4a}$ and R$^{5a}$, at each occurrence, are each independently hydrogen, halogen, C$_1$-C$_6$-alkyl, or halo-C$_1$-C$_6$-alkyl; G$^{Ar}$ is phenyl or a 6-membered heteroaryl; wherein G$^{Ar}$ is unsubstituted or substituted with 1, 2, 3, 4, or 5 substituents selected from the group consisting of C$_1$-C$_6$-alkyl, C$_2$-C$_6$-alkenyl, C$_2$-C$_6$-alkynyl, cyano, halo-C$_1$-C$_6$-alkyl, or halogen; G$^1$ is aryl or heteroaryl; wherein G$^1$ is unsubstituted or substituted with 1, 2, 3, 4, or 5 substituents selected from the group consisting of C$_1$-C$_6$-alkyl, C$_2$-C$_6$-alkenyl, C$_2$-C$_6$-alkynyl, cyano, halo-C$_1$-C$_6$-alkyl, halogen, nitro, —N(R$^c$)$_2$, —N(R$^c$)C(O)R$^c$, —C(O)R$^c$, —C(O)OR$^c$, —C(O)N(R$^c$)$_2$, —SO$_2$R$^a$, —SO$_2$N(R$^c$)$_2$, and —CH$_2$G$^3$; G$^2$ is cycloalkyl, cycloalkenyl, or heterocycle; wherein G$^2$ is unsubstituted or substituted with 1, 2, 3, 4, or 5 substituents selected from the group consisting of C$_1$-C$_6$-alkyl, C$_2$-C$_6$-alkenyl, C$_2$-C$_6$-alkynyl, cyano, halo-C$_1$-C$_6$-alkyl, halogen, nitro, oxo, —N(R$^c$)$_2$, —N(R$^c$)C(O)R$^c$, —C(O)R$^c$, —C(O)OR$^c$, —C(O)N(R$^c$)$_2$, —SO$_2$R$^a$, and —SO$_2$N(R$^c$)$_2$; G$^3$ is aryl, heteroaryl, heterocycle, cycloalkyl, or cycloalkenyl, wherein each G$^3$ is independently unsubstituted or substituted with 1, 2, 3, 4 or 5 substituents selected from the group consisting of C$_1$-C$_6$-alkyl, C$_2$-C$_6$-alkenyl, C$_2$-C$_6$-alkynyl, halogen, cyano, oxo, —NO$_2$, —OR$^{1a}$, —OC(O)R$^{1a}$, —OC(O)N(R$^b$)(R$^{3a}$), —SR$^{1a}$, —S(O)$_2$R$^{2a}$, —S(O)$_2$N(R$^b$)(R$^{3a}$), —C(O)R$^{1a}$, —C(O)OR$^{1a}$, —C(O)N(R$^b$)(R$^{3a}$), —N(R$^b$)(R$^{3a}$), —N(R$^a$)C(O)R$^{1a}$, —N(R$^a$)S(O)$_2$R$^{2a}$, —N(R$^a$)C(O)O(R$^{1a}$), —N(R$^a$)C(O)N(R$^b$)(R$^{3a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)S(O)$_2$R$^{2a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), cyano-C$_1$-C$_6$-alkyl, and halo-C$_1$-C$_6$-alkyl; L$^1$ is a bond or —CH$_2$—; and m and n, at each occurrence, are each independently 1, 2, 3, 4, or 5. In an embodiment, Z$^1$ is CH$_2$; Z$^2$ is NR$^1$; R$^1$ is selected from the group consisting of —SO$_2$-G$^1$, —SO$_2$-G$^2$ and —SO$_2$—R$^2$; R$^2$ is selected from the group consisting of C$_1$-C$_6$-alkyl, —(CR$^{4a}$R$^{5a}$)$_m$—OR$^{1a}$, —(CR$^{4a}$R$^{5a}$)$_m$—C(O)R$^{1a}$, —(CR$^{4a}$R$^{5a}$)$_m$-G$^1$, —(CR$^{4a}$R$^{5a}$)$_m$-G$^2$, and halo-C$_1$-C$_6$-alkyl; R$^c$ at each occurrence, is independently hydrogen or C$_1$-C$_6$-alkyl; R$^{1a}$, at each occurrence, is independently hydrogen, C$_1$-C$_6$-alkyl, or halo-C$_1$-C$_6$-alkyl; R$^{4a}$ and R$^{5a}$, at each occurrence, are each independently hydrogen, C$_1$-C$_6$-alkyl, or halo-C$_1$-C$_6$-alkyl; G$^{Ar}$ is phenyl; wherein G$^{Ar}$ is unsubstituted or substituted with 1, 2, or 3 substituents selected from the group consisting of C$_1$-C$_6$-alkyl, halo-C$_1$-C$_6$-alkyl, and halogen; G$^1$ is aryl or heteroaryl; wherein G$^1$ is unsubstituted or substituted with 1, 2, 3, or 4 substituents selected from the group consisting of C$_1$-C$_6$-alkyl, halo-C$_1$-C$_6$-alkyl, and halogen; G$^2$ is cycloalkyl or heterocycle; wherein G$^2$ is unsubstituted or substituted with 1, 2, 3, or 4 substituents selected from the group consisting of C$_1$-C$_6$-alkyl, halo-C$_1$-C$_6$-alkyl, halogen, —OR$^c$, —C(O)R$^c$, and —C(O)OR$^c$; L$^1$ is a bond; and m, at each occurrence, is independently 1, 2, 3 or 4.

Specific embodiments contemplated as part of the invention also include, but are not limited to, compounds of formula (I), as defined, for example:

(3aS,6aS)-5-[1-(2-fluorophenyl)-1H-indazol-4-yl]-1-(3-hydroxy-3-methylbutanoyl)hexahydropyrrolo[3,4-b]pyrrol-6(1H)-one;

(3aR,6aR)-5-[1-(2-fluorophenyl)-1H-indazol-4-yl]-1-(3-hydroxy-3-methylbutanoyl)hexahydropyrrolo[3,4-b]pyrrol-6(1H)-one;
(3aR*,6aR*)-5-[1-(2-fluorophenyl)-1H-indazol-4-yl]-1-[(3R)-tetrahydrofuran-3-ylcarbonyl]hexahydropyrrolo[3,4-b]pyrrol-6(1H)-one;
rel-(3aR,6aR)-5-[1-(2-fluorophenyl)-1H-indazol-4-yl]-1-(2-hydroxy-2-methylpropanoyl)hexahydropyrrolo[3,4-b]pyrrol-6(1H)-one;
rel-(3aR,6aR)-5-[1-(2-fluorophenyl)-1H-indazol-4-yl]-1-[(1-hydroxycyclopropyl)carbonyl]hexahydropyrrolo[3,4-b]pyrrol-6(1H)-one;
rel-(3aR,6aR)-1-acetyl-5-[1-(2-fluorophenyl)-1H-indazol-4-yl]hexahydropyrrolo[3,4-b]pyrrol-6(1H)-one;
(3aR*,6aR*)-5-[1-(2-fluorophenyl)-1H-indazol-4-yl]-1-[(3R)-3-hydroxybutanoyl]hexahydropyrrolo[3,4-b]pyrrol-6(1H)-one;
rel-(3aR,6aR)-2-[1-(2-fluorophenyl)-1H-indazol-4-yl]-5-(3-methylbutanoyl)hexahydropyrrolo[3,4-c]pyrrol-1(2H)-one;
rel-(3aR,6aR)-5-benzyl-2-[1-(2-fluorophenyl)-1H-indazol-4-yl]hexahydropyrrolo[3,4-c]pyrrol-1(2H)-one;
rel-(3aR,6aR)-2-[1-(2-fluorophenyl)-1H-indazol-4-yl]-5-(tetrahydrofuran-2-ylacetyl)hexahydropyrrolo[3,4-c]pyrrol-1(2H)-one;
rel-(3aR,6aR)-2-[1-(2-fluorophenyl)-1H-indazol-4-yl]-5-(3-hydroxybutanoyl)hexahydropyrrolo[3,4-c]pyrrol-1(2H)-one;
rel-(3aR,6aR)-2-[1-(2-fluorophenyl)-1H-indazol-4-yl]-5-(1H-imidazol-1-ylcarbonyl)hexahydropyrrolo[3,4-c]pyrrol-1(2H)-one;
rel-(3aR,6aR)-5-[1-(2-fluorophenyl)-1H-indazol-4-yl]-N-(1,3-oxazol-5-ylmethyl)-4-oxohexahydropyrrolo[3,4-c]pyrrole-2(1H)-carboxamide;
rel-(3aR,6aR)-2-[1-(2-fluorophenyl)-1H-indazol-4-yl]-5-[(5-methyl-1,2-oxazol-3-yl)carbonyl]hexahydropyrrolo[3,4-c]pyrrol-1(2H)-one;
rel-(3aR,6aR)-5-[1-(2-fluorophenyl)-1H-indazol-4-yl]-N,N-dimethyl-4-oxohexahydropyrrolo[3,4-c]pyrrole-2(1H)-carboxamide;
rel-(3aR,6aR)-2-[1-(2-fluorophenyl)-1H-indazol-4-yl]-5-(1,3-oxazol-4-ylcarbonyl)hexahydropyrrolo[3,4-c]pyrrol-1(2H)-one;
rel-(3aR,6aR)-5-acetyl-2-[1-(2-fluorophenyl)-1H-indazol-4-yl]hexahydropyrrolo[3,4-c]pyrrol-1 (2H)-one;
rel-(3aR,6aR)-2-[1-(2-fluorophenyl)-1H-indazol-4-yl]-5-(1,3-oxazol-2-ylmethyl)hexahydropyrrolo[3,4-c]pyrrol-1(2H)-one;
rel-(3aR,6aR)-2-[1-(2-fluorophenyl)-1H-indazol-4-yl]-5-isobutyrylhexahydropyrrolo[3,4-c]pyrrol-1 (2H)-one;
(3aR,6aS)-2-[1-(2-fluorophenyl)-1H-indazol-4-yl]-5-isobutyrylhexahydropyrrolo[3,4-c]pyrrol-1(2H)-one;
(3aS,6aS)-2-[1-(2-fluorophenyl)-1H-indazol-4-yl]-5-(isobutylsulfonyl)hexahydropyrrolo[3,4-c]pyrrol-1 (2H)-one;
(3aR,6aS)-2-[1-(2-fluorophenyl)-1H-indazol-4-yl]-5-[(2S)-tetrahydrofuran-2-ylacetyl]hexahydropyrrolo[3,4-c]pyrrol-1 (2H)-one;
(3aS,6aS)-5-(ethylsulfonyl)-2-[1-(2-fluorophenyl)-1H-indazol-4-yl]hexahydropyrrolo[3,4-c]pyrrol-1 (2H)-one;
(3aS,6aS)-2-[1-(2-fluorophenyl)-1H-indazol-4-yl]-5-(isopropylsulfonyl)hexahydropyrrolo[3,4-c]pyrrol-1 (2H)-one;
(3aR,6aS)-5-(1-benzofuran-3-ylacetyl)-2-[1-(2-fluorophenyl)-1H-indazol-4-yl]hexahydropyrrolo[3,4-c]pyrrol-1(2H)-one;
(3aS,6aS)-2-[1-(2-fluorophenyl)-1H-indazol-4-yl]-5-[(3,3,3-trifluoropropyl)sulfonyl]hexahydropyrrolo[3,4-c]pyrrol-1 (2H)-one;
(3aS,6aS)-2-[1-(2-fluorophenyl)-1H-indazol-4-yl]-5-(pyridin-3-ylsulfonyl)hexahydropyrrolo[3,4-c]pyrrol-1 (2H)-one;
(3aS,6aS)-5-(cyclopropylsulfonyl)-2-[1-(2-fluorophenyl)-1H-indazol-4-yl]hexahydropyrrolo[3,4-c]pyrrol-1 (2H)-one;
(3aS,6aS)-2-[1-(2-fluorophenyl)-1H-indazol-4-yl]-5-(phenylsulfonyl)hexahydropyrrolo[3,4-c]pyrrol-1 (2H)-one;
tert-butyl 4-{[(3aS,6aS)-5-[1-(2-fluorophenyl)-1H-indazol-4-yl]-4-oxohexahydropyrrolo[3,4-c]pyrrol-2(1H)-yl]sulfonyl}piperidine-1-carboxylate;
(3aR,6aS)-2-[1-(2-fluorophenyl)-1H-indazol-4-yl]-5-{[2-(pyrrolidin-1-ylmethyl)-1,3-oxazol-4-yl]carbonyl}hexahydropyrrolo[3,4-c]pyrrol-1 (2H)-one;
(3aR,6aS)-2-[1-(2-fluorophenyl)-1H-indazol-4-yl]-5-(tetrahydrofuran-3-ylcarbonyl)hexahydropyrrolo[3,4-c]pyrrol-1 (2H)-one;
(3aR,6aS)-5-[(3,5-dimethyl-1,2-oxazol-4-yl)acetyl]-2-[1-(2-fluorophenyl)-1H-indazol-4-yl]hexahydropyrrolo[3,4-c]pyrrol-1 (2H)-one;
(3aS,6aR)-2-[1-(2-fluorophenyl)-1H-indazol-4-yl]-5-[(3S)-3-hydroxybutanoyl]hexahydropyrrolo[3,4-c]pyrrol-1 (2H)-one;
(3aS,6aR)-2-[1-(2-fluorophenyl)-1H-indazol-4-yl]-5-(3-hydroxy-3-methylbutanoyl)hexahydropyrrolo[3,4-c]pyrrol-1(2H)-one;
(3aR,6aS)-2-[1-(2-fluorophenyl)-1H-indazol-4-yl]-5-[(3S)-3-hydroxybutanoyl]hexahydropyrrolo[3,4-c]pyrrol-1 (2H)-one;
(3aR,6aS)-2-[1-(2-fluorophenyl)-1H-indazol-4-yl]-5-(3-hydroxy-3-methylbutanoyl)hexahydropyrrolo[3,4-c]pyrrol-1(2H)-one;
(3aS,6aR)-2-[1-(2-fluorophenyl)-1H-indazol-4-yl]-5-[(3R)-3-hydroxybutanoyl]hexahydropyrrolo[3,4-c]pyrrol-1 (2H)-one;
(3aR,6aS)-2-[1-(2-fluorophenyl)-1H-indazol-4-yl]-5-[(3R)-3-hydroxybutanoyl]hexahydropyrrolo[3,4-c]pyrrol-1 (2H)-one;
(3aR,6aS)-5-[(2,2-difluorocyclopropyl)carbonyl]-2-[1-(2-fluorophenyl)-1H-indazol-4-yl]hexahydropyrrolo[3,4-c]pyrrol-1(2H)-one;
(3aS,6aR)-2-[1-(2-fluorophenyl)-1H-indazol-4-yl]-5-(2-hydroxy-2-methylpropanoyl)hexahydropyrrolo[3,4-c]pyrrol-1(2H)-one;
(3aS,6aR)-2-[1-(2-fluorophenyl)-1H-indazol-4-yl]-5-[(1-hydroxycyclopropyl)carbonyl]hexahydropyrrolo[3,4-c]pyrrol-1(2H)-one;
(3aS,6aR)-5-[(3-chlorocyclobutyl)carbonyl]-2-[1-(2-fluorophenyl)-1H-indazol-4-yl]hexahydropyrrolo[3,4-c]pyrrol-1(2H)-one;
3-[(3aR,6aS)-5-[1-(2-fluorophenyl)-1H-indazol-4-yl]-4-oxohexahydropyrrolo[3,4-c]pyrrol-2(1H)-yl]-3-oxopropanamide;
(3aS,6aR)-2-[1-(2-fluorophenyl)-1H-indazol-4-yl]-5-(3-hydroxypropanoyl)hexahydropyrrolo[3,4-c]pyrrol-1(2H)-one;
(3aS,6aR)-5-acetyl-2-[1-(2-fluorophenyl)-1H-indazol-4-yl]hexahydropyrrolo[3,4-c]pyrrol-1(2H)-one;
(3aR,6aR)-5-[1-(2-fluorophenyl)-1H-indazol-4-yl]-1-(2-hydroxy-2-methylpropanoyl)hexahydropyrrolo[3,4-b]pyrrol-6(1H)-one;
(3aR,6aR)-5-[1-(2-fluorophenyl)-1H-indazol-4-yl]-1-[(1-hydroxycyclopropyl)carbonyl]hexahydropyrrolo[3,4-b]pyrrol-6(1H)-one; and (3aS,6aS)-5-[1-(2-fluorophenyl)-1H-indazol-4-yl]-1-(2-hydroxy-2-methylpropanoyl)hexahydropyrrolo[3,4-b]pyrrol-6(1H)-one.

Compound names are assigned by using Name 2012 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present invention also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Methods for Preparing Compounds of the Invention

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-8.

Abbreviations: Boc for tert-butoxycarbonyl; DMAP for (dimethylamino)pyridine or N,N-dimethylpyridin-4-amine; Im for imidazole; Ms for methanesulfonyl; MsCl for methanesulfonyl chloride; Ph for phenyl; and psi for pounds per square inch.

Scheme 1

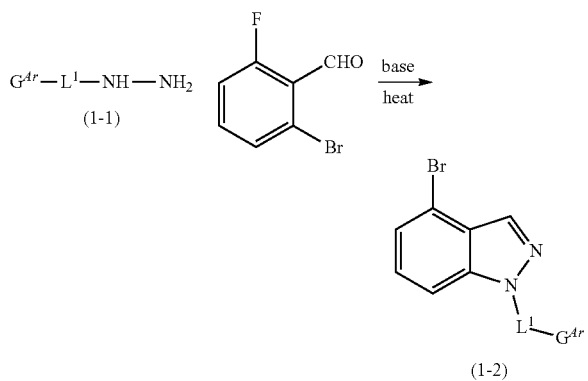

As illustrated in Scheme 1, compounds of formula (1-2) can be prepared from compounds of formula (1-1). Compounds of formula (1-1), wherein $L^1$ and $G^{Ar}$ are as defined in the Summary, can be reacted with 2-bromo-6-fluorobenzaldehyde in a solvent such as but not limited to N-methyl-2-pyrrolidinone in the presence of a base such as cesium carbonate. The mixture can be heated between 120 and 150° C. for 30 minutes to 4 hours to give compounds of formula (1-2).

Scheme 2

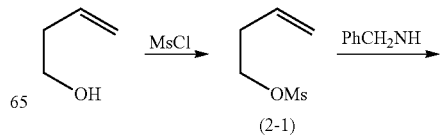

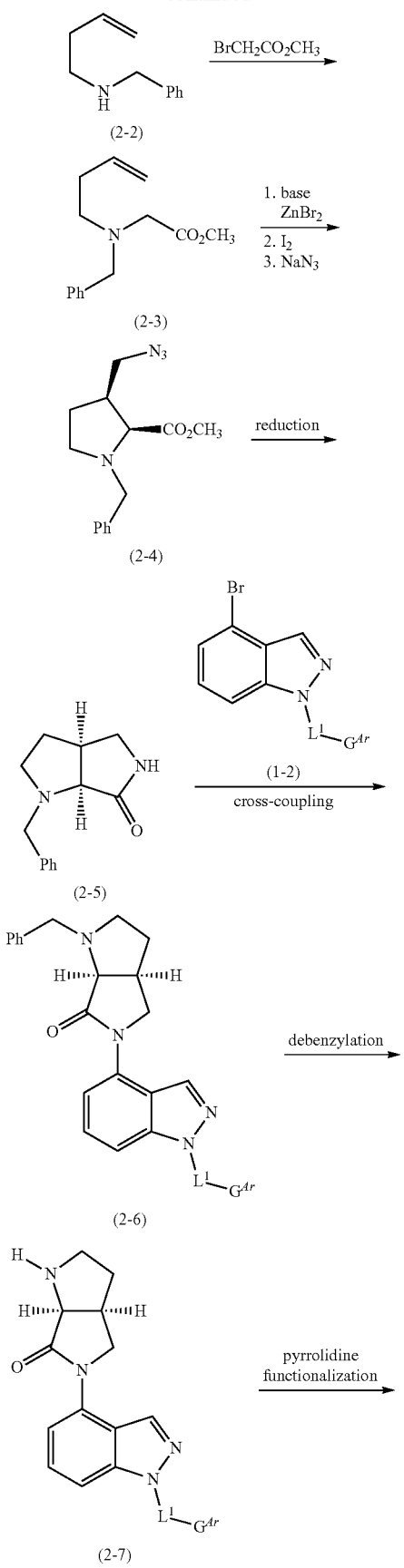

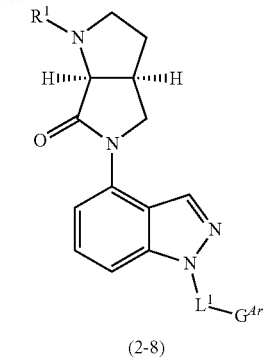

As illustrated in Scheme 2, compounds of formula (2-8), wherein $L^1$, $G^{Ar}$ and $R^1$ are as defined in the Summary, can be prepared starting from 3-buten-1-ol. Accordingly, 3-buten-1-ol can be sulfonylated with methanesulfonyl chloride in the presence of a tertiary amine base such as triethylamine or diisopropylethylamine in dichloromethane at or near room temperature over 30 minutes to 6 hours to deliver the sulfonate of formula (2-1). The sulfonate of formula (2-1) can be reacted with benzylamine in a solvent such as acetonitrile heated to reflux for 1-24 hours to obtain the compound of formula (2-2). The benzylamine of formula (2-2) can be alkylated with methyl bromoacetate in the presence of a tertiary amine base such as triethylamine or diisopropylethylamine in a solvent such as dimethyl sulfoxide at or near room temperature over 30 minutes to 24 hours to obtain the compound of formula (2-3). The compound of formula (2-3) can be reacted with a base such as lithium diisopropylamide in cold (−78° C.) diethyl ether for 5-30 minutes and then cooled to −90° C. where a solution of zinc bromide in diethyl ether can be added and then gradually warmed to ambient temperature. The reaction mixture can be cooled to approximately 0° C. and then treated with a solution of iodine in diethyl ether with gradual warming to ambient temperature where the reaction was maintained for 15 minutes to 4 hours to supply an intermediate iodide, wherein the two carbon-attached pyrrolidine substituents are predominantly cis. The intermediate iodide can be reacted with sodium azide in a solvent such as N,N-dimethylformamide at temperatures between room temperature and 60° C. over 30 minutes to 3 hours to give the compound of formula (2-4) (Chang, L L, et al. Bioorg. Med. Chem. Lett. 2008; 18:1688-1691). The compound of formula (2-4) can be treated with triphenylphosphine in a solvent mixture such as tetrahydrofuran and water or 2-methyltetrahydrofuran and water heated to 65-85° C. for 1-4 hours to give they cyclized compound of formula (2-5). The compound of formula (2-5) can undergo a cross-coupling reaction with compounds of formula (1-2) in the presence of copper(I) iodide, potassium phosphate tribasic, and racemic trans-N,N'-dimethylcyclohexane-1,2-diamine under an inert atmosphere in dioxane heated to 90-120° C. over 4-24 hours optionally in a pressure tube to give compounds of formula (2-6) (Buchwald, S L et al. J. Am. Chem. Soc. 2001; 123; 7727-7729). Additional copper(I) iodide and diamine ligand may be introduced with continued heating for optimal yield. Catalytic hydrogenation (20-50 psi) over 20% palladium hydroxide on activated charcoal in a solvent such as tetrahydrofuran at or near room temperature over 4-24 hours removes the benzyl group from compounds of formula (2-6) giving compounds of formula (2-7). The pyrrolidine thus revealed in compounds of formula (2-7) can be functionalized as described in Scheme 7 to give compounds of formula (2-8). The enantiomer of compounds of formula (2-8) can be separated using a chiral chromatography column. Supercritical fluid chromatography using a chiral chromatography column can be used to separate the enantiomer of compounds of formula (2-8). Compounds of formula (2-8) are representative of compounds of formula (I).

Scheme 3

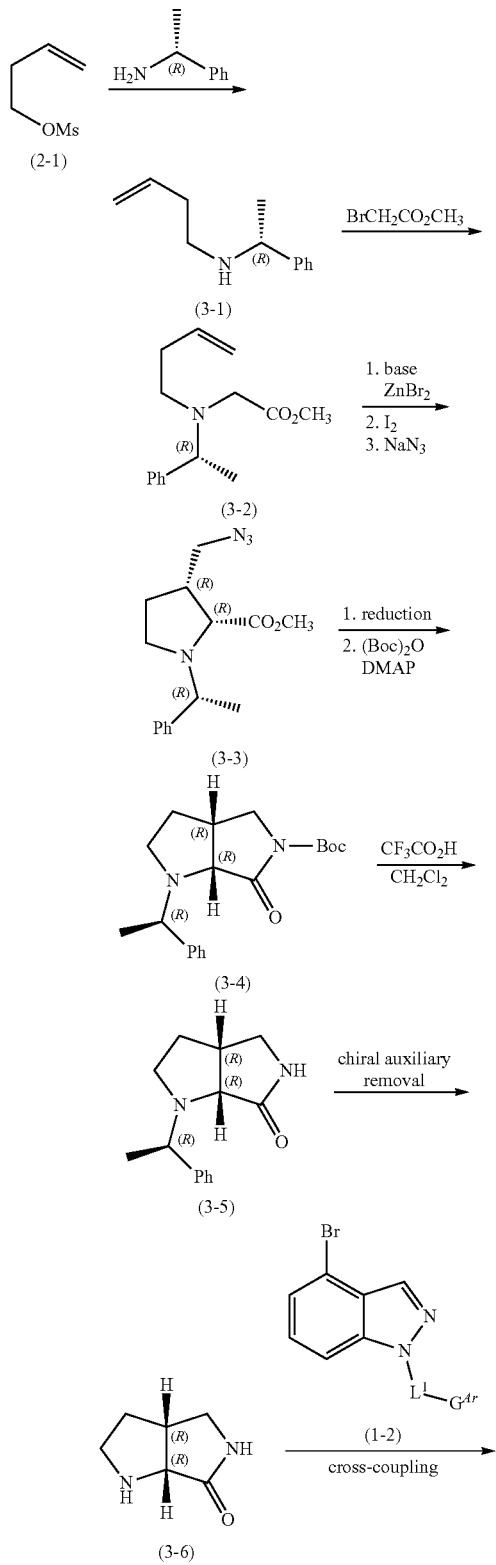

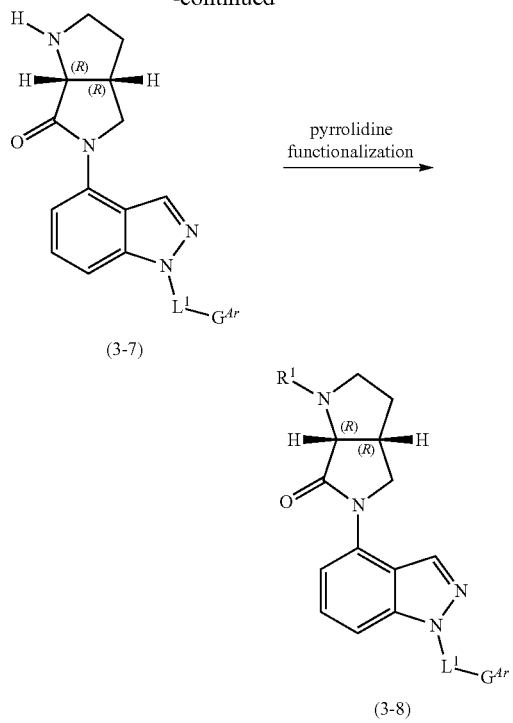

As shown in Scheme 3, the compound of formula (2-1) can be converted to chiral compounds of formula (3-8), wherein $L^1$, $G^{Ar}$ and $R^1$ are as defined in the Summary. To this end, the compound of formula (2-1) can be reacted using the conditions described in Scheme 2 and substituting (R)-1-phenylethanamine for benzylamine to give the chiral compound of formula (3-1). The compound of formula (3-1) can undergo the subsequent steps described in Scheme 2 to give sequentially the chiral compounds of formulas (3-2) and (3-3). The compound of formula (3-3) can be treated with triphenylphosphine in a solvent mixture such as tetrahydrofuran and water or 2-methyltetrahydrofuran and water heated to 65-85° C. for 1-4 hours to give they cyclized compound, (3aR,6aR)-1-[(1R)-1-phenylethyl]hexahydropyrrolo[3,4-b]pyrrol-6(1H)-one. (3aR,6aR)-1-[(1R)-1-Phenylethyl]hexahydropyrrolo[3,4-b]pyrrol-6(1H)-one can be reacted with di-tert-butyl dicarbonate in the presence of N,N-dimethylpyridin-4-amine and optionally in the presence of a tertiary amine base such as N,N-diisopropylethylamine or triethylamine in a solvent such as acetonitrile or N,N-dimethylformamide at ambient temperature over 1 to 24 hours to give the compound of formula (3-4). Chromatographic purification at this stage separates diastereomeric impurities. Treatment of the compound of formula (3-4) with an acid such as trifluoroacetic acid in dichloromethane or hydrochloric acid in dioxane at ambient temperature over 30 minutes to 6 hours gives the compound of formula (3-5). Catalytic hydrogenation (20-50 psi) over 20% palladium hydroxide on activated charcoal in a solvent such as ethanol or trifluoroethanol at 25-85° C. over 2-24 hours removes the phenylethyl group from the compound of formula (3-5) giving the compound of formula (3-6). The compound of formula (3-6) can be transformed to compounds of formula (3-7) by reaction with compounds of formula (1-2) in the presence of copper(I) iodide, potassium phosphate tribasic, and racemic trans-N,N'-dimethylcyclohexane-1,2-diamine under an inert atmosphere in dioxane heated to 90-120° C.

over 4-36 hours optionally in a pressure tube. The pyrrolidine in compounds of formula (3-7) can be functionalized as described in Scheme 7 to give compounds of formula (3-8). The compounds of formula (3-8) are representative of compounds of formula (I).

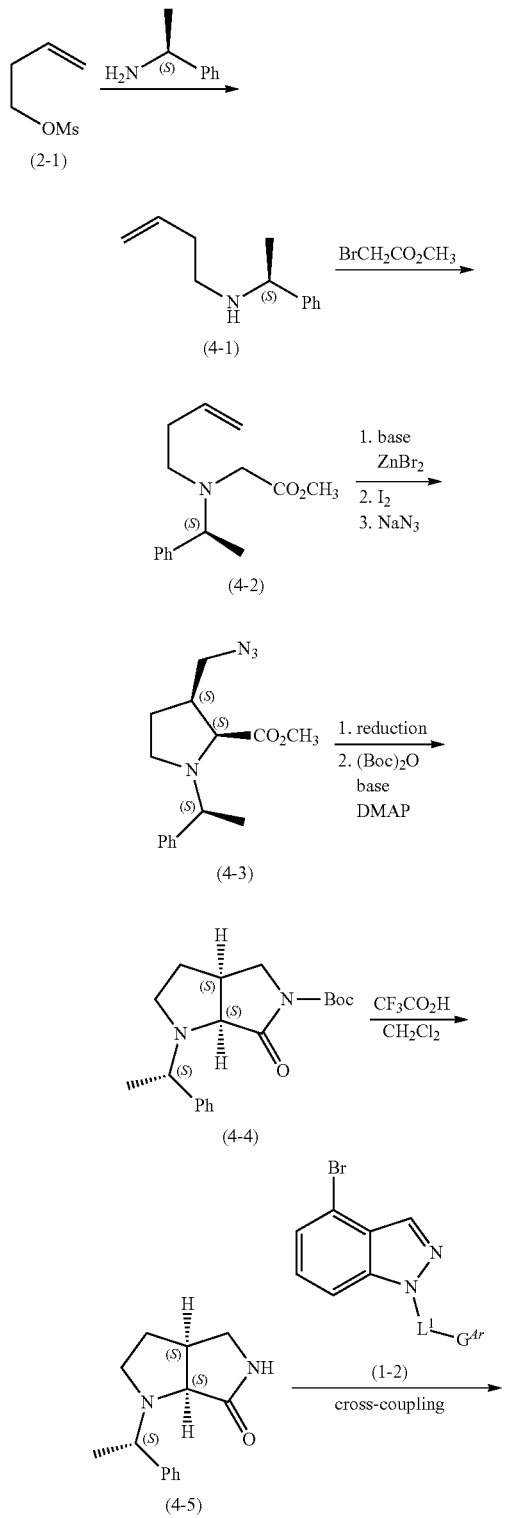

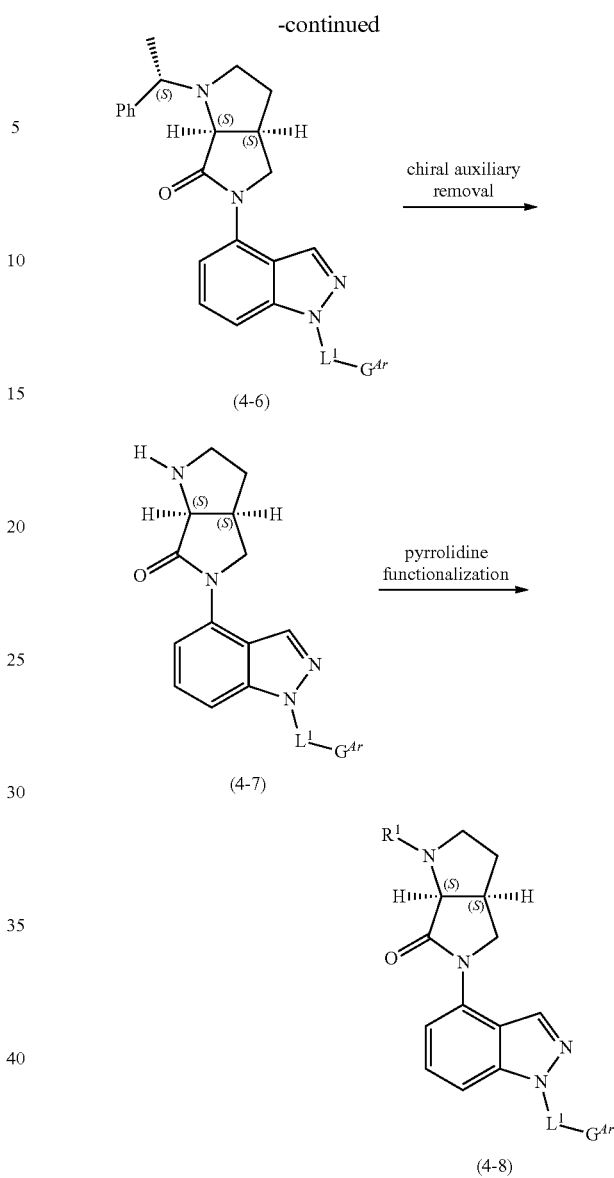

As shown in Scheme 4, the compound of formula (2-1) can be converted to compounds of formula (4-8). To this end, the compound of formula (2-1) can be reacted using the conditions described in Scheme 2 and substituting (S)-1-phenylethanamine for benzylamine to give the chiral compound of formula (4-1). The compound of formula (4-1) can undergo the subsequent steps described in Scheme 2 to give sequentially the chiral compounds of formulas (4-2) and (4-3). The compound of formula (4-3) can be treated with triphenylphosphine in a solvent mixture such as tetrahydrofuran and water or 2-methyltetrahydrofuran and water heated to 65-85° C. for 1-4 hours to give predominantly the cyclized compound, (3aS,6aS)-1-[(1S)-1-phenylethyl]hexahydropyrrolo[3,4-b]pyrrol-6(1H)-one. (3aS,6aS)-1-[(1S)-1-Phenylethyl]hexahydropyrrolo[3,4-b]pyrrol-6(1H)-one can be reacted with di-tert-butyl dicarbonate in the presence of a tertiary amine base such as N,N-diisopropylethylamine or triethylamine and optionally in the presence of a catalytic amount of N,N-dimethylpyridin-4-amine in a solvent such as N,N-dimethylformamide or acetonitrile at ambient temperature over 1 to 24 hours to give the compound of formula (4-4). Chromatographic purification at this stage separates diastereomeric impurities. Treatment of the compound of formula (4-4) with an acid such as trifluoroacetic acid in dichloromethane or hydrochloric acid in dioxane at ambient temperature over 30 minutes to 6 hours gives the compound of formula (4-5). The compound of formula (4-5) can be transformed to compounds of formula (4-6) by reaction with compounds of formula (1-2) in the presence of copper(I) iodide, potassium phosphate tribasic, and racemic trans-N,N'-dimethylcyclohexane-1,2-diamine under an inert atmosphere in dioxane heated to 90-120° C. over 1-8 hours optionally in a pressure tube. Catalytic hydrogenation (20-50 psi) over 20% palladium hydroxide on activated charcoal in a solvent such as ethanol or trifluoroethanol at 20-50° C. over 15-120 minutes removes the phenylethyl group from the compounds of formula (4-6) giving the compounds of formula (4-7). The pyrrolidine in compounds of formula (4-7) can be functionalized as described in Scheme 7 to give compounds of formula (4-8). The compounds of formula (4-8) are representative of compounds of formula (I).

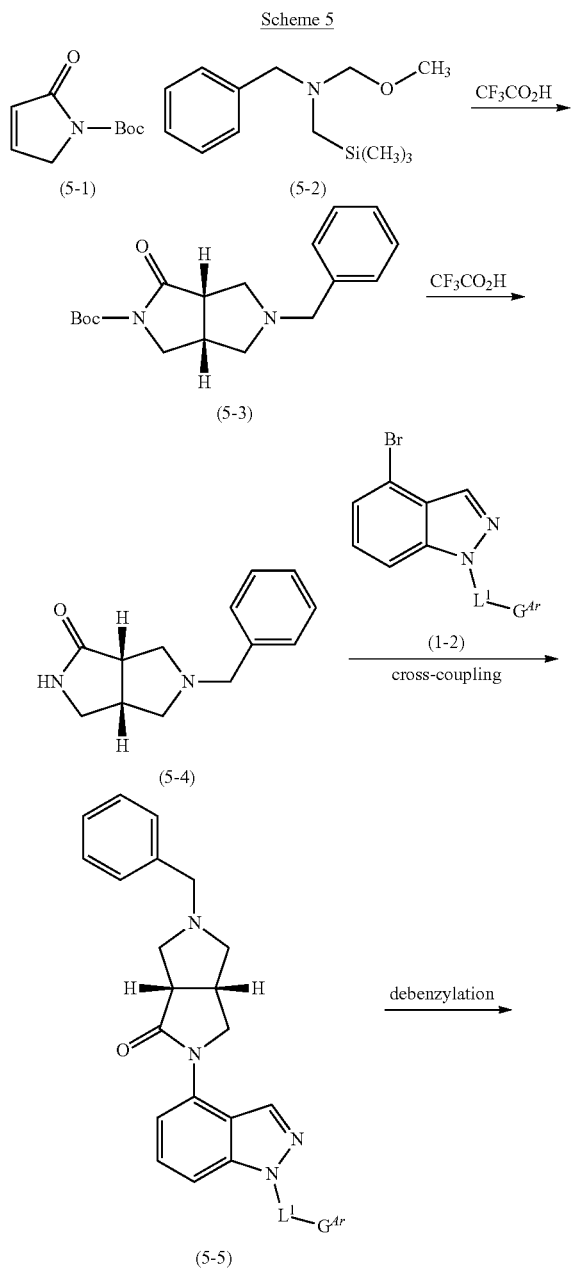

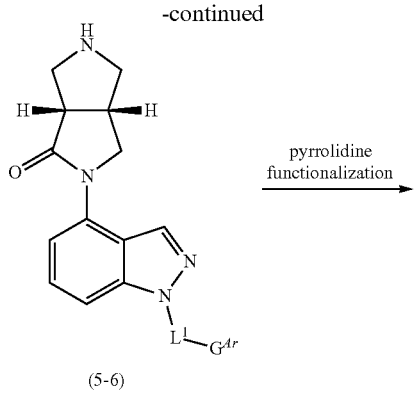

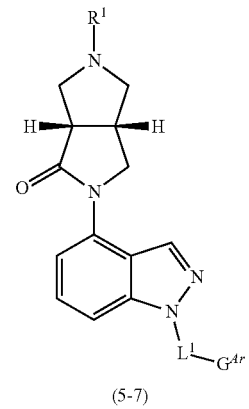

As illustrated in Scheme 5, compounds of formula (5-7) can be prepared starting from compounds of formula (5-1) and formula (5-2). Compounds of formula (5-1) and formula (5-2) can be combined in chilled (approximately 0° C.) dichloromethane in the presence of catalytic trifluoroacetic acid with subsequent warming to ambient temperature which can be maintained for 6-24 hours to the compound of formula (5-3). The tert-butoxycarbonyl protecting group of the compound of formula (5-3) can be removed by treatment with acid such as trifluoroacetic acid in dichloromethane or hydrochloric acid in dioxane to give the compound of formula (5-4). The compound of formula (5-4) can undergo a cross-coupling reaction with compounds of formula (1-2) in the presence of copper(I) iodide, potassium phosphate tribasic, and racemic trans-N,N'-dimethylcyclohexane-1,2-diamine under an inert atmosphere in dioxane heated to 90-120° C. over 12-60 hours to give compounds of formula (5-5). Catalytic hydrogenation (30-60 psi) over 20% palladium hydroxide on activated charcoal in a solvent such as tetrahydrofuran at or near room temperature to 60° C. over 4-24 hours removes the benzyl group from compounds of formula (5-5) giving compounds of formula (5-6). The pyrrolidine thus revealed in compounds of formula (5-6) can be functionalized as described in Scheme 8 to give compounds of formula (5-7), wherein $G^{Ar}$, and $R^1$, are as defined in the Summary. Compounds of formula (5-7) are representative of compounds of formula (I).

Scheme 6

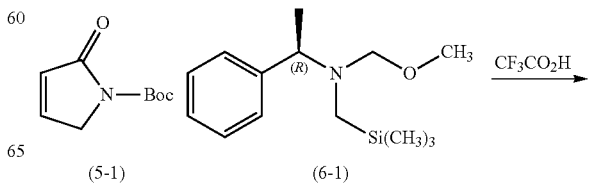

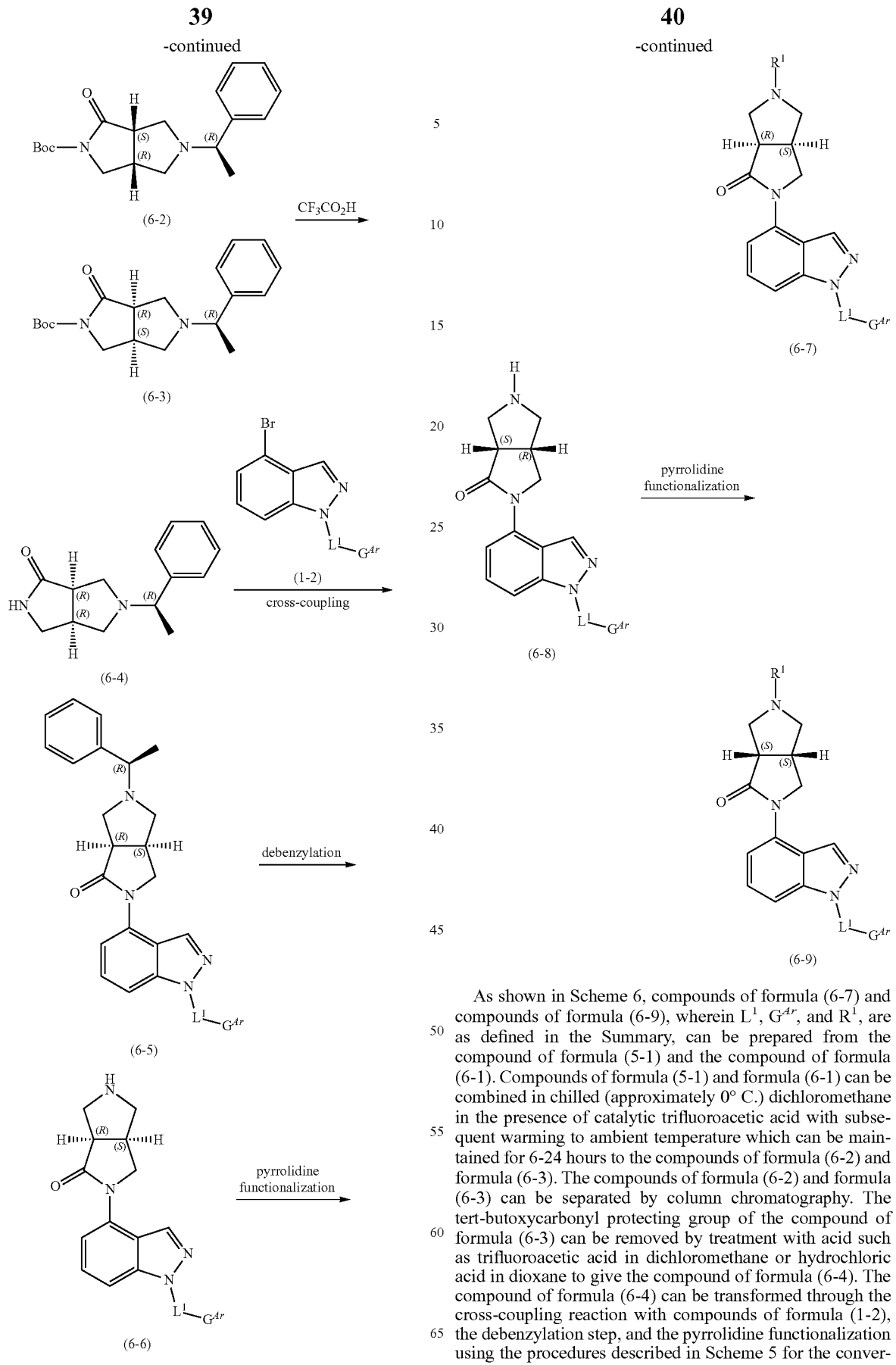

As shown in Scheme 6, compounds of formula (6-7) and compounds of formula (6-9), wherein $L^1$, $G^{Ar}$, and $R^1$, are as defined in the Summary, can be prepared from the compound of formula (5-1) and the compound of formula (6-1). Compounds of formula (5-1) and formula (6-1) can be combined in chilled (approximately 0° C.) dichloromethane in the presence of catalytic trifluoroacetic acid with subsequent warming to ambient temperature which can be maintained for 6-24 hours to the compounds of formula (6-2) and formula (6-3). The compounds of formula (6-2) and formula (6-3) can be separated by column chromatography. The tert-butoxycarbonyl protecting group of the compound of formula (6-3) can be removed by treatment with acid such as trifluoroacetic acid in dichloromethane or hydrochloric acid in dioxane to give the compound of formula (6-4). The compound of formula (6-4) can be transformed through the cross-coupling reaction with compounds of formula (1-2), the debenzylation step, and the pyrrolidine functionalization using the procedures described in Scheme 5 for the conversion of the compound of formula (5-4) to the compounds of formula (5-7) to give the chiral compounds of formula (6-7). An alternative procedure for the conversion of compounds of formula (6-5) to compounds of formula (6-6) can be accomplished by treatment of compounds of formula (6-5) with 1-chloroethyl chloroformate in dichloromethane initially at 0° C. followed by step-wise increases to room temperature and then 50° C. The enantiomeric compounds of formula (6-9) can be obtained by carrying the compound of formula (6-2) through the same sequence. The chiral compounds of formula (6-7) and formula (6-9) are representative of compounds of formula (I).

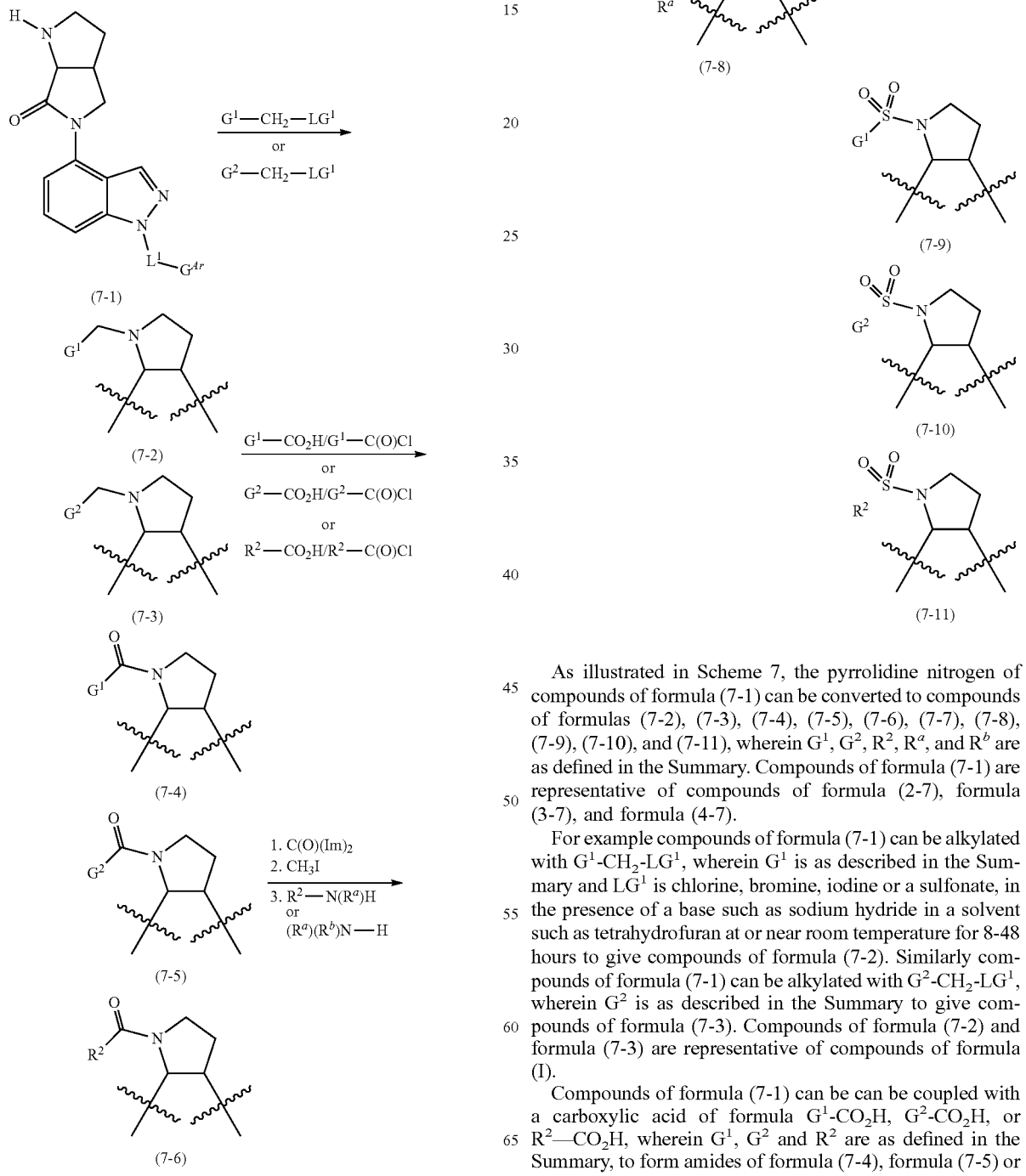

As illustrated in Scheme 7, the pyrrolidine nitrogen of compounds of formula (7-1) can be converted to compounds of formulas (7-2), (7-3), (7-4), (7-5), (7-6), (7-7), (7-8), (7-9), (7-10), and (7-11), wherein $G^1$, $G^2$, $R^2$, $R^a$, and $R^b$ are as defined in the Summary. Compounds of formula (7-1) are representative of compounds of formula (2-7), formula (3-7), and formula (4-7).

For example compounds of formula (7-1) can be alkylated with $G^1$-$CH_2$-$LG^1$, wherein $G^1$ is as described in the Summary and $LG^1$ is chlorine, bromine, iodine or a sulfonate, in the presence of a base such as sodium hydride in a solvent such as tetrahydrofuran at or near room temperature for 8-48 hours to give compounds of formula (7-2). Similarly compounds of formula (7-1) can be alkylated with $G^2$-$CH_2$-$LG^1$, wherein $G^2$ is as described in the Summary to give compounds of formula (7-3). Compounds of formula (7-2) and formula (7-3) are representative of compounds of formula (I).

Compounds of formula (7-1) can be can be coupled with a carboxylic acid of formula $G^1$-$CO_2H$, $G^2$-$CO_2H$, or $R^2$—$CO_2H$, wherein $G^1$, $G^2$ and $R^2$ are as defined in the Summary, to form amides of formula (7-4), formula (7-5) or formula (7-6), respectively. Examples of conditions known to generate amides from a mixture of a carboxylic acid and an amine (a compound of formula (7-1)) include but are not limited to adding a coupling reagent such as but not limited to N-(3-dimethylaminopropyl)-N-ethylcarbodiimide or 1-(3-dimethylaminopropyl)-3-ethylcarbodiimide (EDC, EDAC or EDCI), 1,3-dicyclohexylcarbodiimide (DCC), bis (2-oxo-3-oxazolidinyl)phosphinic chloride (BOPCl), 1-[bis (dimethylamino)methylene]-1H-1,2,3-triazolo[4,5-b]pyridinium 3-oxid hexafluorophosphate or (dimethylamino)-N, N-dimethyl(3-oxido-1H-[1,2,3]triazolo[4,5-b]pyridin-1-yl) methaniminium hexafluorophosphate (HATU), 0-(benzotriazol-1-yl)-NA, N, N-tetramethyluronium tetrafluoroborate (TBTU), 2-(1H-benzo[d][1,2,3]triazol-1-yl)-1, 1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino) pyridine (DMAP), 1-hydroxy-7-azabenzotriazole (HOAT), 1-hydroxybenzotriazole (HOBT), and ethyl (hydroxyimino) cyanoacetate. The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, ethyl acetate, and acetonitrile. The coupling reactions may be carried out from 10 minutes to 24 hours at ambient or elevated temperatures. Compounds of formula (7-4), formula (7-5) and formula (7-6) are representative of compounds of formula (I).

Alternatively, compounds of formula (7-1) can be reacted with acid chlorides of $G^1$-C(O)Cl, $G^2$-C(O)Cl, or $R^2$—C(O) Cl to form amides of formula (7-4), formula (7-5) or formula (7-6), respectively. The reactions can be performed in the presence of a base such as diisopropylethylamine in a solvent such as dichloromethane at room temperature over 8-24 hours.

Compounds of formula (7-1) can be converted to ureas of formula (7-7) and formula (7-8) with a three-step process. In the first step, compounds of formula (7-1) can be reacted with 1,1'-carbonyldiimidazole in refluxing tetrahydrofuran over 8-24 hours. In the second step, the intermediate carbonylimidazole is alkylated with iodomethane in a solvent such as acetonitrile at room temperature over 6-24 hours. In the final step, the intermediate methylated imidazolium iodide is reacted with amines of formula $R^2$—N($R^a$)H or ($R^a$)($R^b$)N—H, wherein $R^a$, $R^b$ and $R^2$ are as defined in the Summary, in the presence of a tertiary amine base such as triethylamine or diisopropylethylamine in a solvent such as dichloromethane or tetrahydrofuran at room temperature over 20 minutes to 2 hours to give the compounds of formula (7-7) and formula (7-8), respectively. Compounds of formula (7-7) and formula (7-8) are representative of compounds of formula (I).

Compounds of formula (7-1) can be converted to sulfonamides of formula (7-9), formula (7-10), and formula (7-11). Accordingly, compounds of formula (7-1) can be reacted with sulfonyl chlorides of formulas $G^1SO_2Cl$, $G^2SO_2Cl$, or $R^2$—$SO_2Cl$, wherein $G^1$, $G^2$ and $R^2$ are as defined in the Summary, in the presence of triethylamine in ambient dichloromethane over 30 minutes to 4 hours to give compounds of formula (7-9), formula (7-10) or formula (7-11), respectively. Compounds of formula (7-9), formula (7-10) and formula (7-11) are representative of compounds of formula (I).

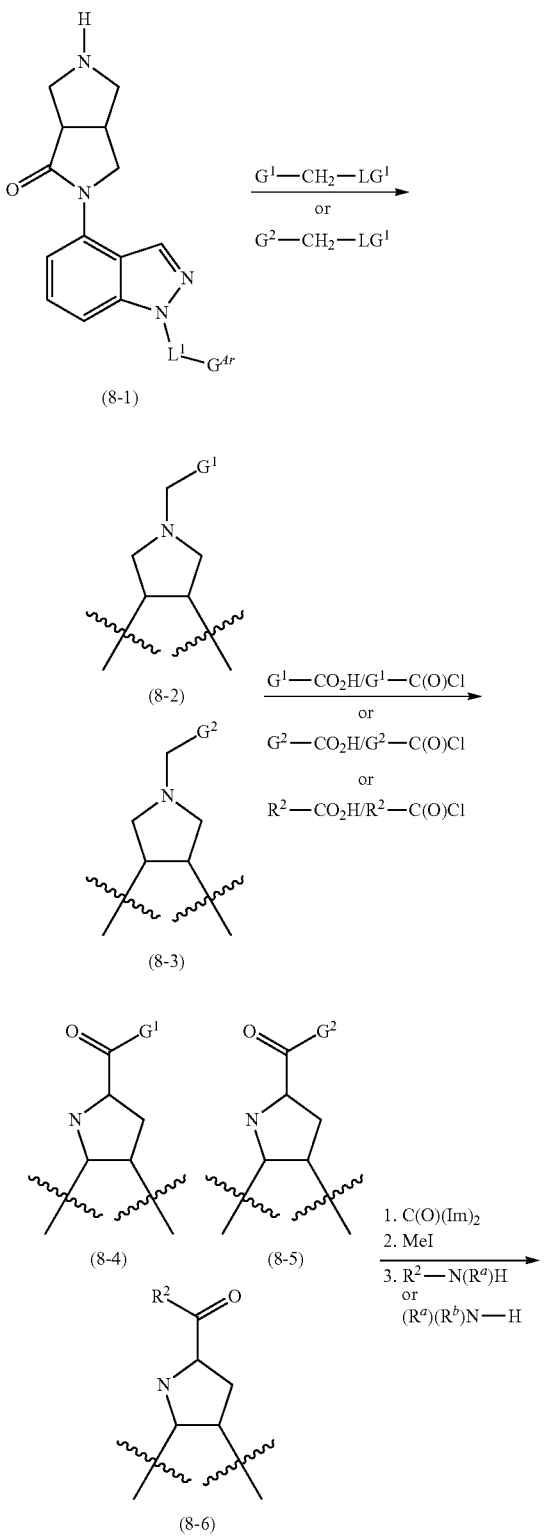

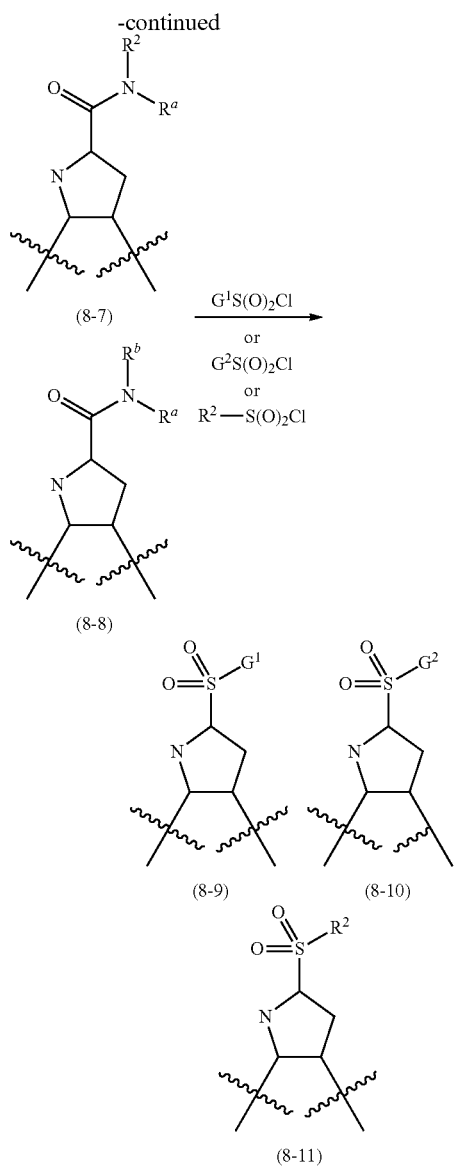

As illustrated in Scheme 8, the pyrrolidine nitrogen of compounds of formula (8-1) can be converted to compounds of formulas (8-2), (8-3), (8-4), (8-5), (8-6), (8-7), (8-8), (8-9), (8-10), and (8-11), wherein $G^1$, $G^2$, $R^2$, $R^a$, and $R^b$ are as defined in the Summary. Compounds of formula (8-1) are representative of compounds of formula (5-6), formula (6-6) and formula (6-8). Compounds of formula (8-1) can be transformed to compounds of formulas (8-2), (8-3), (8-4), (8-5), (8-6), (8-7), (8-8), (8-9), (8-10), and (8-11) using the methodologies described in Scheme 7 for the conversion of compounds of formula (7-1) to compounds of formulas (7-2), (7-3), (7-4), (7-5), (7-6), (7-7), (7-8), (7-9), (7-10), and (7-11), respectively. Compounds of formulas (8-2), (8-3), (8-4), (8-5), (8-6), (8-7), (8-8), (8-9), (8-10), and (8-11) are representative of compounds of formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection, for topical administration, or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$-alkyl esters and $C_5$-to-$C_7$-cycloalkyl esters, although $C_1$-to-$C_4$-alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$-alkyl amines and secondary $C_1$-to-$C_6$-dialkyl amines. In the case of secondary amines, the amine may also be in the form of a 5- or 6-membered heterocycle containing one nitrogen atom. Amides derived from ammonia, $C_1$-to-$C_3$-alkyl primary amides and $C_1$-to-$C_2$-dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of voltage-gated sodium channels (e.g., $Na_v1.7$ and $Na_v1.8$) in cells, the compounds described in the invention can affect physiological processes in humans and animals. In this way, the compounds and compositions described in the invention are useful for treating and preventing diseases and disorders modulated by voltage-gated sodium channels, e.g., $Na_v1.7$ and $Na_v1.8$. Typically, treatment or prevention of such diseases and disorders can be effected by selectively modulating voltage-gated sodium channels, e.g., $Na_v1.7$ and $Na_v1.8$, in a mammal, by administering a compound or composition of the invention, either alone or in combination with another active agent as part of a therapeutic regimen.

The terms "treat," "treating," and "treatment" are readily understood by a physician of ordinary skill and, with respect to treatment of a particular condition, can include ameliorating, suppressing, eradicating, preventing, reducing the risk of, and/or delaying the onset of the disease being treated.

The term "subject" includes animals such as mammals, including primates (e.g., humans), cows, sheep, goats, horses, dogs, cats, rabbits, rats, mice and the like. The methods of treatment are particularly suitable for use with a human subject, but may be used with other animal subjects, particularly mammals.

One embodiment of the present invention provides a method of treating pain in a subject in need thereof. The method comprises administering to the subject, including a mammal, such as a human, a therapeutically effective amount of a compound of formula (I), or a pharmaceutically acceptable salt thereof. Conditions related to pain include, for example, acute pain, chronic pain, neuropathic pain, nociceptive pain, allodynia, inflammatory pain, inflammatory hyperalgesia, post herpetic neuralgia, post-operative pain, post-stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, knee pain, fibromyalgia, neuritis, sciatica, pelvic hypersensitivity, pelvic pain, menstrual pain.

Pain generally can be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain include neuropathic pain (e.g., painful diabetic neuropathy, postherpetic neuralgia), carpal tunnel syndrome, back pain, headache, cancer pain, arthritic pain and chronic post-surgical pain. In one embodiment, the condition related to pain is chronic pain. In another embodiment, the condition related to pain is acute pain.

Pain also can be divided into a number of different subtypes according to differing pathophysiology, including neuropathic, nociceptive, and inflammatory pain. Some types of pain have multiple etiologies and can be classified in more than one area, e.g., back pain and cancer pain have both nociceptive and neuropathic components.

In one embodiment, the condition related to pain is selected from the group consisting of neuropathic pain, nociceptive pain, and inflammatory pain.

In another embodiment, the condition related to pain is neuropathic pain. Neuropathic pain generally is defined as pain initiated or caused by a primary lesion or dysfunction in the nervous system and can result, for example, from trauma or disease. The term neuropathic pain encompasses many conditions with diverse etiologies including peripheral neuropathy, diabetic neuropathy, post-herpetic neuralgia, trigeminal neuralgia, back pain, cancer neuropathy, HIV-neuropathy, phantom limb pain, carpal tunnel syndrome, central post-stroke pain, and pain associated with chronic alcoholism, hypothyroidism, uremia, multiple sclerosis, spinal cord injury, Parkinson's disease, epilepsy and vitamin deficiency.

In another embodiment, the condition related to pain is nociceptive pain. Nociceptive pain is induced by tissue injury or by intense stimuli with the potential to cause injury. When a substantial injury occurs to body tissue through trauma or disease, the characteristics of nociceptor activation are altered and there is sensitization in the periphery leading to a heightened sensation of pain in the subject. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e. g., bone pain, headache, facial pain or visceral pain) or pain associated with cancer therapy (e.g., post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament.

In another embodiment, the condition related to pain is inflammatory pain. A common type of inflammatory pain is arthritic pain arising from rheumatoid disease (such as ankylosing spondylitis) or symptomatic osteoarthritis or degenerative joint disease. Another type of inflammatory pain is visceral pain. Visceral pain is pain associated with the viscera, which encompass the organs of the abdominal cavity including the sex organs, spleen and part of the digestive system. Pain associated with the viscera can be divided into digestive visceral pain and non-digestive visceral pain. Commonly encountered gastrointestinal disorders that cause pain include functional bowel disorder and inflammatory bowel disease. These gastrointestinal disorders include a wide range of disease states that are currently only moderately controlled, including, with respect to functional bowel disorder, gastro-esophageal reflux, dyspepsia, irritable bowel syndrome, and functional abdominal pain syndrome, and, in respect of inflammatory bowel disease, Crohn's disease, ileitis and ulcerative colitis, all of which regularly produce visceral pain. Other types of visceral pain include the pain associated with dysmenorrhea, cystitis and pancreatitis and pelvic pain.

In another embodiment, the condition related to pain results from a musculo-skeletal condition such as myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome, temporomandibular myofascial pain, and paroxysmal extreme pain disorder (PEPD); and inherited erythromelalgia (IEM).

In some embodiments, the methods comprise combination therapy, wherein the compound(s) and/or salt(s) of the invention is/are co-administered with a second (or even a third, fourth, etc.) compound, such as, for example, another therapeutic agent used to treat pain. The compound(s) and/or salt(s) of this invention can also be co-administered with therapeutic agents other than therapeutic agents used to treat pain. In these co-administration embodiments, the compound(s) and/or salt(s) of the invention and the second, etc. therapeutic agent(s) may be administered in a substantially simultaneous manner (e.g., or within about five minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

In certain embodiments, the method comprises co-administering to the subject the compound(s) and/or salt(s) of the invention with one or more compounds selected from the group consisting of nonsteroidal anti-inflammatory drugs (NSAIDs), opioid analgesics, barbiturates, benzodiazapines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, $5\text{-HT}_{2A}$ receptor antagonists, cholinergic analgesics, $\alpha_2\delta$ ligands (such as gabapentin or pregabalin), cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-$HT_3$ antagonists, N-methyl-D-aspartic acid receptor antagonists, phosphodiesterase V inhibitors, voltage-gated calcium channel blockers (e.g., N-type and T-type), and KCNQ openers (e.g., KCNQ2/3 ($K_v$7.2/3)).

In one embodiment, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, NSAIDs, opioid analgesics, and combinations thereof.

In one embodiment, the method comprises administering to the subject a therapeutically effective amount of a compound described herein, or a pharmaceutically acceptable salt, with or without a pharmaceutically acceptable carrier, in combination with one or more additional therapeutic agents for treating pain. In one embodiment, the additional therapeutic agent is selected from the group consisting of acetaminophen, NSAIDs (such aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

The present invention also is directed, in part, to one or more compounds and/or salts of the invention for use in the treatment of a voltage-gated sodium channel-mediated condition, such as pain.

The present invention also is directed, in part, to one or more compounds and/or salts of the invention, and, optionally one or more additional therapeutic agents, for use as a medicament. In some embodiments, the medicament is for treating pain. In another embodiment, the medicament is for treating neuropathic pain. In another embodiment, the medicament is for treating nociceptive pain. In another embodiment, the medicament is for treating inflammatory pain.

The present invention is further directed, in part, to a use of one or more compounds and/or salts of the invention, and, optionally one or more additional therapeutic agents to prepare a medicament. In some embodiments, the medicament is for co-administration with one or more additional therapeutic agents. In some embodiments, the medicament is for treating pain. In some embodiments, the medicament is for treating neuropathic pain. In some embodiments, the medicament is for treating nociceptive pain. In some embodiments, the medicament is for treating inflammatory pain.

Compounds of the invention are particularly useful for treating and preventing a condition or disorder affecting pain.

The ability of the compounds of the invention, including, but not limited to, those specified in the examples, to treat the pain of peripheral neuropathy may be demonstrated by Faber C G, et al. Ann Neurol 2012; 72:26-39; Faber C G, et al. Proc. Natl. Acad. Sci. U.S.A. 2012; 109:19444-19449.

The ability of the compounds of the invention, including, but not limited to, those specified in the examples, to treat inflammatory and neuropathic pain may be demonstrated by McGowan E, et al. Anesth. Analg. 2009; 109:951-958.

The ability of the compounds of the invention, including, but not limited to, those specified in the examples, to treat chronic inflammatory knee pain may be demonstrated by Strickland I T, et al. European Journal of Pain 2008; 12:564-572.

The ability of the compounds of the invention, including, but not limited to, those specified in the examples, to treat osteoarthitis may be demonstrated by Schuelert N, et al. Arthritis Research & Therapy 2012; 14:R5; Malfait, A-M, et al. Nat. Rev. Rheumatol. 2013; 9:654-664; and Staunton C A, et al. Current Pain and Headache Reports 2013; 17:378.

The ability of the compounds of the invention, including, but not limited to, those specified in the examples, to treat osteoarthitis and sciatic pain may be demonstrated by Reimann F, et al. Proceedings of the National Academy of Sciences of the United States of America 2010; 107:5148-5153.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 100 mg/kg/day. For purposes of oral administration, more preferable doses can be in the range of from about 0.0003 to about 30 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Abbreviations: APCI for atmospheric pressure chemical ionization; DCI for desorption chemical ionization; DMSO for dimethyl sulfoxide; ESI for electrospray ionization; HPLC for high performance liquid chromatography; psi for pounds per square inch; and SFC for super critical fluid chromatography.

Example 1

(3aR,6aR)-5-[1-(2-fluorophenyl)-1H-indazol-4-yl]-1-(3-hydroxy-3-methylbutanoyl)hexahydropyrrolo[3,4-b]pyrrol-6(1H)-one Example 1A N-benzylbut-3-en-1-amine To a 1000 mL round bottom flask was added 3-buten-1-ol (59.5 mL, 693 mmol) in $CH_2Cl_2$ (1000 mL), and the mixture was cooled to −4° C. Triethylamine (97 mL, 693 mmol) was added followed by dropwise addition of methanesulfonyl chloride (53.8 mL, 693 mmol). The mixture was stirred for 1 h and was then quenched with 1 N HCl (200 mL). The layers were separated, and the organic layer was washed with saturated, aqueous $NaHCO_3$ (200 mL) and brine (200 mL), dried over anhydrous $Na_2SO_4$, filtered and concentrated in vacuo to give the intermediate but-3-en-1-yl methanesulfonate (96 g, 639 mmol, 92% yield).

To a 100 mL round bottom flask containing but-3-en-1-yl methanesulfonate (6.14 g, 40.9 mmol) was added acetonitrile (30 mL) and benzylamine (17.8 mL, 164 mmol). The reaction mixture was heated to 85° C. and was stirred for 16 h. The reaction mixture was allowed to cool to ambient temperature and was diluted with methyl tert-butyl ether (MTBE) (300 mL), washed with 2 N NaOH (50 mL), dried over anhydrous $Na_2SO_4$, filtered and concentrated in vacuo. The residue was purified via column chromatography ($SiO_2$, heptane/ethyl acetate 0-50% over 50 minutes) to give the titled compound (4.57 g, 28.3 mmol, 69% yield). $^1$H NMR (500 MHz, DMSO-$d_6$) δ ppm 7.51-7.10 (m, 5H), 5.81 (ddt, J=17.0, 10.2, 6.8 Hz, 1H), 5.08-4.92 (m, 2H), 3.81 (s, 2H), 3.28-3.22 (bs, 1H), 2.80-2.59 (m, 2H), 2.18 (q, J=7.0 Hz, 2H); MS (DCI) m/z 162 [M+H]$^+$.

Example 1B methyl 2-(benzyl(but-3-en-1-yl)amino)acetate

To a 10 mL round bottom flask was added the product of Example 1A (3.57 g, 22.1 mmol), dimethyl sulfoxide (30 mL) and triethylamine (3.70 mL, 26.6 mmol). Methyl bromoacetate (2.3 mL, 24 mmol) was added dropwise, and the reaction mixture was allowed to stir for 1 h. The mixture was poured into ethyl acetate (50 mL), washed with water (50 mL) and brine (50 mL), dried over anhydrous $Na_2SO_4$, filtered and concentrated in vacuo. The crude material was purified via column chromatography ($SiO_2$, heptane/ethyl acetate 0-10% gradient over 60 minutes) to give the titled compound (4.33 g, 18.6 mmol, 84% yield). $^1$H NMR (500 MHz, DMSO-$d_6$) δ ppm 7.51-7.10 (m, 5H), 5.81 (ddt, J=17.0, 10.2, 6.8 Hz, 1H), 5.08-4.92 (m, 2H), 4.03 (q, J=7.1 Hz, 1H), 3.81 (s, 1H), 3.24 (dd, J=195.9, 87.8 Hz, 1H), 2.85 (d, J=10.3 Hz, 1H), 2.80-2.59 (m, 1H), 2.45-2.25 (m, 2H), 2.18 (q, J=7.0 Hz, 2H), 2.13-1.74 (m, 2H); MS (DCI) m/z 234 [M+H]$^+$.

Example 1C rel-(2R,3S)-methyl 1-benzyl-3-(iodomethyl)pyrrolidine-2-carboxylate

To the product of Example 1B (2.12 g, 9.09 mmol) in diethyl ether (40 mL) at −78° C. was added lithium diisopropylamide (2.0 M in tetrahydrofuran/heptane/ethylbenzene, 5.0 mL, 10.0 mmol) dropwise with the reaction mixture temperature being maintained below −74° C. After the addition was complete, the reaction mixture was stirred for 5 minutes, and then the reaction mixture was cooled to −90° C. (acetone/liquid $N_2$) and zinc bromide (6.14 g, 27.3 mmol) in diethyl ether (50 mL) was added at a rate to maintain the reaction temperature below −64° C. After the addition was complete, the reaction mixture was allowed to warm to ambient temperature (~15 minutes) and was stirred for 20 minutes. The reaction mixture was cooled to 0° C. and iodine (2.54 g, 10.0 mmol) in diethyl ether (5 mL) was added, and the reaction mixture was allowed to warm to ambient temperature. After 30 minutes, the mixture was poured into a separatory funnel, diluted with ether (50 mL), washed with saturated aqueous $Na_2S_2O_3$ (50 mL) and saturated, aqueous $NH_4Cl$ (50 mL). The organic layer was dried over anhydrous $Na_2SO_4$, filtered and concentrated in vacuo to give the titled compound (2.68 g, 7.46 mmol, 82% yield). $^1$H NMR (500 MHz, DMSO-$d_6$) δ ppm 7.51-7.10 (m, 5H), 3.81 (s, 1H), 3.65-3.45 (m, 3H), 3.24 (dd, J=195.9, 87.8 Hz, 1H), 2.85 (d, J=10.3 Hz, 1H), 2.80-2.59 (m, 1H), 2.45-2.25 (m, 1H), 2.18 (q, J=7.0 Hz, 2H), 2.13-1.74 (m, 1H), 1.32-1.07 (m, 1H), 0.86 (t, J=7.0 Hz, 1H); MS (DCI) m/z 360 [M+H]$^+$.

Example 1D rel-(2R,3R)-methyl 3-(azidomethyl)-1-benzylpyrrolidine-2-carboxylate

To the product of Example 1C (4.48 g, 12.47 mmol) in N,N-dimethylformamide (20 mL) was added sodium azide (1.22 g, 18.7 mmol). The reaction mixture was warmed to 50° C. and was allowed to stir for 1 h. The reaction mixture was allowed to cool to ambient temperature, was diluted with ethyl acetate (100 mL), and transferred to a separatory funnel. The organic solution was washed with brine (20 mL), and the organic layer was dried over anhydrous $Na_2SO_4$, filtered and concentrated in vacuo. The residue was purified via column chromatography ($SiO_2$, 0-20% heptane/ethyl acetate over 60 minutes with 60 minute hold) to give the titled compound (2.31 g, 8.38 mmol, 67% yield). $^1$H NMR (500 MHz, DMSO-$d_6$) δ ppm 7.51-7.10 (m, 5H), 5.81 (ddt, J=17.0, 10.2, 6.8 Hz, 1H), 4.16 (s, 1H), 4.03 (q, J=7.1 Hz, 1H), 3.81 (s, 1H), 3.24 (dd, J=195.9, 87.8 Hz, 1H), 2.85 (d, J=10.3 Hz, 1H), 2.80-2.59 (m, 2H), 2.45-2.25 (m, 1H), 2.18 (q, J=7.0 Hz, 2H), 2.13-1.74 (m, 1H), 1.32-1.07 (m, 1H), 0.86 (t, J=7.0 Hz, 1H); MS (DCI) m/z 275 [M+H]$^+$.

Example 1E rel-(3aR,6aR)-1-benzylhexahydropyrrolo[3,4-b]pyrrol-6(1H)-one

To the product of Example 1D (2.31 g, 8.42 mmol) in 2-methyltetrahydrofuran (12 mL) and water (12 mL) was added triphenylphosphine (3.31 g, 12.6 mmol). The reaction mixture was warmed to 74° C. and was allowed to stir for 90 minutes, and then the mixture was allowed to cool to ambient temperature and was diluted with ethyl acetate (80 mL). The layers were separated, and the organic layer was dried over anhydrous $Na_2SO_4$, filtered and concentrated in vacuo. The residue was purified via column chromatography ($SiO_2$, 0-100% ethyl acetate/heptane over 30 minutes with 60 minute hold) to give the titled compound (1.70 g, 7.86 mmol, 93% yield). $^1$H NMR (400 MHz, DMSO-$d_6$) δ ppm 7.49-7.06 (m, 5H), 4.56 (d, J=15.3 Hz, 1H), 4.29 (ddd, J=44.5, 20.5, 10.2 Hz, 1H), 4.19-3.92 (m, 1H), 3.88-3.71 (m, 1H), 3.61 (d, J=13.3 Hz, 1H), 3.54-3.42 (m, 1H), 3.26-3.00 (m, 1H), 2.78-2.59 (m, 1H), 2.31 (td, J=8.8, 6.6 Hz, 1H), 2.22-1.95 (m, 1H), 1.61-1.44 (m, 1H); MS (DCI) m/z 217 $[M+H]^+$.

Example 1F rel-(3aR,6aR)-1-benzyl-5-[1-(2-fluorophenyl)-1H-indazol-4-yl]hexahydropyrrolo[3,4-b]pyrrol-6(1H)-one The product of Example 9C (2.29 g, 7.86 mmol), the product of Example 1E (1.70 g, 7.86 mmol), copper(I) iodide (74.8 mg, 0.39 mmol) and potassium phosphate tribasic (3.50 g, 16.5 mmol) was degassed three times with a nitrogen backflush each time. Trans-N,N'-dimethylcyclohexane-1,2-diamine (0.25 mL, 1.6 mmol) and dioxane (50 mL) were added. The mixture was warmed to 110° C. and was allowed to stir for 16 h. Additional copper(I) iodide (74.8 mg, 0.393 mmol) and trans-N,N'-di methylcyclohexane-1,2-diamine (0.25 mL, 1.6 mmol) were added, and the mixture was warmed to 110° C. and stirred for an additional 8 h. The reaction mixture was allowed to cool to ambient temperature and was then filtered through diatomaceous earth with ethyl acetate washing. The filtrate was concentrated under reduced pressure, and the residue was purified via column chromatography ($SiO_2$, 5% ethyl acetate/hexanes to 65% ethyl acetate/hexanes) to give the titled compound (2.96 g, 6.94 mmol, 88% yield). $^1$H NMR (400 MHz, CDCl$_3$) δ ppm 8.32 (d, J=0.7 Hz, 1H), 7.35-6.95 (m, 11H), 4.42 (d, J=13.1 Hz, 1H), 4.13 (ddd, J=21.4, 11.9, 7.8 Hz, 1H), 3.89-3.53 (m, 2H), 3.10-2.84 (m, 1H), 2.56 (dd, J=16.1, 8.2 Hz, 1H), 2.22 (tdd, J=10.8, 6.2, 3.5 Hz, 1H), 2.03 (d, J=9.0 Hz, 1H), 1.88-1.70 (m, 1H), 1.41-1.19 (m, 1H), 1.01-0.70 (m, 1H); MS (ESI+) m/z 427 $[M+H]^+$.

Example 1G rel-(3aR,6aR)-5-[1-(2-fluorophenyl)-1H-indazol-4-yl]hexahydropyrrolo[3,4-b]pyrrol-6(1H)-one To a stainless steel hydrogenation vessel at ambient temperature was added the product of Example 1F (2.96 g, 6.94 mmol) and tetrahydrofuran (30 mL). To this solution was added 20% Pd(OH)$_2$/C (wet; 0.6 g, 0.4 mmol), and the reaction mixture was placed under 30 psi hydrogen for 16 h. The mixture was filtered and concentrated in vacuo to give the titled compound (2.32 g, 6.90 mmol, 99% yield). The crude material was carried on without purification. $^1$H NMR (400 MHz, DMSO-$d_6$) δ ppm 8.25 (s, 1H), 7.73-7.40 (m, 6H), 7.25 (dd, J=6.3, 4.2 Hz, 2H), 4.31-4.18 (m, 1H), 4.01 (dt, J=22.3, 7.7 Hz, 1H), 3.66 (dd, J=9.9, 2.7 Hz, 1H), 3.02-2.89 (m, 1H), 2.79 (ddd, J=10.1, 8.3, 1.7 Hz, 1H), 2.10-1.95 (m, 1H), 1.84-1.71 (m, 1H), 1.18 (t, J=7.1 Hz, 1H); MS (DCI) m/z 337 $[M+H]^+$.

Example 1H (3aR,6aR)-5-[1-(2-fluorophenyl)-1H-indazol-4-yl]-1-(3-hydroxy-3-methylbutanoyl)hexahydropyrrolo[3,4-b]pyrrol-6(1H)-one To the product of Example 1G (312 mg, 0.928 mmol) in N,N-dimethylformamide (10 mL) was added 3-hydroxy-3-methylbutanoic acid (110 mg, 0.928 mmol), triethylamine (0.129 mL, 0.928 mmol) and (dimethylamino)-N,N-dimethyl(3-oxido-1H-[1,2,3]triazolo[4,5-b]pyridin-1-yl)methaniminium hexafluorophosphate (HATU, 353 mg, 0.928 mmol). The mixture was stirred at ambient temperature for 20 minutes and then was poured into ethyl acetate (50 mL) in a separatory funnel. The mixture was washed with water (25 mL) and brine (25 mL), dried over anhydrous $Na_2SO_4$, filtered and concentrated under reduced pressure. The residue was purified via column chromatography ($SiO_2$, eluted with heptane/ethyl acetate-100% over 30 minutes with 60 minute hold) to provide a racemic mixture of the titled compound. The enantiomers were separated by supercritical fluid chromatography (SFC) using a Chiracel® OD-H column eluted at 80 mL/minute with methanol/$CO_2$ to give the pure enantiomers with the first eluting compound being the titled compound (26 mg, 0.06 mmol, 27% yield). $^1$H NMR (500 MHz, DMSO-$d_6$) δ ppm 8.35 (d, J=0.8 Hz, 1H), 7.70 (dt, J=5.9, 2.9 Hz, 1H), 7.64-7.41 (m, 5H), 7.37-7.27 (m, 2H), 5.16 (dd, J=37.6, 8.1 Hz, 1H), 4.31 (dt, J=13.4, 4.9 Hz, 1H), 3.79-3.67 (m, 1H), 3.58-3.47 (m, 1H), 3.28-3.14 (m, 1H), 3.10-3.00 (m, 1H), 2.82 (d, J=15.0 Hz, 1H), 2.71 (d, J=15.0 Hz, 1H), 2.29 (dddd, J=15.0, 11.6, 9.8, 5.7 Hz, 1H), 1.99-1.77 (m, 1H), 1.22 (t, J=9.7 Hz, 6H); MS (DCI) m/z 437 $[M+H]^+$.

Alternative Preparation of Example 1

Example 1I but-3-en-1-yl methanesulfonate

To a 2 L round bottom flask was added 3-buten-1-ol (59.5 mL, 693 mmol) in $CH_2Cl_2$ (800 mL), and the mixture was cooled to 4° C. with an ice-bath. Triethylamine (97 mL, 690 mmol) was added slowly over 5 minutes followed by dropwise addition of methanesulfonyl chloride (53.8 mL, 693 mmol). An 8° C. to 9° C. exothermic reaction was observed. The reaction mixture was stirred for 60 minutes with an internal temperature maintained between 4-8° C. The reaction mixture was combined with 1 N HCl (200 mL), and the layers were separated. The organic layer was washed with saturated, aqueous $NaHCO_3$ (200 mL) and brine (200 mL), then was dried over anhydrous $Na_2SO_4$, filtered and concentrated in vacuo to give the titled compound (96 g, 639 mmol, 92% yield) which was used without further purification. $^1$H NMR (400 MHz, DMSO-$d_6$) δ ppm 5.80 (ddt, J=17.0, 10.3, 6.6 Hz, 1H), 5.26-5.04 (m, 2H), 4.24 (t, J=6.5 Hz, 2H), 3.15 (s, 4H), 2.44 (qt, J=6.5, 1.5 Hz, 3H); MS (DCI) m/z 151 $[M+H]^+$.

Example 1J

N-[(1R)-1-phenylethyl]but-3-en-1-amine

A mixture of (1R)-1-phenylethanamine (45.1 mL, 350 mmol) and the product of Example 1I (35 g, 233 mmol) in acetonitrile (100 mL) was heated at 85° C. for 18 hours. The reaction was allowed to cool to ambient temperature and was partitioned between methyl tert-butyl ether and 2 N NaOH. The organic phase was dried over anhydrous $Na_2SO_4$, filtered and concentrated under reduced pressure. The residue was purified by column chromatography ($SiO_2$, 25% ethyl acetate in heptanes) to afford the titled compound (24 g, 137 mmol, 59% yield). $^1$H NMR (500 MHz, $CDCl_3$) δ ppm 7.35-7.28 (m, 4H), 7.27-7.20 (m, 1H), 5.74 (ddt, J=17.1, 10.1, 6.8 Hz, 1H), 5.07 (dq, J=17.2, 1.6 Hz, 1H), 5.04-4.99 (m, 1H), 3.76 (q, J=6.6 Hz, 1H), 2.57 (dt, J=11.4, 6.8 Hz, 1H), 2.50 (dt, J=11.4, 6.9 Hz, 1H), 2.30-2.13 (m, 2H), 1.35 (d, J=6.6 Hz, 3H); MS (DCI) m/z 176 $[M+H]^+$.

Example 1K methyl N-but-3-en-1-yl-N-[(1R)-1-phenylethyl] glycinate

Methyl bromoacetate (13.05 mL, 137 mmol) was added to a mixture of the product of Example 1J (20.0 g, 114 mmol) and N-ethyl-N-isopropylpropan-2-amine (39.9 mL, 228 mmol) in dimethyl sulfoxide (100 mL). The mixture was stirred at ambient temperature for 2 hours, and then it was partitioned between 10% $NaHCO_3$ (50 mL) and ethyl acetate (100 mL). The layers were separated, and the organic layer was washed with brine (30 mL), dried over anhydrous $MgSO_4$, filtered and concentrated under reduced pressure. The residue was purified by column chromatography ($SiO_2$, 5% ethyl acetate in heptanes) to afford the titled compound (26 g, 105 mmol, 92% yield). $^1$H NMR (400 MHz, $CDCl_3$) δ ppm 7.41-7.15 (m, 5H), 5.75 (ddt, J=17.0, 10.2, 6.8 Hz, 1H), 5.01 (dq, J=17.3, 1.6 Hz, 1H), 4.98-4.93 (m, 1H), 4.03 (q, J=6.7 Hz, 1H), 3.66 (s, 3H), 3.45 (d, J=17.3 Hz, 1H), 3.30 (d, J=17.3 Hz, 1H), 2.77-2.59 (m, 2H), 2.25-2.11 (m, 2H), 1.35 (d, J=6.7 Hz, 3H); MS ($ESI^+$) m/z 248 $(M+H)^+$.

Example 1L methyl (3S)-3-(iodomethyl)-1-[(1R)-1-phenylethyl]-D-prolinate

The product of Example 1K (4.7 g, 19.0 mmol) in diethyl ether (200 mL) was cooled to −78° C. Lithium diisopropylamide (2 M in tetrahydrofuran/heptane/ethylbenzene, 14.3 mL, 28.5 mmol) was added dropwise, and the reaction was allowed to warm to 0° C. and was stirred for 20 minutes. The reaction mixture was then cooled to −78° C., and anhydrous zinc(II) bromide (8.6 g, 38.0 mmol) in diethyl ether (20 mL) was added dropwise over 30 minutes. The cooling bath was removed, and the reaction was allowed to warm to 20° C. The mixture was then cooled to 0° C., and iodine (5.3 g, 20.9 mmol) in 30 mL of diethyl ether was added portionwise. After the addition was complete, the cooling bath was removed, and the reaction was allowed to warm to ambient temperature and was stirred for 1 hour. Saturated, aqueous $Na_2S_2O_3$ was added followed by saturated, aqueous $NH_4Cl$. The phases were separated, and the aqueous phase was extracted with diethyl ether (2×20 mL). The combined organic layers were washed with brine (30 mL), dried over anhydrous $MgSO_4$, filtered and concentrated under reduced pressure. The residue was purified by column chromatography ($SiO_2$, 5% ethyl acetate in heptanes) to afford predominantly the titled compound (4.9 g, 13.13 mmol, 69.1% yield); MS (APCI) m/z 374 $[M+H]^+$.

Example 1M methyl (3R)-3-(azidomethyl)-1-[(1R)-1-phenylethyl]-D-prolinate

The product of Example 1L (4.9 g, 13.1 mmol) and sodium azide (1.3 g, 19.7 mmol) in dimethylformamide (20 mL) was heated at 50° C. for 4 hours. The reaction mixture was allowed to cool to ambient temperature and was diluted with ethyl acetate (50 mL). The layers were separated, and the organic layer was washed with brine (20 mL), dried over anhydrous $MgSO_4$, filtered and concentrated under reduced pressure. The residue was purified by column chromatography ($SiO_2$, 20% ethyl acetate in heptanes) to afford predominantly the titled compound (2.6 g, 9.02 mmol, 69% yield). $^1$H NMR (500 MHz, methanol-$d_4$) δ ppm 7.32-7.20 (m, 5H), 3.71 (q, J=6.7 Hz, 1H), 3.64 (s, 3H), 3.39 (d, J=8.1 Hz, 1H), 3.29-3.19 (m, 2H), 3.02 (td, J=9.0, 3.2 Hz, 1H), 2.92-2.84 (m, 1H), 2.62-2.49 (m, 1H), 2.05-1.96 (m, 1H), 1.73-1.58 (m, 1H), 1.34 (d, J=6.7 Hz, 3H); MS ($ESI^+$) m/z 289 $[M+H]^+$.

Example 1N tert-butyl (3aR,6aR)-6-oxo-1-[(1R)-1-phenylethyl] hexahydropyrrolo[3,4-b]pyrrole-5(1H)-carboxylate To the product of Example 1M (5.0 g, 17.34 mmol) was added triphenylphosphine (5.00 g, 19.07 mmol) in tetrahydrofuran (40 mL) followed by water (40 mL). The reaction was warmed to 70° C. and was allowed to stir for 1 hour. The mixture was then allowed to cool to ambient temperature and was diluted with ethyl acetate (75 mL). The layers were separated, and the organic layer was washed with brine (25 mL), dried over anhydrous $MgSO_4$, filtered and concentrated under reduced pressure. Di-tert-butyl dicarbonate (4.2 g, 19.11 mmol) and N,N-dimethylpyridin-4-amine (0.21 g, 1.74 mmol) were added to the residue in acetonitrile (25 mL), and the mixture was stirred at ambient temperature for 3 hours. The reaction was concentrated under reduced pressure, and the residue was partitioned between ethyl acetate (50 mL) and 10% $NaHCO_3$ (aqueous) (50 mL). The layers were separated, and the organic layer was washed with brine (30 mL), dried over anhydrous $MgSO_4$, filtered and concentrated under reduced pressure. The residue was purified by column chromatography ($SiO_2$, 10% ethyl acetate in heptanes for 3 column volumes followed by a gradient to 40% ethyl acetate in heptanes and held for 4 column volumes) to afford the titled compound as the major isomer (5.0 g, 15.1 mmol, 87% yield). $^1$H NMR (400 MHz, methanol-$d_4$) δ ppm 7.41-7.34 (m, 2H), 7.33-7.27 (m, 2H), 7.26-7.17 (m, 1H), 4.02 (q, J=6.8 Hz, 1H), 3.76 (dd, J=11.0, 7.7 Hz, 1H), 3.57 (d, J=9.2 Hz, 1H), 3.53 (dd, J=11.1, 2.2 Hz, 1H), 2.78 (ddd, J=9.7, 6.9, 3.0 Hz, 1H), 2.75-2.63 (m, 1H), 2.53 (td, J=9.4, 6.2 Hz, 1H), 2.13-2.00 (m, 1H), 1.62-1.53 (m, 1H), 1.52 (s, 9H), 1.48 (d, J=6.8 Hz, 3H); MS (ESI+) m/z 331 $[M+H]^+$. The minor isomer, tert-butyl (3aS,6aS)-6-oxo-1-[(1R)-1-phenylethyl]hexahydropyrrolo[3,4-b] pyrrole-5(1H)-carboxylate, was also isolated (0.25 g, 0.76 mmol, 4.4% yield). $^1$H NMR (400 MHz, methanol-$d_4$) δ ppm 7.40-7.34 (m, 2H), 7.32-7.26 (m, 2H), 7.24-7.18 (m, 1H), 4.16 (q, J=6.6 Hz, 1H), 3.96 (d, J=8.5 Hz, 1H), 3.78 (dd, J=11.1, 7.4 Hz, 1H), 3.53 (dd, J=11.1, 1.8 Hz, 1H), 2.81-2.70 (m, 1H), 2.70-2.62 (m, 1H), 2.62-2.53 (m, 1H), 2.16-2.04 (m, 1H), 1.56 (dt, J=13.0, 6.6 Hz, 1H), 1.51 (s, 9H), 1.49 (d, J=6.6 Hz, 3H); MS (ESI⁺) m/z 331 [M+H]⁺.

Example 10

(3aR,6aR)-1-[(1R)-1-phenylethyl]hexahydropyrrolo [3,4-b]pyrrol-6(1H)-one

To the product of Example 1N (5.0 g, 15.13 mmol) in dichloromethane (10 mL) was added trifluoroacetic acid (10 mL). The reaction was allowed to stir for 1 hour and then was concentrated under reduced pressure. The residue was partitioned between ethyl acetate (10 mL) and saturated, aqueous NaHCO₃ (10 mL). The layers were separated, and the organic layer was washed with water (10 mL) and brine (10 mL), dried over anhydrous MgSO₄, filtered and concentrated under reduced pressure to give the crude titled compound (4 g, 17.4 mmol, >100% yield) which was used without further purification. MS (APCI) m/z 231 [M+H]⁺.

Example 1P (3aR,6aR)-hexahydropyrrolo[3,4-b]pyrrol-6(1H)-one

To the product of Example 1O (7.53 g, 32.7 mmol) in ethanol (80 mL) was added to 20% Pd(OH)₂ on carbon, wet (1.62 g, 11.54 mmol) in a 250 mL stainless steel pressure bottle. The mixture was stirred under 30 psi of hydrogen at 50° C. for 8 hours. The mixture was filtered through a nylon membrane, and the solvent was removed under reduced pressure to give the titled compound (4 g, 31.7 mmol, 97% yield). ¹H NMR (400 MHz, methanol-d₄) δ ppm 4.01 (d, J=8.5 Hz, 1H), 3.63 (dd, J=10.6, 7.7 Hz, 1H), 3.16 (dd, J=10.6, 2.2 Hz, 1H), 3.14-3.07 (m, 1H), 3.07-3.01 (m, 1H), 2.99-2.91 (m, 1H), 2.23-2.13 (m, 1H), 1.79-1.70 (m, 1H); MS (ESI⁺) m/z 253 [2M+H]⁺.

Example 1Q (3aR,6aR)-5-[1-(2-fluorophenyl)-1H-indazol-4-yl] hexahydropyrrolo[3,4-b]pyrrol-6(1H)-one The product of Example 1P (0.433 g, 3.44 mmol), finely ground potassium phosphate tribasic (1.53 g, 7.21 mmol), the product of Example 9C (1.0 g, 3.44 mmol), copper (I) iodide (0.033 g, 0.172 mmol) and trans-N,N'-dimethylcyclohexane-1,2-diamine (0.108 mL, 0.687 mmol) were combined in 1,4-dioxane (15 mL) under nitrogen in a pressure tube. The tube was sealed, back-flushed with nitrogen and heated at 110° C. for 1 hour. Additional copper(I) iodide (0.033 g, 0.172 mmol) and trans-N,N'-dimethylcyclohexane-1,2-diamine (0.108 mL, 0.687 mmol) in 1,4-dioxane (1.5 mL) were added, and the reaction was continued for 20 hours at 110° C. The mixture was allowed to cool to ambient temperature and then was diluted with ethyl acetate (20 mL). The mixture was filtered through diatomaceous earth, and the filtrate was concentrated under reduced pressure. The residue was purified by column chromatography (SiO₂, 100% ethyl acetate to 50% methanol in ethyl acetate) to afford the titled compound (0.6 g, 1.8 mmol, 52% yield). ¹H NMR (400 MHz, methanol-d₄) δ ppm 8.31 (s, 1H), 7.61 (td, J=7.7, 1.6 Hz, 1H), 7.59-7.52 (m, 1H), 7.51-7.46 (m, 1H), 7.45-7.38 (m, 2H), 7.27 (dd, J=8.4, 2.9 Hz, 1H), 7.21 (d, J=7.4 Hz, 1H), 4.35 (dd, J=10.1, 7.9 Hz, 1H), 4.13 (d, J=8.5 Hz, 1H), 3.72 (dd, J=10.2, 2.4 Hz, 1H), 3.17-3.04 (m, 2H), 2.99-2.90 (m, 1H), 2.26-2.14 (m, 1H), 1.91-1.81 (m, 1H); MS (APCI) m/z 337.1 [M+H]⁺.

Example 1R (3aR,6aR)-5-[1-(2-fluorophenyl)-1H-indazol-4-yl]-1-(3-hydroxy-3-methylbutanoyl)hexahydropyrrolo [3,4-b]pyrrol-6(1H)-one To 3-hydroxy-3-methylbutanoic acid (0.287 mL, 2.68 mmol), the product of Example 1Q (0.6 g, 1.784 mmol) and triethylamine (0.298 mL, 2.141 mmol) in acetonitrile (10 mL) was added (dimethylamino)-N,N-dimethyl(3-oxido-1H-[1,2,3]triazolo[4,5-b]pyridin-1-yl)methaniminium hexafluorophosphate (HATU, 0.814 g, 2.141 mmol). The reaction was allowed to stir for 2 hours, and then the mixture was diluted with ethyl acetate (25 mL). The material was washed with water (20 mL) and brine (20 mL), dried over anhydrous MgSO₄, filtered and concentrated under reduced pressure. The residue was purified by column chromatography (SiO₂, 5% methanol in ethyl acetate) to afford the titled compound (0.70 g, 1.60 mmol, 90% yield). [α]$_D^{20}$ +120° (c 1.0, methanol); ¹H NMR (400 MHz, methanol-d₄) δ ppm 8.27 (dd, J=11.2, 1.0 Hz, 1H), 7.62 (td, J=7.8, 1.7 Hz, 1H), 7.60-7.53 (m, 1H), 7.51 (dd, J=8.5, 7.4 Hz, 1H), 7.46-7.38 (m, 2H), 7.31 (dt, J=8.2, 3.6 Hz, 1H), 7.25 (dd, J=7.5, 6.1 Hz, 1H), 5.20 (dd, J=26.8, 8.1 Hz, 1H), 4.36 (dt, J=10.1, 6.5 Hz, 1H), 3.85-3.60 (m, 3H), 3.20 (q, J=7.3 Hz, 1H), 2.92 (q, J=15.2 Hz, 1H), 2.72-2.54 (m, 1H), 2.51-2.35 (m, 1H), 2.21-1.86 (m, 1H), 1.39-1.28 (m, 7H); MS (ESI⁺) m/z 437 [M+H]⁺.

Example 2

(3aS,6aS)-5-[1-(2-fluorophenyl)-1H-indazol-4-yl]-1-(3-hydroxy-3-methylbutanoyl)hexahydropyrrolo[3, 4-b]pyrrol-6(1H)-one The titled compound was the second eluting isomer from Example 1H (28 mg, 0.064 mmol, 29% yield). ¹H NMR (500 MHz, DMSO-d₆) δ ppm 8.35 (d, J=0.8 Hz, 1H), 7.70 (dt, J=5.9, 2.9 Hz, 1H), 7.64-7.41 (m, 5H), 7.37-7.27 (m, 2H), 5.16 (dd, J=37.6, 8.1 Hz, 1H), 4.31 (dt, J=13.4, 4.9 Hz, 1H), 3.79-3.67 (m, 1H), 3.58-3.47 (m, 1H), 3.28-3.14 (m, 1H), 3.10-3.00 (m, 1H), 2.82 (d, J=15.0 Hz, 1H), 2.71 (d, J=15.0 Hz, 1H), 2.29 (dddd, J=15.0, 11.6, 9.8, 5.7 Hz, 1H), 1.99-1.77 (m, 1H), 1.22 (t, J=9.7 Hz, 6H); MS (DCI) m/z 437 [M+H]⁺.

Alternative Preparation of Example 2

Example 2A

N-[(1 S)-1-phenylethyl]but-3-en-1-amine

To a 500 mL round bottom flask containing the product from Example 1I (50.0 g, 333 mmol) was added acetonitrile (100 mL) and (S)-1-phenylethanamine (64.4 mL, 499 mmol). The reaction was heated to 85° C. and was allowed to stir for 16 hours. The mixture was allowed to cool to ambient temperature and was diluted with tert-butyl methyl ether (300 mL). The layers were separated, and the organic layer was washed with 2 N NaOH (50 mL) and dried over anhydrous Na₂SO₄, filtered and concentrated in vacuo. The residue was purified by column chromatography (SiO₂, eluted with heptane/ethyl acetate 0-50% over 50 minutes) to provide the titled compound (11.94 g, 68.1 mmol, 20% yield). ¹H NMR (500 MHz, CDCl₃) δ ppm 7.41-7.13 (m, 5H), 5.76 (dddt, J=22.0, 17.1, 10.2, 6.8 Hz, 1H), 5.26-4.91 (m, 2H), 2.66-2.42 (m, 2H), 2.32-2.11 (m, 2H), 1.35 (d, J=6.6 Hz, 3H); MS (DCI) m/z 176 [M+H]⁺.

Example 2B methyl N-but-3-en-1-yl-N-[(1S)-1-phenylethyl] glycinate

To a 1 L round bottom flask was added the product from Example 2A (27.4 g, 156 mmol), dimethyl sulfoxide (100 mL) and N,N-diisopropylethylamine (54.1 mL, 312 mmol). Methyl bromoacetate (17.3 mL, 187 mmol) was then added dropwise, and the reaction mixture was allowed to stir for 2 hours. The mixture was poured into ethyl acetate (100 mL) and washed with saturated, aqueous NaHCO₃ (50 mL) and brine (50 mL). The organic layer was dried over anhydrous Na₂SO₄, filtered and concentrated in vacuo. The residue was purified by column chromatography (SiO₂, eluted with heptane/ethyl acetate 0-5% 60 minute gradient) to give the titled compound (32.7 g, 132 mmol, 85% yield). ¹H NMR (400 MHz, CDCl₃) δ ppm 7.46-7.13 (m, 5H), 5.75 (ddt, J=17.0, 10.2, 6.7 Hz, 1H), 5.10-4.87 (m, 2H), 4.03 (q, J=6.8 Hz, 1H), 3.66 (s, 3H), 3.55-3.17 (m, 2H), 2.68 (ddd, J=8.2, 6.9, 1.8 Hz, 2H), 2.19 (dddq, J=8.3, 7.0, 5.5, 1.7 Hz, 2H), 1.35 (d, J=6.7 Hz, 3H); MS (ESI) m/z 248 [M+H]⁺.

Example 2C methyl (3R)-3-(iodomethyl)-1-[(1S)-1-phenylethyl]-L-prolinate

To a 500 mL round bottom flask under nitrogen was added the product of Example 2B (15 g, 61 mmol) and diethyl ether (300 mL), and the solution was cooled to −74° C. (dry ice/acetone). Lithium bis(trimethylsilyl)amide (1 M in tetrahydrofuran, 66.7 mL, 66.7 mmol) was then added dropwise with the internal temperature being maintained below −65° C. After the addition was complete, the reaction was allowed to warm to 0° C. over 25 minutes and then was stirred for an additional 20 minutes at 0° C. (ice/water). The reaction was again cooled to −74° C., and zinc bromide (28.7 g, 127 mmol in diethyl ether 300 mL) was added dropwise over 20-30 minutes, with the internal temperature kept below −60° C. during the addition. The reaction was then allowed to warm to ambient temperature over 30 minutes and was stirred for 10 minutes. The reaction was then cooled to 0° C., and iodine (16.2 g, 63.7 mmol, in 320 mL diethyl ether) was added dropwise with the internal temperature being maintained below 10° C. (25-30 minutes for addition). After the addition was complete, the mixture was allowed to warm to ambient temperature and was stirred for 1 hour. The mixture was diluted with diethyl ether (250 mL) and washed with saturated, aqueous Na₂S₂O₃ (50 mL) and saturated, aqueous NH₄Cl (50 mL). The organic layer was dried over anhydrous Na₂SO₄, filtered and concentrated in vacuo to provide predominantly the titled compound (21.95 g, 58.8 mmol, 96% yield) which was carried on without further purification. ¹H NMR (500 MHz, DMSO-d₆) δ ppm 7.38-7.12 (m, 5H), 3.67-3.54 (m, 4H), 3.37 (d, J=7.6 Hz, 1H), 3.15-2.98 (m, 2H), 2.96-2.86 (m, 2H), 2.65 (dq, J=10.5, 7.8 Hz, 1H), 2.19-2.01 (m, 1H), 1.66-1.47 (m, 1H), 1.23 (d, J=6.6 Hz, 3H); MS (DCI) m/z 374 [M+H]⁺.

Example 2D methyl (3S)-3-(azidomethyl)-1-[(1S)-1-phenylethyl]-L-prolinate

To a 500 mL round bottom flask containing the product from Example 2C (12.0 g, 32.2 mmol) was added N,N-dimethylformamide (120 mL) and sodium azide (4.18 g, 64.3 mmol). The reaction mixture was warmed to 50° C. and was stirred for 2 hours. The mixture was diluted with ethyl acetate (500 mL) and washed with brine (200 mL). The organic layer was dried over anhydrous Na₂SO₄, filtered and concentrated in vacuo to give the titled compound (9.81 g, 34 mmol, >100% yield) which was used without purification. ¹H NMR (500 MHz, CDCl₃) δ ppm 7.42-7.07 (m, 5H), 3.71 (q, J=6.6 Hz, 1H), 3.65 (s, 3H), 3.43 (d, J=8.1 Hz, 1H), 3.33-3.13 (m, 2H), 3.07 (td, J=9.1, 3.3 Hz, 1H), 2.91 (q, J=7.9 Hz, 1H), 2.68-2.48 (m, 1H), 2.03 (dtd, J=11.4, 7.8, 3.2 Hz, 1H), 1.72 (dtd, J=12.4, 9.7, 7.5 Hz, 1H), 1.36 (d, J=6.6 Hz, 3H); MS (DCI) m/z 275 [M+H]⁺.

Example 2E (3aS,6aS)-1-[(1S)-1-phenylethyl]hexahydropyrrolo[3,4-b]pyrrol-6(1H)-one To a 500 mL round bottom flask was added the product from Example 2D (16.7 g, 58.0 mmol), 2-methyl tetrahydrofuran (160 mL) and water (160 mL). Triphenylphosphine (23 g, 87 mmol) was added, and the reaction mixture was warmed to 74° C. and was allowed to stir for 90 minutes. The reaction was allowed to cool to ambient temperature and was transferred to a separatory funnel. The mixture was extracted with ethyl acetate (2×200 mL), dried over anhydrous Na₂SO₄, filtered and concentrated in vacuo. The residue was purified by column chromatography (SiO₂, eluting with 0-100% ethyl acetate/heptane over 30 minutes with a 20 minute hold then ramped to 100% ethyl acetate with 10% methanol) to give the titled compound (9.46 g, 41.1 mmol, 71% yield). ¹H NMR (400 MHz, CDCl₃) δ ppm 7.43-7.17 (m, 5H), 6.10 (s, 1H), 4.15 (dq, J=21.4, 7.0 Hz, 1H), 3.46 (dd, J=9.8, 7.6 Hz, 1H), 3.36 (d, J=8.9 Hz, 1H), 3.12 (ddd, J=9.9, 2.1, 1.1 Hz, 1H), 2.92-2.71 (m, 1H), 2.55 (td, J=9.0, 6.3 Hz, 1H), 2.16-1.98 (m, 1H), 1.65 (ddt, J=12.5, 8.9, 7.2 Hz, 1H), 1.51 (d, J=6.8 Hz, 4H); MS (DCI) m/z 231 [M+H]⁺.

Example 2F tert-butyl (3aS,6aS)-6-oxo-1-[(1S)-1-phenylethyl] hexahydropyrrolo[3,4-b]pyrrole-5(1H)-carboxylate To a 500 mL round bottom flask was added the product from Example 2E (9.46 g, 41.1 mmol), N,N-dimethylformamide (100 mL), di-tert-butyl dicarbonate (10.76 g, 49.3 mmol) and N,N-diisopropylethylamine (14.21 mL, 82 mmol), and the reaction mixture was stirred at ambient temperature. The reaction was proceeding slowly so a catalytic amount of 4-(dimethylamino)pyridine (100 mg) was added, and the reaction was allowed to stir for 16 hours. The mixture was poured into CH₂Cl₂ (200 mL) and was washed with 1 N HCl (20 mL), saturated NaHCO₃ (20 mL) and brine (20 mL). The organic layer was dried over anhydrous Na₂SO₄, filtered and concentrated in vacuo. The residue was purified by column chromatography (SiO$_2$, eluted with cyclohexane/0-20% tetrahydrofuran over 60 minutes with 60 minute hold) to afford the titled compound (9.69 g, 29.3 mmol, 71% yield) and a small amount of the isomer, tert-butyl (3aR,6aR)-6-oxo-1-[(1S)-1-phenylethyl]hexahydropyrrolo[3,4-b]pyrrole-5(1H)-carboxylate, (0.314 g, 1.0 mmol, 2% yield). $^1$H NMR (400 MHz, CDCl$_3$) δ ppm 7.51-6.91 (m, 5H), 4.21 (q, J=6.8 Hz, 1H), 3.71 (dd, J=11.1, 7.8 Hz, 1H), 3.54 (dd, J=11.2, 2.5 Hz, 1H), 3.44 (d, J=8.9 Hz, 1H), 2.88 (ddd, J=8.8, 7.2, 3.5 Hz, 1H), 2.61 (dtd, J=20.7, 8.6, 6.1 Hz, 1H), 2.08 (dddd, J=15.6, 9.6, 6.6, 3.4 Hz, 1H), 1.76-1.58 (m, 2H), 1.57-1.41 (m, 12H); MS (DCI) m/z 331 [M+H]$^+$.

Example 2G (3aS,6aS)-1-[(1S)-1-phenylethyl]hexahydropyrrolo[3,4-b]pyrrol-6(1H)-one To a solution of the product of Example 2F (9.69 g, 29.3 mmol) in CH$_2$Cl$_2$ (200 mL) at 0° C. was added 2,2,2-trifluoroacetic acid (40.7 mL, 528 mmol) dropwise over 30 minutes. After the addition as complete, the ice-bath was removed and the mixture was allowed to stir at ambient temperature for 2 hours. The mixture was concentrated under reduced pressure and dissolved in CH$_2$Cl$_2$ (200 mL). Saturated, aqueous NaHCO$_3$ (50 mL) was added dropwise via addition funnel and then the layers were separated. The aqueous layer was extracted with CH$_2$Cl$_2$ (3×100 mL), and the combined organic fractions were dried over anhydrous Na$_2$SO$_4$, filtered and concentrated under reduced pressure to give the titled compound (6.71 g, 29.1 mmol, 99% yield) which was used without further purification. $^1$H NMR (500 MHz, DMSO-d$_6$) δ ppm 7.48 (s, 1H), 7.37-7.13 (m, 5H), 4.03 (q, J=6.8 Hz, 1H), 3.31 (dd, J=9.8, 7.7 Hz, 1H), 3.17 (d, J=9.0 Hz, 1H), 2.92 (ddd, J=9.8, 2.1, 1.0 Hz, 1H), 2.80-2.59 (m, 2H), 2.37 (td, J=9.0, 6.2 Hz, 1H), 1.94 (dddd, J=12.1, 9.2, 6.2, 3.3 Hz, 1H), 1.47 (ddt, J=12.1, 8.8, 7.2 Hz, 1H), 1.37 (d, J=6.8 Hz, 3H); MS (DCI) m/z 231 [M+H]$^+$.

Example 2H (3aS,6aS)-5-[1-(2-fluorophenyl)-1H-indazol-4-yl]-1-[(1S)-1-phenylethyl]hexahydropyrrolo[3,4-b]pyrrol-6(1H)-one To a 200 mL flask was added the product of Example 9C (9.58 g, 32.9 mmol), the product from Example 2G (6.89 g, 29.9 mmol), copper(I) iodide (0.285 g, 1.496 mmol) and potassium phosphate tribasic (13.34 g, 62.8 mmol). The contents were purged with nitrogen for 5 minutes and then trans-N,N'-dimethylcyclohexane-1,2-diamine (0.944 mL, 5.98 mmol) and dioxane (80 mL) were added. Nitrogen was blown through the system for 5 minutes. The mixture was warmed to 100° C. and allowed to stir for 90 minutes. The material was allowed to cool to ambient temperature then was filtered through diatomaceous earth with ethyl acetate (500 mL). The filtrate was concentrated under reduced pressure, and the residue was purified by column chromatograph (SiO$_2$, eluting with 5% ethyl acetate/hexanes to 65% ethyl acetate/hexanes) to give the titled compound (10.20 g, 23.2 mmol, 77% yield). $^1$H NMR (500 MHz, CDCl$_3$) δ ppm 8.29 (d, J=1.0 Hz, 1H), 7.70-6.98 (m, 12H), 4.40 (q, J=6.8 Hz, 1H), 4.14 (dd, J=9.6, 7.3 Hz, 1H), 3.76-3.61 (m, 2H), 3.03-2.86 (m, 2H), 2.80 (dt, J=9.2, 7.2 Hz, 1H), 2.24 (dddd, J=11.8, 9.0, 6.9, 4.7 Hz, 1H), 1.91-1.75 (m, 1H), 1.55 (d, J=6.8 Hz, 3H); MS (DCI) m/z 441 [M+H]$^+$.

Example 2I (3aS,6aS)-5-[1-(2-fluorophenyl)-1H-indazol-4-yl]hexahydropyrrolo[3,4-b]pyrrol-6(1H)-one To a 500 mL stainless steel pressure vessel was added the product from Example 2H (23.78 g, 54 mmol), trifluoroethanol (170 mL) and 20% Pd(OH)$_2$ on carbon, wet (3.3 g, 37 mmol), and the mixture was shaken at ambient temperature under 30 psi of hydrogen gas for 30 minutes. The mixture was filtered and washed with trifluoroethanol (20 mL) and the filtrate was concentrated in vacuo to give the titled compound (19.06 g, 56.7 mmol, >100% yield) which was used without purification. $^1$H NMR (400 MHz, CDCl$_3$) δ ppm 8.23 (d, J=1.0 Hz, 1H), 7.64-7.04 (m, 8H), 4.33 (dd, J=10.0, 7.5 Hz, 1H), 4.17 (d, J=8.1 Hz, 1H), 3.91 (q, J=8.8 Hz, 1H), 3.78-3.69 (m, 1H), 3.26-2.93 (m, 2H), 2.28 (dtd, J=12.9, 9.0, 7.4 Hz, 1H), 1.83 (ddt, J=13.1, 7.1, 4.0 Hz, 1H); MS (DCI) m/z 337 [M+H]$^+$.

Example 2J (3aS,6aS)-5-[1-(2-fluorophenyl)-1H-indazol-4-yl]-1-(3-hydroxy-3-methylbutanoyl)hexahydropyrrolo[3,4-b]pyrrol-6(1H)-one To a 1 L round bottom flask with the product of Example 2I (21.0 g, 62.6 mmol) in N,N-dimethylformamide (100 mL), 3-hydroxy-3-methylbutanoic acid (9.46 mL, 75 mmol) and triethylamine (9.60 mL, 68.9 mmol) was added a N,N-dimethylformamide (25 mL) solution of (dimethylamino)-N,N-dimethyl(3-oxido-1H-[1,2,3]triazolo[4,5-b]pyridin-1-yl)methaniminium hexafluorophosphate (HATU, 26.2 g, 68.9 mmol). The reaction mixture was allowed to stir for 30 minutes and then was poured into ethyl acetate (500 mL) and transferred to a separatory funnel. The material was washed with water (100 mL) and brine (100 mL) and the organic layer was dried over anhydrous Na$_2$SO$_4$, filtered and concentrated under reduced pressure. The residue was purified by column chromatography (SiO$_2$, eluted with heptane/ethyl acetate 0-100% over 30 minutes with 60 minute hold) to provide a 98:2 mixture of enantiomers as assessed by chiral supercritical fluid chromatography analysis using a Chiralcel® OD-H column eluting with 5-50% methanol/CO$_2$ at 3 mL/minute at 50 bar over 10 minutes. The material was further purified on a preparative Chiralcel® OD-H column eluting with 30% methanol/CO$_2$ at 80 mL/minute to give the titled compound (17.01 g, 39 mmol, 62% yield). $[α]_D^{20}$ -119.20° (c 0.25, methanol); $^1$H NMR (500 MHz, DMSO-d$_6$) δ ppm 8.35 (d, J=1.0 Hz, 1H), 7.69 (td, J=7.9, 1.8 Hz, 1H), 7.65-7.41 (m, 4H), 7.37-7.22 (m, 2H), 5.12 (d, J=8.0 Hz, 1H), 4.96 (s, 1H), 4.30 (ddd, J=9.9, 6.4, 3.6 Hz, 1H), 3.78-3.45 (m, 3H), 3.27-3.14 (m, 1H), 2.82 (d, J=15.1 Hz, 1H), 2.72 (d, J=15.0 Hz, 1H), 2.40-2.19 (m, 1H), 1.87 (dq, J=13.0, 9.0 Hz, 1H), 1.22 (d, J=11.8 Hz, 6H); MS (DCI) m/z 437 [M+H]$^+$.

Example 3

(3aR*,6aR*)-5-[1-(2-fluorophenyl)-1H-indazol-4-yl]-1-[(3R)-tetrahydrofuran-3-ylcarbonyl]hexahydropyrrolo[3,4-b]pyrrol-6(1H)-one (Dimethylamino)-N,N-dimethyl(3-oxido-1H-[1,2,3]triazolo[4,5-b]pyridin-1-yl)methaniminium hexafluorophosphate (HATU, 119 mg, 0.31 mmol) was added to a mixture of the product of Example 1G (100 mg, 0.30 mmol), (R)-tetrahydrofuran-3-carboxylic acid (36 mg, 0.31 mmol) and triethylamine (0.124 mL, 0.89 mmol) in N,N-dimethylformamide (2.0 mL). The reaction mixture was stirred at ambient temperature for 60 minutes. The mixture was filtered through a glass microfiber frit and directly purified by preparative HPLC [Waters XBridge™ C18 5 μm OBD™ column, 50×100 mm, flow rate 90 mL/minute, 5-95% gradient of acetonitrile in buffer (0.1 M aqueous ammonium bicarbonate, adjusted to pH 10 with ammonium hydroxide)] to give the titled compound (95 mg, 0.22 mmol, 74% yield). $^1$H NMR (400 MHz, DMSO-$d_6$, 90° C.) δ ppm 8.30 (s, 1H), 7.64 (td, J=7.8, 1.5 Hz, 1H), 7.53-7.61 (m, 1H), 7.39-7.52 (m, 3H), 7.29 (d, J=7.6 Hz, 1H), 7.25 (dd, J=8.3, 2.3 Hz, 1H), 4.94-5.13 (m, 1H), 4.28 (ddd, J=9.8, 6.8, 2.9 Hz, 1H), 3.92-4.07 (m, 1H), 3.67-3.86 (m, 5H), 3.45-3.67 (m, 2H), 3.16-3.35 (m, 1H), 2.21-2.36 (m, 1H), 1.83-2.21 (m, 3H); MS (ESI$^+$) m/z 435 [M+H]$^+$.

Example 4 rel-(3aR,6aR)-5-[1-(2-fluorophenyl)-1H-indazol-4-yl]-1-(2-hydroxy-2-methylpropanoyl)hexahydropyrrolo[3,4-b]pyrrol-6(1H)-one (Dimethylamino)-N,N-dimethyl(3-oxido-1H-[1,2,3]triazolo[4,5-b]pyridin-1-yl)methaniminium hexafluorophosphate (HATU, 119 mg, 0.31 mmol) was added to a mixture of the product of Example 1G (100 mg, 0.30 mmol), 2-hydroxyisobutyric acid (33 mg, 0.31 mmol) and triethylamine (0.124 mL, 0.89 mmol) in N,N-dimethylformamide (2.0 mL). The reaction mixture was stirred at 40° C. for 60 minutes. The mixture was filtered through a glass microfiber frit and directly purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (48 mg, 0.11 mmol, 38% yield). $^1$H NMR (400 MHz, DMSO-$d_6$) δ ppm 8.32 (s, 1H), 7.69 (td, J=7.8, 1.5 Hz, 1H), 7.55-7.64 (m, 2H), 7.43-7.54 (m, 2H), 7.23-7.37 (m, 2H), 5.48-5.59 and 5.85-5.91 (two m, 1H, amide rotamers), 5.21-5.37 (m, 1H), 4.15-4.40 (m, 1H), 3.59-3.78 (m, 2H), 2.96-3.25 (m, 1H), 2.15-2.34 (m, 1H), 2.17-2.29 (m, 1H), 1.72-1.97 (m, 1H), 1.27-1.54 (m, 6H); MS (ESI$^-$) m/z 421 [M−H]$^-$.

Example 5 rel-(3aR,6aR)-5-[1-(2-fluorophenyl)-1H-indazol-4-yl]-1-[(1-hydroxycyclopropyl)carbonyl]hexahydropyrrolo[3,4-b]pyrrol-6(1H)-one (Dimethylamino)-N,N-dimethyl(3-oxido-1H-[1,2,3]triazolo[4,5-b]pyridin-1-yl)methaniminium hexafluorophosphate (HATU, 119 mg, 0.31 mmol) was added to a mixture of the product of Example 1G (100 mg, 0.30 mmol), 1-hydroxy-1-cyclopropanecarboxylic acid (32 mg, 0.31 mmol) and triethylamine (0.124 mL, 0.89 mmol) in N,N-dimethylformamide (2.0 mL). The reaction mixture was stirred at 40° C. for 60 minutes. The mixture was filtered through a glass microfiber frit and directly purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (58 mg, 0.14 mmol, 46% yield). $^1$H NMR (400 MHz, DMSO-$d_6$, 90° C.) δ ppm 8.29 (d, J=0.9 Hz, 1H), 7.65 (td, J=7.8, 1.5 Hz, 1H), 7.53-7.61 (m, 1H), 7.45-7.52 (m, 2H), 7.42 (td, J=7.6, 1.5 Hz, 1H), 7.29 (d, J=7.0 Hz, 1H), 7.26 (dd, J=8.5, 2.8 Hz, 1H), 6.07 (s, 1H), 5.53 (d, J=7.6 Hz, 1H), 4.33 (dd, J=9.9, 6.9 Hz, 1H), 3.78-3.88 (m, 1H), 3.76 (dd, J=9.8, 1.8 Hz, 1H), 3.64 (t, J=12.7 Hz, 1H), 3.22 (ddd, J=14.9, 7.3, 7.0 Hz, 1H), 2.19-2.31 (m, 1H), 1.84-1.95 (m, 1H), 1.18 (dd, J=10.4, 3.7 Hz, 1H), 1.01-1.12 (m, 1H), 0.80-0.89 (m, 2H); MS (ESI−) m/z 419 [M−H]$^-$.

Example 6 rel-(3aR,6aR)-1-acetyl-5-[1-(2-fluorophenyl)-1H-indazol-4-yl]hexahydropyrrolo[3,4-b]pyrrol-6(1H)-one The product of Example 1G (100 mg, 0.30 mmol) was dissolved in acetic anhydride (2.0 mL). The reaction mixture was stirred at ambient temperature for 2 hours. The mixture was concentrated in vacuo, and the resulting residue was purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (33 mg, 0.09 mmol, 29% yield). $^1$H NMR (400 MHz, DMSO-$d_6$, 90° C.) δ ppm 8.29 (d, J=0.6 Hz, 1H), 7.64 (td, J=7.8, 1.8 Hz, 1H), 7.53-7.60 (m, 1H), 7.39-7.52 (m, 3H), 7.28 (d, J=7.3 Hz, 1H), 7.24 (dd, J=8.4, 2.6 Hz, 1H), 4.89 (br s, 1H), 4.22-4.33 (m, 1H), 3.44-3.77 (m, 4H), 3.23 (br s, 1H), 2.15-2.32 (m, 3H), 1.82-1.99 (m, 1H); MS (ESI$^+$) m/z 379 [M+H]$^+$.

Example 7

(3aR*,6aR*)-5-[1-(2-fluorophenyl)-1H-indazol-4-yl]-1-[(3R)-3-hydroxybutanoyl]hexahydropyrrolo[3,4-b]pyrrol-6(1H)-one (Dimethylamino)-N,N-dimethyl(3-oxido-1H-[1,2,3]triazolo[4,5-b]pyridin-1-yl)methaniminium hexafluorophosphate (HATU, 119 mg, 0.31 mmol) was added to a mixture of the product of Example 1G (100 mg, 0.30 mmol), (R)-3-hydroxybutanoic acid (33 mg, 0.31 mmol) and triethylamine (0.124 mL, 0.89 mmol) in N,N-dimethylformamide (2.0 mL). The reaction mixture was stirred at 40° C. for 60 minutes. The mixture was filtered through a glass microfiber frit and directly purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (81 mg, 0.19 mmol, 65% yield). $^1$H NMR (400 MHz, DMSO-$d_6$, 90° C.) δ ppm 8.29 (s, 1H), 7.65 (td, J=7.7, 1.7 Hz, 1H), 7.54-7.61 (m, 1H), 7.39-7.53 (m, 3H), 7.28 (d, J=7.6 Hz, 1H), 7.25 (dd, J=8.5, 2.4 Hz, 1H), 5.02 (br s, 1H), 4.32-4.36 (m, 1H), 4.29 (dd, J=9.9, 6.6 Hz, 1H), 4.04-4.15 (m, 1H), 3.73 (d, J=9.8 Hz, 1H), 3.50-3.67 (m, 2H), 3.13-3.32 (m, 1H), 2.59-2.89 (m, 2H), 2.19-2.36 (m, 1H), 1.82-1.95 (m, 1H), 1.15 (d, J=6.1 Hz, 3H); MS (ESI$^+$) m/z 423 [M+H]$^+$.

Example 8 rel-(3aR,6aR)-2-[1-(2-fluorophenyl)-1H-indazol-4-yl]-5-(3-methylbutanoyl)hexahydropyrrolo[3,4-c]pyrrol-1(2H)-one The product of Example 10A (0.16 g, 0.47 mmol), N-ethyl-N-isopropylpropan-2-amine (0.30 mL, 1.72 mmol), isovaleric acid (0.06 mL, 0.55 mmol) and (dimethylamino)-N,N-dimethyl(3-oxido-1H-[1,2,3]triazolo[4,5-b]pyridin-1-yl)methaniminium hexafluorophosphate (HATU, 0.21 g, 0.54 mmol) in tetrahydrofuran (3 mL) were processed as described in Example 10B to give the titled compound (0.071 g, 0.17 mmol, 36% yield). $^1$H NMR (300 MHz, DMSO-$d_6$) δ ppm 8.25 (dd, J=3.6, 0.8 Hz, 1H), 7.72-7.65 (m, 1H), 7.65-7.54 (m, 2H), 7.53-7.41 (m, 2H), 7.32-7.22 (m, 2H), 4.38-4.28 (m, 1H), 4.01 (d, J=0.6 Hz, 1H), 3.98-3.84 (m, 2H), 3.84-3.69 (m, 2H), 3.59-3.34 (m, 2H), 2.24-2.10 (m, 2H), 2.10-1.96 (m, 1H), 0.97-0.86 (m, 6H); MS (ESI$^+$) m/z 421 [M+H]$^+$.

Example 9 rel-(3aR,6aR)-5-benzyl-2-[1-(2-fluorophenyl)-1H-indazol-4-yl]hexahydropyrrolo[3,4-c]pyrrol-1(2H)-one Example 9A rel-tert-butyl(3aS,6aR)-5-benzyl-1-oxohexahydropyrrolo[3,4-c]pyrrole-2(1H)-carboxylate A solution of tert-butyl 2-oxo-2,5-dihydro-1H-pyrrole-1-carboxylate (Chem-Impex) (7.39 g, 40.3 mmol) in $CH_2Cl_2$ (100 mL) was cooled to 0° C. 2,2,2-Trifluoroacetic acid (0.60 mL, 7.79 mmol) was added followed by the slow addition of N-(methoxymethyl)-N-(trimethylsilylmethyl)benzylamine (12.5 mL, 48.9 mmol) in $CH_2Cl_2$ (20.0 mL) via an addition funnel over 2 hours. The reaction mixture was allowed to warm to ambient temperature and was stirred for 20 h.

The reaction mixture was partitioned between $CH_2Cl_2$ (50 mL) and saturated, aqueous $NaHCO_3$ (50 mL). The layers were separated, and the organic layer was washed with saturated, aqueous $NaHCO_3$ (1×15 mL) and brine (1×10 mL). The organic layer was then dried over anhydrous $Na_2SO_4$, filtered and concentrated under reduced pressure. The crude material was purified via column chromatography ($SiO_2$, 10% ethyl acetate/heptanes to 100% ethyl acetate) to give the titled compound (12.8 g, 11.8 mmol, 92% yield); MS (ESI$^+$) m/z 317 [M+H]$^+$.

Example 9B rel-(3aR,6aR)-5-benzylhexahydropyrrolo[3,4-c]pyrrol-1(2H)-one

To the product of Example 9A (2.02 g, 6.38 mmol) in $CH_2Cl_2$ (20 mL) was added 2,2,2-trifluoroacetic acid (4.0 mL, 51.9 mmol). The reaction mixture was stirred at ambient temperature for 2 h. The mixture was concentrated under reduced pressure, and the residue was dissolved in methanol. The mixture was concentrated under reduced pressure and again the residue was dissolved in methanol and again was concentrated under reduced pressure. The residue was dissolved in $CH_2Cl_2$ (20 mL), and the resultant solution was washed with 1 M NaOH (2×10 mL) and brine (1×10 mL). The organic layer was dried over anhydrous $MgSO_4$, filtered and concentrated under reduced pressure to give the titled compound (1.2 g, 5.6 mmol, 88% yield); MS (ESI$^+$) m/z 217 [M+H]$^+$.

Example 9C 4-bromo-1-(2-fluorophenyl)-1H-indazole

To a solution of 2-bromo-6-fluorobenzaldehyde (Combi-Blocks, 10 g, 49.3 mmol) and (2-fluorophenyl)hydrazine hydrochloride (8.01 g, 49.3 mmol) in N-methyl-2-pyrrolidinone (100 mL) at ambient temperature was added cesium carbonate (33.7 g, 103 mmol). The mixture was heated to 140° C. and was stirred for 1 h. After 1 h, the reaction mixture was allowed to cool to ambient temperature, and water was added (300 mL). The mixture was stirred for 1 h, and then the solids were isolated via filtration, washed with water and dried in a vacuum oven at 50° C. to give the titled compound (13.0 g, 44.7 mmol, 91% yield). $^1$H NMR (400 MHz, DMSO-$d_6$) δ ppm 8.41 (d, J=0.5 Hz, 1H), 7.72 (td, J=7.8, 1.6 Hz, 1H), 7.66-7.38 (m, 8H); MS (DCI) m/z 291, 293 [M+H]$^+$.

Example 9D rel-(3aR,6aR)-5-benzyl-2-[1-(2-fluorophenyl)-1H-indazol-4-yl]hexahydropyrrolo[3,4-c]pyrrol-1(2H)-one The product of Example 9C (1.39 g, 4.76 mmol), the product of Example 9B (1.2139 g, 5.61 mmol), CuI (Strem, 0.053 g, 0.28 mmol) and potassium phosphate tribasic (Strem, 2.13 g, 10.2 mmol) were combined in 1,4-dioxane (20 mL). $N_2$ was vigorously bubbled through the mixture for 20 minutes. Trans-N,N'-dimethylcyclohexane-1,2-diamine (0.15 mL, 0.951 mmol) was added, and the reaction mixture was heated to 105° C. and was stirred for 48 hours. The mixture was cooled to ambient temperature and was filtered through a plug of diatomaceous earth with ethyl acetate. The filtrate was concentrated under reduced pressure, and the residue was purified by column chromatography ($SiO_2$, 50% ethyl acetate/heptanes to 100% ethyl acetate) to give the titled compound (1.69 g, 3.97 mmol, 83% yield). $^1$H NMR (400 MHz, DMSO-$d_6$) δ ppm 8.23 (d, J=0.8 Hz, 1H), 7.70 (td, J=7.8, 1.6 Hz, 1H), 7.65-7.53 (m, 2H), 7.52-7.42 (m, 2H), 7.36-7.29 (m, 4H), 7.29-7.21 (m, 3H), 4.29 (t, J=9.2 Hz, 1H), 3.70 (dd, J=9.7, 2.9 Hz, 1H), 3.64 (dd, J=30.4, 13.1 Hz, 2H), 3.26-3.18 (m, 1H), 3.10 (d, J=9.0 Hz, 1H), 3.07-2.98 (m, 1H), 2.88 (dd, J=9.4, 1.7 Hz, 1H), 2.54 (dd, J=9.3, 7.4 Hz, 1H), 2.45 (dd, J=8.9, 7.6 Hz, 1H); MS (ESI$^+$) m/z 427 [M+H]$^+$.

Example 10 rel-(3aR,6aR)-2-[1-(2-fluorophenyl)-1H-indazol-4-yl]-5-(tetrahydrofuran-2-ylacetyl)hexahydropyrrolo[3,4-c]pyrrol-1(2H)-one Example 10A 2-(1-(2-fluorophenyl)-1H-indazol-4-yl)hexahydropyrrolo[3,4-c]pyrrol-1(2H)-one To the product of Example 9D (1.64 g, 3.84 mmol) in tetrahydrofuran (40 mL) was added to 20% Pd(OH)$_2$/C, wet (0.34 g, 0.25 mmol) in a 50 mL pressure bottle, and the mixture was stirred for 16 h at 50 psi $H_2$ and 50° C. The mixture was cooled to ambient temperature and was filtered through a nylon membrane. The filtrate was concentrated under reduced pressure, diluted with diethyl ether (20 mL) and concentrated again under reduced pressure to give the titled compound as a white solid (1.25 g, 3.73 mmol, 97% yield). MS (ESI$^+$) m/z 337 [M+H]$^+$.

Example 10B rel-(3aR,6aR)-2-[1-(2-fluorophenyl)-1H-indazol-4-yl]-5-(tetrahydrofuran-2-ylacetyl)hexahydropyrrolo[3,4-c]pyrrol-1(2H)-one N-Ethyl-N-isopropylpropan-2-amine (0.20 mL, 1.15 mmol) was added to a mixture of the product of Example 10A (0.10 g, 0.30 mmol), 2-(tetrahydrofuran-2-yl)acetic acid (Princeton, 0.058 g, 0.44 mmol) and (dimethylamino)-N,N-dimethyl(3-oxido-1H-[1,2,3]triazolo[4,5-b]pyridin-1-yl)methaniminium hexafluorophosphate (HATU, 0.135 g, 0.354 mmol) in tetrahydrofuran (1.5 mL). The reaction mixture was stirred at ambient temperature for 90 minutes. The mixture was diluted with ethyl acetate (10 mL) and washed with $H_2O$ (3×5 mL) and brine (1×5 mL). The organic layer was concentrated under reduced pressure, and the residue was purified by column chromatography ($SiO_2$, 100% $CH_2Cl_2$ to 5% methanol/$CH_2Cl_2$) to give the titled compound (93 mg, 0.21 mmol, 69% yield). $^1$H NMR (400 MHz, methanol-$d_4$) δ ppm 8.29-8.20 (m, 1H), 7.65-7.60 (m, 1H), 7.60-7.53 (m, 1H), 7.53-7.48 (m, 1H), 7.47-7.38 (m, 2H), 7.32-7.18 (m, 2H), 4.45-4.36 (m, 1H), 4.35-3.33 (m, 11H), 2.80-2.62 (m, 1H), 2.63-2.42 (m, 1H), 2.19-2.05 (m, 1H), 2.01-1.81 (m, 2H), 1.74-1.52 (m, 1H); MS (ESI$^+$) m/z 449 [M+H]$^+$.

Example 11 rel-(3aR,6aR)-2-[1-(2-fluorophenyl)-1H-indazol-4-yl]-5-(3-hydroxybutanoyl)hexahydropyrrolo[3,4-c]pyrrol-1(2H)-one The product of Example 10A (0.10 g, 0.30 mmol), N-ethyl-N-isopropylpropan-2-amine (0.20 mL, 1.1 mmol), 3-hydroxybutyric acid (0.05 mL, 0.54 mmol) and (dimethylamino)-N,N-dimethyl(3-oxido-1H-[1,2,3]triazolo[4,5-b]pyridin-1-yl)methaniminium hexafluorophosphate (HATU, 0.13 g, 0.35 mmol) in tetrahydrofuran (1.5 mL) were processed as described in Example 10B to give the titled compound (0.051 g, 0.12 mmol, 40% yield). $^1$H NMR (500 MHz, methanol-$d_4$) δ ppm 8.27-8.21 (m, 1H), 7.63 (t, J=7.4 Hz, 1H), 7.60-7.53 (m, 1H), 7.53-7.48 (m, 1H), 7.42 (dd, J=15.8, 8.2 Hz, 2H), 7.33-7.27 (m, 1H), 7.27-7.21 (m, 1H), 4.44-4.37 (m, 1H), 4.26-4.19 (m, 1H), 4.19-3.99 (m, 2H), 3.96-3.71 (m, 2H), 3.69-3.35 (m, 3H), 2.66-2.39 (m, 2H), 1.29-1.22 (m, 3H); MS (ESI$^+$) m/z 423 [M+H]$^+$.

Example 12 rel-(3aR,6aR)-2-[1-(2-fluorophenyl)-1H-indazol-4-yl]-5-(1H-imidazol-1-ylcarbonyl)hexahydropyrrolo[3,4-c]pyrrol-1(2H)-one The product of Example 10A (0.40 g, 1.19 mmol) and 1,1'-carbonyldiimidazole (0.22 g, 1.38 mmol) were combined in tetrahydrofuran (10.0 mL). The reaction mixture was heated to 70° C. (reflux) and was allowed to stir for 20 h. The reaction mixture was allowed to cool to ambient temperature and was partitioned between ethyl acetate (10 mL) and brine (5 mL). The organic layer was washed with brine (2×5 mL), dried over anhydrous $MgSO_4$ and concentrated under reduced pressure to give the titled compound (0.47 g, 1.09 mmol, 91% yield). $^1$H NMR (400 MHz, DMSO-$d_6$) δ ppm 8.35 (s, 1H), 8.19 (d, J=0.9 Hz, 1H), 7.69 (td, J=7.9, 1.6 Hz, 1H), 7.63 (t, J=1.4 Hz, 1H), 7.62-7.53 (m, 2H), 7.53-7.42 (m, 2H), 7.31 (d, J=7.4 Hz, 1H), 7.28 (dd, J=8.4, 3.0 Hz, 1H), 7.04 (s, 1H), 4.33 (dd, J=10.0, 6.1 Hz, 1H), 4.09-3.92 (m, 3H), 3.84 (d, J=9.9 Hz, 1H), 3.70 (dd, J=11.7, 7.6 Hz, 1H), 3.53 (td, J=7.8, 2.7 Hz, 1H), 3.31-3.21 (m, 1H); MS (ESI$^+$) m/z 431 [M+H]$^+$.

Example 13 rel-(3aR,6aR)-5-[1-(2-fluorophenyl)-1H-indazol-4-yl]-N-(1,3-oxazol-5-ylmethyl)-4-oxohexahydropyrrolo[3,4-c]pyrrole-2(1H)-carboxamide Iodomethane (2.2 mL, 4.40 mmol) was added to a solution of the product of Example 12 (0.47 g, 1.09 mmol) in acetonitrile (8.0 mL), and the mixture was stirred at ambient temperature for 20 h. The reaction mixture was partitioned between ethyl acetate (10 mL) and water (5 mL). The organic layer was washed with water (2×5 mL) and brine (1×5 mL), dried over anhydrous $MgSO_4$, filtered and concentrated under reduced pressure to give the intermediate 1-({5-[1-(2-fluorophenyl)-1H-indazol-4-yl]-4-oxohexahydropyrrolo[3,4-c]pyrrol-2(1H)-yl}carbonyl)-3-methyl-1H-imidazol-3-ium iodide.

The intermediate 1-({5-[1-(2-fluorophenyl)-1H-indazol-4-yl]-4-oxohexahydropyrrolo[3,4-c]pyrrol-2(1H)-yl}carbonyl)-3-methyl-1H-imidazol-3-ium iodide (0.1037 g, 0.181 mmol), oxazol-5-yl-methylamine hydrochloride (JW Pharmlab, 0.026 g, 0.19 mmol) and triethylamine (0.05 mL, 0.36 mmol) were combine in $CH_2Cl_2$ (1.5 mL). The reaction mixture was stirred at ambient temperature for 1 h. The mixture was diluted with $CH_2Cl_2$ (5 mL), and the resultant mixture was transferred to a separatory funnel. The mixture was washed with water (2×5 mL) and brine (1×5 mL) and concentrated under reduced pressure. The residue was purified by column chromatography ($SiO_2$, 100% $CH_2Cl_2$ to 5% methanol/$CH_2Cl_2$) to give the titled compound (0.016 g, 0.035 mmol, 24% yield). $^1$H NMR (400 MHz, DMSO-$d_6$) δ ppm 8.26 (d, J=0.7 Hz, 1H), 8.23 (s, 1H), 7.69 (td, J=7.9, 1.6 Hz, 1H), 7.64-7.52 (m, 2H), 7.51-7.41 (m, 2H), 7.31-7.23 (m, 2H), 6.95 (s, 1H), 6.90 (t, J=5.7 Hz, 1H), 4.37-4.25 (m, 3H), 3.84-3.72 (m, 3H), 3.51 (dd, J=10.4, 7.8 Hz, 1H), 3.42 (td, J=7.9, 1.3 Hz, 1H), 3.28 (dd, J=11.0, 6.7 Hz, 1H), 3.23-3.12 (m, 1H); MS (ESI$^+$) m/z 461 [M+H]$^+$.

Example 14 rel-(3aR,6aR)-2-[1-(2-fluorophenyl)-1H-indazol-4-yl]-5-[(5-methyl-1,2-oxazol-3-yl)carbonyl]hexahydropyrrolo[3,4-c]pyrrol-1(2H)-one N-Ethyl-N-isopropylpropan-2-amine (0.1 mL, 0.573 mmol) was added to a solution of the product of Example 10A (0.071 g, 0.21 mmol) and 5-methylisoxazole-3-carbonyl chloride (Maybridge, Int., 0.044 g, 0.30 mmol) in $CH_2Cl_2$ (1.0 mL). The reaction mixture was stirred at ambient temperature for 20 h and then was diluted with $CH_2Cl_2$ (5.0 mL). The mixture was transferred to an addition funnel and was washed with water (2×5 mL) and brine (1×5 mL). The organic phase was concentrated under reduced pressure, and the residue was purified by column chromatography ($SiO_2$, 50% heptanes/ethyl acetate to 100% ethyl acetate) to give the titled compound (0.066 g, 0.15 mmol, 70% yield). $^1$H NMR (500 MHz, DMSO-$d_6$) δ ppm 8.28 (dd, J=13.9, 0.8 Hz, 1H), 7.69 (td, J=7.9, 1.5 Hz, 1H), 7.64-7.53 (m, 2H), 7.52-7.41 (m, 2H), 7.30 (d, J=7.4 Hz, 1H), 7.27 (dd, J=8.3, 2.2 Hz, 1H), 6.53 (d, J=0.8 Hz, 1H), 4.41-4.29 (m, 1H), 4.28-4.19 (m, 1H), 4.10-3.80 (m, 3H), 3.70-3.55 (m, 1H), 3.55-3.47 (m, 1H), 3.30-3.19 (m, 1H), 2.47 (dd, J=14.8, 0.5 Hz, 3H); MS (ESI+) m/z 446 [M+H]+.

Example 15 rel-(3aR,6aR)-5-[1-(2-fluorophenyl)-1H-indazol-4-yl]-N,N-dimethyl-4-oxohexahydropyrrolo[3,4-c]pyrrole-2(1H)-carboxamide Triethylamine (0.10 mL, 0.72 mmol) was added to a mixture of the intermediate from Example 13, 1-({5-[1-(2-fluorophenyl)-1H-indazol-4-yl]-4-oxohexahydropyrrolo[3,4-c]pyrrol-2(1H)-yl}carbonyl)-3-methyl-1H-imidazol-3-ium iodide (0.154 g, 0.27 mmol) and dimethylamine (0.50 mL, 1.00 mmol) in tetrahydrofuran (1.0 mL). The reaction mixture was stirred at ambient temperature for 30 minutes. The mixture was diluted with ethyl acetate (5 mL), and the material was transferred to a separatory funnel. The material was washed with water (2×5 mL) and brine (1×5 mL) and concentrated under reduced pressure. The residue was purified by column chromatography (SiO$_2$, 5% ethanol/ethyl acetate to 10% ethanol/ethyl acetate) to give the titled compound (0.051 g, 0.13 mmol, 47% yield). $^1$H NMR (400 MHz, DMSO-d$_6$) δ ppm 8.24 (d, J=0.8 Hz, 1H), 7.68 (td, J=7.9, 1.6 Hz, 1H), 7.64-7.52 (m, 2H), 7.52-7.42 (m, 2H), 7.29-7.21 (m, 2H), 4.33 (dd, J=9.9, 6.8 Hz, 1H), 3.81-3.71 (m, 2H), 3.65-3.41 (m, 3H), 3.37-3.32 (m, 1H), 3.14-3.04 (m, 1H), 2.78 (s, 6H); MS (ESI+) m/z 408 [M+H]+.

Example 16 rel-(3aR,6aR)-2-[1-(2-fluorophenyl)-1H-indazol-4-yl]-5-(1,3-oxazol-4-ylcarbonyl)hexahydropyrrolo[3,4-c]pyrrol-1(2H)-one N-Ethyl-N-isopropylpropan-2-amine (0.10 mL, 0.573 mmol) was added to a mixture of the product of Example 10A (0.070 g, 0.21 mmol), oxazole-4-carboxylic acid (Ark-Pharm, Inc., 0.029 g, 0.26 mmol) and (dimethylamino)-N,N-dimethyl(3-oxido-1H-[1,2,3]triazolo[4,5-b]pyridin-1-yl)methaniminium hexafluorophosphate (HATU, 0.098 g, 0.26 mmol) in tetrahydrofuran (1.0 mL). The reaction mixture was stirred at ambient temperature for 4 h and was then diluted with ethyl acetate (5.0 mL). The mixture was transferred to an addition funnel and was washed with water (1×5 mL), 1 N HCl (1×5 mL), saturated, aqueous NaHCO$_3$ (1×5 mL) and brine (1×5 mL). The organic layer was concentrated under reduced pressure, and the residue was purified by column chromatography (SiO$_2$, 100% CH$_2$Cl$_2$ to 5% methanol in CH$_2$Cl$_2$) to give the titled compound (0.068 g, 0.16 mmol, 76% yield). $^1$H NMR (400 MHz, DMSO-d$_6$) δ ppm 8.67 (d, J=7.2 Hz, 1H), 8.52 (d, J=16.4 Hz, 1H), 8.27 (d, J=14.0 Hz, 1H), 7.68 (td, J=7.8, 1.5 Hz, 1H), 7.64-7.52 (m, 2H), 7.51-7.40 (m, 2H), 7.30 (d, J=7.5 Hz, 1H), 7.26 (dd, J=8.4, 2.9 Hz, 1H), 4.53-4.31 (m, 2H), 4.11-3.98 (m, 1H), 3.92-3.75 (m, 2H), 3.62-3.40 (m, 2H), 3.29-3.14 (m, 1H); MS (ESI+) m/z 432 [M+H]+.

Example 17 rel-(3aR,6aR)-5-acetyl-2-[1-(2-fluorophenyl)-1H-indazol-4-yl]hexahydropyrrolo[3,4-c]pyrrol-1(2H)-one A mixture of N-ethyl-N-isopropylpropan-2-amine (0.06 mL, 0.34 mmol), the product of Example 10A (0.059 g, 0.174 mmol) and acetyl chloride (0.02 mL, 0.28 mmol) in CH$_2$Cl$_2$ (1.0 mL) were processed as described in Example 14 to give the titled compound (0.51 g, 0.136 mmol, 78% yield). $^1$H NMR (400 MHz, DMSO-d$_6$) δ ppm 8.29 (dd, J=3.0, 0.9 Hz, 1H), 7.69 (td, J=7.9, 1.6 Hz, 1H), 7.64-7.52 (m, 2H), 7.52-7.42 (m, 2H), 7.34-7.23 (m, 2H), 4.36-4.29 (m, 1H), 3.96-3.73 (m, 3H), 3.57-3.36 (m, 2H), 3.26 (dd, J=12.0, 7.4 Hz, 1H), 3.20-3.10 (m, 1H), 2.00 (d, J=8.8 Hz, 3H); MS (ESI+) m/z 379 [M+H]+.

Example 18 rel-(3aR,6aR)-2-[1-(2-fluorophenyl)-1H-indazol-4-yl]-5-(1,3-oxazol-2-ylmethyl)hexahydropyrrolo[3,4-c]pyrrol-1(2H)-one The product of Example 10A (0.12 g, 0.36 mmol) was added to a 0° C. suspension of sodium hydride (60% dispersion in mineral oil, 0.061 g, 1.53 mmol) in tetrahydrofuran (2.0 mL). After 20 minutes, the ice bath was removed, and 2-chloromethyl oxazole (Astatech, 0.078 g, 0.66 mmol) was added. The reaction mixture was stirred at ambient temperature for 20 h and then was quenched with water (5 mL) and diluted with ethyl acetate (5 mL). The layers were separated, and the aqueous layer was extracted with ethyl acetate (2×5 mL). The combined organic fractions were washed with brine (1×5 mL) and concentrated under reduced pressure. The residue was purified via column chromatography (SiO$_2$, 100% CH$_2$Cl$_2$ to 5% methanol in CH$_2$Cl$_2$) to give the titled compound (0.073 g, 0.18 mmol, 49% yield). $^1$H NMR (500 MHz, DMSO-d$_6$) δ ppm 8.23 (d, J=0.7 Hz, 1H), 8.08 (d, J=0.5 Hz, 1H), 7.69 (td, J=7.8, 1.4 Hz, 1H), 7.63-7.53 (m, 2H), 7.51-7.41 (m, 2H), 7.27-7.17 (m, 3H), 4.26 (t, J=9.2 Hz, 1H), 3.83 (q, J=14.3 Hz, 2H), 3.70 (dd, J=9.8, 2.9 Hz, 1H), 3.24 (dd, J=12.3, 4.6 Hz, 1H), 3.16 (d, J=9.1 Hz, 1H), 3.09-2.96 (m, 1H), 2.93 (dd, J=9.3, 1.9 Hz, 1H), 2.70-2.57 (m, 2H); MS (ESI+) m/z 418 [M+H]+.

Example 19 rel-(3aR,6aR)-2-[1-(2-fluorophenyl)-1H-indazol-4-yl]-5-isobutyrylhexahydropyrrolo[3,4-c]pyrrol-1(2H)-one A mixture of N-ethyl-N-isopropylpropan-2-amine (0.08 mL, 0.46 mmol), the product of Example 10A (0.065 g, 0.19 mmol) and isobutyryl chloride (0.04 mL, 0.38 mmol) in CH$_2$Cl$_2$ (1.0 mL) was processed as described in Example 14 to give the titled compound (0.071 g, 0.17 mmol, 89% yield). $^1$H NMR (500 MHz, DMSO-d$_6$) δ ppm 8.23 (d, J=9.5 Hz, 1H), 7.68 (td, J=7.8, 1.4 Hz, 1H), 7.63-7.53 (m, 2H), 7.52-7.41 (m, 2H), 7.32-7.24 (m, 2H), 4.34 (dd, J=9.9, 6.1 Hz, 1H), 3.98 (t, J=8.9 Hz, 1H), 3.91-3.74 (m, 2H), 3.59-3.45 (m, 1H), 3.42-3.33 (m, 1H), 3.30-3.23 (m, 1H), 3.20-3.10 (m, 1H), 2.79-2.65 (m, 1H), 1.07-0.97 (m, 6H); MS (ESI+) m/z 407 [M+H]+.

Example 20

(3aR,6aS)-2-[1-(2-fluorophenyl)-1H-indazol-4-yl]-5-isobutyrylhexahydropyrrolo[3,4-c]pyrrol-1(2H)-one

Example 20A (3aS,6aR)-tert-butyl 1-oxo-5-((R)-1-phenylethyl)hexahydropyrrolo[3,4-c]pyrrole-2(1H)-carboxylate To a solution of 2-oxo-2,4-dihydro-pyrrole-1-carboxylic acid tert-butyl ester (Chem-Impex, 17 g, 90.5 mmol) in CH$_2$Cl$_2$ (200 mL) at 0° C. was added trifluoroacetic acid (TFA, 2.53 mL, 32.8 mmol) followed by the (R)-(+)-N-methoxymethyl-N-(trimethylsilyl)methyl-1-phenylethylamine (Small Molecules, 21.5 g, 82 mmol) in CH$_2$Cl$_2$ (15 mL) dropwise via syringe pump over 2 h. The mixture was allowed to warm slowly to ambient temperature and was stirred for 16 h. The mixture was quenched with saturated, aqueous NaHCO$_3$ (30 mL), and the layers were separated. The aqueous layer was extracted with CH$_2$Cl$_2$ (3×25 mL), and the combined organic fractions were dried over anhydrous Na$_2$SO$_4$, filtered, and concentrated under reduced pressure. The residue was purified via column chromatography (SiO$_2$, 100% CH$_2$Cl$_2$ to 20% ethyl acetate/CH$_2$Cl$_2$ to 40% ethyl acetate/CH$_2$Cl$_2$) to give the first eluting isomer, the product of Example 20B (11.8 g, 26.7 mmol, 33% yield), and the second eluting isomer, the titled compound (10.8 g, 32.6 mmol, 40% yield) (stereochemistry of second eluting isomer confirmed by X-ray crystal structure). $^1$H NMR (400 MHz, chloroform-d) δ ppm 7.34-7.17 (m, 5H), 3.90 (dt, J=19.1, 9.6 Hz, 1H), 3.54 (dd, J=11.1, 3.1 Hz, 1H), 3.31-3.16 (m, 1H), 3.10-2.98 (m, 1H), 2.93 (d, J=9.3 Hz, 1H), 2.84-2.65 (m, 2H), 2.59-2.44 (m, 2H), 1.54 (s, 9H), 1.36 (d, J=6.2 Hz, 3H); MS (ESI$^+$) m/z 331 [M+H]$^+$.

Example 20B (3aR,6aS)-tert-butyl 1-oxo-5-((R)-1-phenylethyl)hexahydropyrrolo[3,4-c]pyrrole-2(1H)-carboxylate The first eluting isomer of Example 20A is the titled compound. $^1$H NMR (400 MHz, chloroform-d) δ ppm 7.35-7.21 (m, 5H), 3.88 (dd, J=10.9, 9.5 Hz, 1H), 3.46-3.28 (m, 2H), 3.24-3.12 (m, 1H), 3.06 (t, J=8.7 Hz, 1H), 2.78-2.62 (m, 1H), 2.50 (dd, J=9.6, 1.5 Hz, 1H), 2.49-2.40 (m, 1H), 2.36-2.21 (m, 1H), 1.55 (d, J=4.4 Hz, 9H), 1.37 (dd, J=14.3, 5.4 Hz, 3H); MS (ESI$^+$) m/z 331 [M+H]$^+$.

Example 20C (3aS,6aS)-5-((R)-1-phenylethyl)hexahydropyrrolo[3,4-c]pyrrol-1(2H)-one To a solution of the titled compound of Example 20B (8.46 g, 20.48 mmol) in CH$_2$Cl$_2$ (50 mL) at 0° C. was added 2,2,2-trifluoroacetic acid (28.4 mL, 369 mmol) dropwise over 30 minutes. The ice-bath was removed after the addition was complete, and the mixture was allowed to stir at ambient temperature for 16 h. The mixture was concentrated under reduced pressure, and the residue was dissolved in CH$_2$Cl$_2$. To this solution was added 10% aqueous NaOH, and the layers were separated. The aqueous layer was extracted with CH$_2$Cl$_2$ (3×10 mL), and the combined organic fractions were dried over anhydrous Na$_2$SO$_4$, filtered and concentrated under reduced pressure to give the titled compound (4.65 g, 20.19 mmol, 99% yield). MS (ESI$^+$) m/z 231 [M+H]$^+$.

Example 20D (3aR,6aS)-2-[1-(2-fluorophenyl)-1H-indazol-4-yl]-5-[(1R)-1-phenylethyl]hexahydropyrrolo[3,4-c]pyrrol-1(2H)-one A flask with the product of Example 9C (5 g, 17.18 mmol), the product of Example 20C (4.75 g, 20.61 mmol), CuI (0.16 g, 0.86 mmol) and potassium phosphate tribasic (7.69 g, 36.1 mmol) was degassed three times with a nitrogen backflush each time. Trans-N,N'-dimethylcyclohexane-1,2-diamine (0.54 mL, 3.44 mmol) and dioxane (45 mL) were added. The mixture was warmed to 110° C. and was allowed to stir for 18 h. The material was allowed to cool to ambient temperature and then was filtered through diatomaceous earth with ethyl acetate. The filtrate was concentrated under reduced pressure, and the residue was purified via column chromatography (SiO$_2$, 5% ethyl acetate/hexanes to 65% ethyl acetate/hexanes) to give the titled compound (4.9 g, 11.12 mmol, 65% yield). MS (ESI$^+$) m/z 441 [M+H]$^+$.

Example 20E (3aR,6aS)-2-[1-(2-fluorophenyl)-1H-indazol-4-yl]hexahydropyrrolo[3,4-c]pyrrol-1(2H)-one The product of Example 20D (4.9 g, 11.1 mmol) and ethanol (150 mL) were added to 20% Pd(OH)$_2$/C, wet (1.0 g, 0.726 mmol) in a 250 mL stainless steel pressure bottle, and the mixture was stirred under hydrogen (30 psi) at 50° C. for 16 h. The mixture was allowed to cool to ambient temperature and was filtered through a nylon membrane. The filtrate was concentrated under reduced pressure to give the titled compound (3.5 g, 10.4 mmol, 94% yield) which as carried on without purification. MS (ESI$^+$) m/z 337 [M+H]$^+$.

Example 20F (3aR,6aS)-2-[1-(2-fluorophenyl)-1H-indazol-4-yl]-5-isobutyrylhexahydropyrrolo[3,4-c]pyrrol-1(2H)-one A mixture of triethylamine (0.15 mL, 1.08 mmol), the product of Example 20E (0.12 g, 0.36 mmol) and isobutyryl chloride (0.06 mL, 0.57 mmol) in CH$_2$Cl$_2$ (2.0 mL) were processed as described in Example 14 to give the titled compound (0.102 g, 0.25 mmol, 70% yield). $^1$H NMR (400 MHz, DMSO-d$_6$) δ ppm 8.21 (dd, J=16.6, 7.3 Hz, 1H), 7.78-7.65 (m, 1H), 7.64-7.52 (m, 2H), 7.52-7.40 (m, 2H), 7.28 (td, J=8.1, 3.4 Hz, 2H), 4.39-4.28 (m, 1H), 3.98 (dd, J=10.4, 7.7 Hz, 1H), 3.91-3.84 (m, 0.5H), 3.84-3.74 (m, 2H), 3.60-3.45 (m, 1.5H), 3.44-3.33 (m, 1H), 3.30-3.10 (m, 1H), 2.81-2.63 (m, 1H), 1.07-0.96 (m, 6H); MS (ESI$^+$) m/z 407 [M+H]$^+$.

Example 21

(3aS,6aS)-2-[1-(2-fluorophenyl)-1H-indazol-4-yl]-5-(isobutylsulfonyl)hexahydropyrrolo[3,4-c]pyrrol-1(2H)-one Triethylamine (0.15 mL, 1.08 mmol) was added to a solution of the product of Example 20E (0.12 g, 0.36 mmol) and isobutanesulfonyl chloride (Acros, 0.090 g, 0.57 mmol) in CH$_2$Cl$_2$ (2.0 mL). The reaction mixture was stirred at ambient temperature for 2 h when additional isobutanesulfonyl chloride (0.090 g, 0.57 mmol) was added. The mixture was stirred for an additional 1 h and was then quenched with water (10 mL). The layers were separated, and the organic layer was washed with brine (1×5 mL) and concentrated under reduced pressure. The residue was purified via column chromatography (SiO$_2$, 100% ethyl acetate to 10% ethanol/ethyl acetate). The resulting material contained residual triethylamine, so the material was dissolved in ethyl acetate (10 mL), washed with 1 N HCl (2×5 mL) and brine (1×5 mL), dried over anhydrous MgSO$_4$, filtered, and concentrated under reduced pressure. The residue was again purified via column chromatography (same conditions as above). Residual impurities remained, so the material was dissolved in CH$_2$Cl$_2$ (10 mL) and was washed with saturated, aqueous NaCO$_3$ (2×5 mL), saturated, aqueous NH$_4$Cl (2×5 mL) and brine (1×5 mL). The organic layer was dried over anhydrous MgSO$_4$, filtered and concentrated under reduced pressure to give the titled compound (0.057 g, 0.124 mmol, 35% yield). $^1$H NMR (400 MHz, DMSO-d$_6$) δ ppm 8.26 (dd, J=15.1, 0.8 Hz, 1H), 7.78-7.66 (m, 1H), 7.64-7.52 (m, 2H), 7.52-7.41 (m, 2H), 7.31-7.24 (m, 2H), 4.38-4.30 (m, 1H), 3.84-3.78 (m, 1H), 3.70 (d, J=9.6 Hz, 1H), 3.65 (dd, J=10.4, 8.6 Hz, 1H), 3.56-3.44 (m, 2H), 3.40-3.34 (m, 1H), 3.28-3.18 (m, 1H), 3.09-2.98 (m, 2H), 2.13 (dp, J=13.3, 6.7 Hz, 1H), 1.06-1.01 (m, 6H); MS (ESI$^+$) m/z 457 [M+H]$^+$.

Example 22

(3aS,6aS)-2-[1-(2-fluorophenyl)-1H-indazol-4-yl]-5-(methylsulfonyl)hexahydropyrrolo[3,4-c]pyrrol-1(2H)-one Triethylamine (0.2 mL, 1.4 mmol) was added to a solution of the product of Example 20E (0.1125 g, 0.334 mmol) and methanesulfonyl chloride (0.05 mL, 0.65 mmol) in CH$_2$Cl$_2$ (1.5 mL). The reaction mixture was stirred at ambient temperature for 45 minutes and then was quenched with water (1×5 mL). The phases were separated, and the organic fraction was washed with saturated, aqueous NH$_4$Cl (2×5 mL) and brine (1×5 mL). The organic layer was concentrated under reduced pressure, and the residue was purified via column chromatography (SiO$_2$, 100% ethyl acetate to 10% ethanol/ethyl acetate) to give the titled compound (0.098 g, 0.236 mmol, 71% yield). $^1$H NMR (400 MHz, DMSO-d$_6$) δ ppm 8.26 (d, J=15.8 Hz, 1H), 7.78-7.66 (m, 1H), 7.64-7.53 (m, 2H), 7.53-7.40 (m, 2H), 7.33-7.24 (m, 2H), 4.38-4.28 (m, 1H), 3.87-3.79 (m, 1H), 3.69-3.59 (m, 2H), 3.55-3.46 (m, 2H), 3.38-3.33 (m, 1H), 3.29-3.20 (m, 1H), 2.98 (s, 3H); MS (ESI$^+$) m/z 415 [M+H]$^+$.

Example 23

(3aS,6aS)-5-(ethylsulfonyl)-2-[1-(2-fluorophenyl)-1H-indazol-4-yl]hexahydropyrrolo[3,4-c]pyrrol-1(2H)-one Triethylamine (0.2 mL, 1.44 mmol), the product of Example 20E (0.12 g, 0.36 mmol) and ethanesulfonyl chloride (Alfa Aesar, 0.05 mL, 0.53 mmol) in CH$_2$Cl$_2$ (1.5 mL) were processed as described in Example 22 to give the titled compound (0.109 g, 0.26 mmol, 70% yield). $^1$H NMR (400 MHz, DMSO-d$_6$) δ ppm 8.26 (d, J=15.3 Hz, 1H), 7.78-7.66 (m, 1H), 7.65-7.53 (m, 2H), 7.52-7.41 (m, 2H), 7.27 (dd, J=8.0, 3.8 Hz, 2H), 4.39-4.29 (m, 1H), 3.84-3.77 (m, 1H), 3.72 (d, J=9.7 Hz, 1H), 3.66 (dd, J=10.3, 8.6 Hz, 1H), 3.58-3.51 (m, 1H), 3.48 (t, J=7.7 Hz, 1H), 3.38 (dd, J=10.4, 5.2 Hz, 1H), 3.29-3.21 (m, 1H), 3.17 (q, J=7.3 Hz, 2H), 1.23 (t, J=7.3 Hz, 3H); MS (ESI$^+$) m/z 429 [M+H]$^+$.

Example 24

(3aS,6aS)-2-[1-(2-fluorophenyl)-1H-indazol-4-yl]-5-(isopropylsulfonyl)hexahydropyrrolo[3,4-c]pyrrol-1(2H)-one Triethylamine (0.2 mL, 1.44 mmol), the product of Example 20E (0.116 g, 0.35 mmol) and isopropylsulfonyl chloride (0.07 mL, 0.63 mmol) in CH$_2$Cl$_2$ (1.5 mL) were processed as described in Example 22 to give the titled compound (0.09 g, 0.196 mmol, 57% yield). $^1$H NMR (400 MHz, DMSO-d$_6$) δ ppm 8.27 (d, J=14.5 Hz, 1H), 7.78-7.66 (m, 1H), 7.64-7.52 (m, 2H), 7.52-7.40 (m, 2H), 7.30-7.21 (m, 2H), 4.40-4.32 (m, 1H), 3.84-3.73 (m, 2H), 3.68 (dd, J=10.4, 8.6 Hz, 1H), 3.55 (dd, J=10.0, 7.4 Hz, 1H), 3.50-3.39 (m, 3H), 3.28-3.18 (m, 1H), 1.25 (d, J=6.7 Hz, 6H); MS (ESI$^+$) m/z 443 [M+H]$^+$.

Example 25

(3aR,6aS)-5-(1-benzofuran-3-ylacetyl)-2-[1-(2-fluorophenyl)-1H-indazol-4-yl]hexahydropyrrolo[3,4-c]pyrrol-1(2H)-one A mixture of N-ethyl-N-isopropylpropan-2-amine (0.2 mL, 1.15 mmol), benzo[b]furan-3-ylacetic acid (BBB-Sci, 0.077 g, 0.44 mmol), the product of Example 20E (0.11 g, 0.33 mmol) and (dimethylamino)-N,N-dimethyl(3-oxido-1H-[1,2,3]triazolo[4,5-b]pyridin-1-yl)methaniminium hexafluorophosphate (HATU, 0.1606 g, 0.422 mmol) in tetrahydrofuran (1.5 mL) was processed as described in Example 10B to give the titled compound (0.115 g, 0.23 mmol, 71% yield). $^1$H NMR (500 MHz, DMSO-d$_6$) δ ppm 8.25 (d, J=20.8 Hz, 1H), 7.89 (d, J=16.7 Hz, 1H), 7.78-7.67 (m, 1H), 7.66-7.51 (m, 4H), 7.52-7.42 (m, 2H), 7.34-7.19 (m, 4H), 4.38-4.30 (m, 1H), 4.13-4.06 (m, 1H), 3.92 (q, J=8.9 Hz, 2H), 3.80 (dd, J=14.8, 7.7 Hz, 3H), 3.62 (ddd, J=17.6, 11.6, 7.5 Hz, 1H), 3.48 (dt, J=14.8, 7.1 Hz, 1H), 3.36-3.12 (m, 1H); MS (ESI$^+$) m/z 495 [M+H]$^+$.

Example 26

(3aS,6aS)-2-[1-(2-fluorophenyl)-1H-indazol-4-yl]-5-[(3,3,3-trifluoropropyl)sulfonyl]hexahydropyrrolo[3,4-c]pyrrol-1(2H)-one Triethylamine (0.06 mL, 0.43 mmol), the product of Example 20E (0.036 g, 0.11 mmol) and 3,3,3-trifluoropropane-1-sulfonyl chloride (0.031 g, 0.16 mmol) in CH$_2$Cl$_2$ (1.0 mL) were processed as described in Example 22 to give the titled compound (0.0072 g, 0.015 mmol, 14% yield). $^1$H NMR (500 MHz, DMSO-d$_6$) δ ppm 8.27 (d, J=18.6 Hz, 1H), 7.78-7.66 (m, 1H), 7.65-7.53 (m, 2H), 7.53-7.41 (m, 2H), 7.32-7.25 (m, 2H), 4.38-4.31 (m, 1H), 3.85-3.79 (m, 1H), 3.75 (dd, J=15.1, 6.6 Hz, 2H), 3.62 (dd, J=10.1, 7.6 Hz, 1H), 3.53-3.39 (m, 4H), 3.29-3.20 (m, 1H), 2.79-2.66 (m, 2H); MS (ESI$^+$) m/z 497 [M+H]$^+$.

Example 27

(3aS,6aS)-2-[1-(2-fluorophenyl)-1H-indazol-4-yl]-5-(pyridin-3-ylsulfonyl)hexahydropyrrolo[3,4-c]pyrrol-1(2H)-one Triethylamine (0.20 mL, 1.44 mmol), the product of Example 20E (0.11 g, 0.33 mmol) and pyridine-3-sulfonyl chloride (ArkPharm, Inc., 0.14 g, 0.79 mmol) in CH$_2$Cl$_2$ (1.5 mL) were processed as described in Example 22 to give the titled compound (0.11 g, 0.23 mmol, 70% yield). $^1$H NMR (500 MHz, DMSO-d$_6$) δ ppm 9.02 (d, J=2.0 Hz, 1H), 8.96-8.89 (m, 1H), 8.31-8.23 (m, 1H), 7.98 (d, J=15.8 Hz, 1H), 7.78-7.66 (m, 2H), 7.64-7.53 (m, 2H), 7.52-7.41 (m, 2H), 7.26 (dd, J=8.4, 2.7 Hz, 2H), 7.16 (d, J=7.5 Hz, 1H), 4.34-4.24 (m, 1H), 3.80-3.72 (m, 1H), 3.69 (d, J=9.6 Hz, 1H), 3.49 (dd, J=10.1, 8.8 Hz, 1H), 3.44-3.35 (m, 2H), 3.30 (dd, J=10.4, 5.7 Hz, 1H), 3.18-3.06 (m, 1H); MS (ESI$^+$) m/z 478 [M+H]$^+$.

Example 28

(3aS,6aS)-5-(cyclopropylsulfonyl)-2-[1-(2-fluorophenyl)-1H-indazol-4-yl]hexahydropyrrolo[3,4-c]pyrrol-1(2H)-one Triethylamine (0.2 mL, 1.435 mmol), the product of Example 20E (0.11 g, 0.32 mmol) and cyclopropanesulfonyl chloride (0.06 mL, 0.60 mmol) in CH$_2$Cl$_2$ (1.5 mL) were processed as described in Example 22 to give the titled compound (0.104 g, 0.24 mmol, 74% yield). $^1$H NMR (400 MHz, DMSO-d$_6$) δ ppm 8.25 (d, J=15.5 Hz, 1H), 7.79-7.65 (m, 1H), 7.65-7.52 (m, 2H), 7.52-7.40 (m, 2H), 7.32-7.24 (m, 2H), 4.38-4.29 (m, 1H), 3.86-3.79 (m, 1H), 3.69 (dd, J=10.1, 8.7 Hz, 2H), 3.58 (t, J=8.8 Hz, 1H), 3.54-3.46 (m, 1H), 3.38 (dd, J=10.4, 5.2 Hz, 1H), 3.29-3.19 (m, 1H), 2.80-2.70 (m, 1H), 1.05-0.93 (m, 4H); MS (ESI$^+$) m/z 441 [M+H]$^+$.

Example 29

(3aS,6aS)-2-[1-(2-fluorophenyl)-1H-indazol-4-yl]-5-(phenylsulfonyl)hexahydropyrrolo[3,4-c]pyrrol-1(2H)-one Triethylamine (0.2 mL, 1.435 mmol), the product of Example 20E (0.10 g, 0.30 mmol) and benzenesulfonyl chloride (0.08 mL, 0.62 mmol) in CH$_2$Cl$_2$ (1.5 mL) were processed as described in Example 22 to give the titled compound (0.107 g, 0.225 mmol, 75% yield). $^1$H NMR (400 MHz, DMSO-d$_6$) δ ppm 7.94 (d, J=11.5 Hz, 1H), 7.85 (d, J=7.4 Hz, 2H), 7.81-7.73 (m, 1H), 7.68 (dd, J=7.7, 7.1 Hz, 3H), 7.64-7.53 (m, 2H), 7.52-7.41 (m, 2H), 7.26 (dd, J=8.4, 2.8 Hz, 1H), 7.16 (d, J=7.5 Hz, 1H), 4.32-4.24 (m, 1H), 3.76-3.68 (m, 1H), 3.62 (d, J=8.8 Hz, 1H), 3.44-3.34 (m, 2H), 3.30-3.26 (m, 1H), 3.26-3.19 (m, 1H), 3.14-3.03 (m, 1H); MS (ESI$^+$) m/z 477 [M+H]$^+$.

Example 30 tert-butyl 4-{[(3aS,6aS)-5-[1-(2-fluorophenyl)-1H-indazol-4-yl]-4-oxohexahydropyrrolo[3,4c]-pyrrol-2(1H)-yl]sulfonyl}piperidine-1-carboxylate Triethylamine (0.35 mL, 2.51 mmol), the product of Example 20E (0.211 g, 0.63 mmol) and 4-chlorosulfonylpiperidine-1-carboxylic acid tert-butyl ester (Hande Sci., 0.38 g, 1.33 mmol) in CH$_2$Cl$_2$ (3.0 mL) were processed as described in Example 22 to give the titled compound (0.23 g, 0.394 mmol, 63% yield). $^1$H NMR (400 MHz, DMSO-d$_6$) δ ppm 8.27 (d, J=14.1 Hz, 1H), 7.79-7.66 (m, 1H), 7.65-7.52 (m, 2H), 7.52-7.42 (m, 2H), 7.31-7.23 (m, 2H), 4.41-4.32 (m, 1H), 4.07-3.94 (m, 2H), 3.84-3.74 (m, 2H), 3.70 (dd, J=10.4, 8.6 Hz, 1H), 3.58 (dd, J=10.1, 7.5 Hz, 1H), 3.52 (dt, J=11.8, 3.5 Hz, 1H), 3.49-3.42 (m, 2H), 3.29-3.17 (m, 1H), 2.77 (s, 2H), 2.00-1.91 (m, 2H), 1.55-1.40 (m, 2H), 1.38 (s, 9H); MS (ESI$^-$) m/z 582 (M–H)$^-$.

Example 31

(3aR,6aS)-2-[1-(2-fluorophenyl)-1H-indazol-4-yl]-5-{[2-(pyrrolidin-1-ylmethyl)-1,3-oxazol-4-yl]carbonyl}hexahydropyrrolo[3,4-c]pyrrol-1(2H)-one A mixture of N-ethyl-N-isopropylpropan-2-amine (0.2 mL, 1.15 mmol), the product of Example 20E (0.113 g, 0.335 mmol), 2-(pyrrolidine-1-ylmethyl)-1,3-oxazole-4-carboxylaic acid (SpeedChem, 0.087 g, 0.445 mmol) and (dimethylamino)-N,N-dimethyl(3-oxido-1H-[1,2,3]triazolo[4,5-b]pyridin-1-yl)methaniminium hexafluorophosphate (HATU, 0.156 g, 0.410 mmol) in tetrahydrofuran (1.5 mL) were processed as described in Example 10B to give the titled compound (0.072 g, 0.14 mmol, 42% yield). $^1$H NMR (400 MHz, DMSO-d$_6$) δ ppm 8.58 (d, J=8.4 Hz, 1H), 8.31-8.19 (m, 1H), 7.78-7.64 (m, 1H), 7.64-7.51 (m, 2H), 7.51-7.39 (m, 2H), 7.30 (d, J=7.5 Hz, 1H), 7.26 (dd, J=8.4, 2.9 Hz, 1H), 4.51-4.31 (m, 2H), 4.12-3.96 (m, 1H), 3.90-3.72 (m, 4H), 3.61-3.41 (m, 2H), 3.26-3.14 (m, 1H), 2.60-2.52 (m, 4H), 1.76-1.60 (m, 4H); MS (ESI$^+$) m/z 515 [M+H]$^+$.

Example 32

(3aR,6aS)-2-[1-(2-fluorophenyl)-1H-indazol-4-yl]-5-(tetrahydrofuran-3-ylcarbonyl)hexahydropyrrolo[3,4-c]pyrrol-1(2H)-one A mixture of N-ethyl-N-isopropylpropan-2-amine (0.2 mL, 1.15 mmol), the product of Example 20E (0.109 g, 0.32 mmol), tetrahydrofuran-2-carboxylic acid (0.048 g, 0.415 mmol) and (dimethylamino)-N,N-dimethyl(3-oxido-1H-[1,2,3]triazolo[4,5-b]pyridin-1-yl)methaniminium hexafluorophosphate (HATU, 0.153 g, 0.403 mmol) in tetrahydrofuran (1.5 mL) were processed as described in Example 10B to give the titled compound (0.076 g, 0.174 mmol, 54% yield). $^1$H NMR (400 MHz, DMSO-d$_6$) δ ppm 8.29-8.21 (m, 1H), 7.78-7.65 (m, 1H), 7.64-7.54 (m, 2H), 7.54-7.41 (m, 2H), 7.32-7.23 (m, 2H), 4.38-4.28 (m, 1H), 4.06-3.96 (m, 1H), 3.96-3.85 (m, 2H), 3.85-3.76 (m, 2H), 3.77-3.64 (m, 3H), 3.63-3.46 (m, 1H), 3.44-3.34 (m, 1H), 3.30-3.10 (m, 2H), 2.15-1.91 (m, 2H); MS (ESI$^+$) m/z 435 [M+H]$^+$.

Example 33

(3aR,6aS)-5-[(3,5-dimethyl-1,2-oxazol-4-yl)acetyl]-2-[1-(2-fluorophenyl)-1H-indazol-4-yl]hexahydropyrrolo[3,4-c]pyrrol-1(2H)-one A mixture of N-ethyl-N-isopropylpropan-2-amine (0.2 mL, 1.15 mmol), the product of Example 20E (0.105 g, 0.31 mmol), (3,5-dimethylisoxazol-4-yl)-acetic acid (CombiBlocks, 0.064 g, 0.41 mmol) and (dimethylamino)-N,N-dimethyl(3-oxido-1H-[1,2,3]triazolo[4,5-b]pyridin-1-yl)methaniminium hexafluorophosphate (HATU, 0.15 g, 0.39 mmol) in tetrahydrofuran (2.0 mL) were processed as described in Example 10B to give the titled compound (0.104 g, 0.198 mmol, 64% yield). $^1$H NMR (400 MHz, DMSO-d$_6$) δ ppm 8.31-8.24 (m, 1H), 7.79-7.65 (m, 1H), 7.65-7.53 (m, 2H), 7.53-7.42 (m, 2H), 7.34-7.24 (m, 2H), 4.39-4.30 (m, 1H), 4.09-4.00 (m, 1H), 3.97-3.78 (m, 2H), 3.66-3.52 (m, 2H), 3.48 (d, J=7.4 Hz, 1H), 3.46-3.39 (m, 2H), 3.24-3.08 (m, 1H), 2.28 (d, J=11.1 Hz, 3H), 2.09 (d, J=7.9 Hz, 3H); MS (ESI$^+$) m/z 474 [M+H]$^+$.

Example 34

(3aS,6aR)-2-[1-(2-fluorophenyl)-1H-indazol-4-yl]-5-[(3S)-3-hydroxybutanoyl]hexahydropyrrolo[3,4-c]pyrrol-1(2H)-one

Example 34A (3aR,6aR)-5-((R)-1-phenylethyl)hexahydropyrrolo[3,4-c]pyrrol-1(2H)-one A mixture of the product of Example 20A (21.5 g, 65.1 mmol) and 2,2,2-trifluoroacetic acid (90 mL, 1171 mmol) in CH$_2$Cl$_2$ (200 mL) was process as described in Example 20C to give the titled compound (15 g, 65.1 mmol, 100% yield). MS (ESI$^+$) m/z 231 [M+H]$^+$.

Example 34B (3aS,6aR)-2-[1-(2-fluorophenyl)-1H-indazol-4-yl]-5-[(1R)-1-phenylethyl]hexahydropyrrolo[3,4-c]pyrrol-1(2H)-one The product of Example 9C (19 g, 65.3 mmol), the product of Example 34A (15.03 g, 65.3 mmol), CuI (0.62 g, 3.26 mmol), potassium phosphate tribasic (29.1 g, 137 mmol) and trans-N,N'-dimethylcyclohexane-1,2-diamine (1.9 mL, 13.05 mmol) in dioxane (200 mL) were processed as described in Example 20D to give the titled compound (25.1 g, 57 mmol, 87% yield). MS (ESI$^+$) m/z 441 [M+H]$^+$.

Example 34C (3aS,6aR)-2-[1-(2-fluorophenyl)-1H-indazol-4-yl]hexahydropyrrolo[3,4-c]pyrrol-1(2H)-one To a solution of the product of Example 34B (24.1 g, 54.7 mmol) in CH$_2$Cl$_2$ (200 mL) at 0° C. was added 1-chloroethyl chloroformate (23.9 mL, 219 mmol). The mixture was stirred at 0° C. for 1 h and then was allowed to warm to ambient temperature and was stirred for 2 h. The mixture was warmed to 50° C., was stirred for an additional 1 h then was allowed to cool to ambient temperature and was concentrated under reduced pressure. The residue was dissolved in methanol (100 mL), and the mixture was warmed to reflux. The solution was stirred at reflux for 2 h and then was allowed to stir overnight at ambient temperature. The mixture was concentrated under reduced pressure, and the residue was purified via column chromatography (SiO$_2$, 5% ethyl acetate/heptanes to 100% ethyl acetate to 9:1:0.1 ethyl acetate/methanol/triethylamine) to give the titled compound (13.5 g, 40.1 mmol, 73.4% yield). MS (ESI$^+$) m/z 337 [M+H]$^+$.

Example 34D (3aS,6aR)-2-[1-(2-fluorophenyl)-1H-indazol-4-yl]-5-[(3S)-3-hydroxybutanoyl]hexahydropyrrolo[3,4-c]pyrrol-1(2H)-one To a solution of the product of Example 34C (3 g, 8.92 mmol), (S)-3-hydroxybutyric acid (1.0 g, 9.6 mmol) and N-ethyl-N-isopropylpropan-2-amine (6.23 mL, 35.7 mmol) in tetrahydrofuran (70 mL) was added (dimethylamino)-N,N-dimethyl(3-oxido-1H-[1,2,3]triazolo[4,5-b]pyridin-1-yl)methaniminium hexafluorophosphate (HATU, 3.73 g, 9.81 mmol). This mixture was allowed to stir at ambient temperature for 3 h and then was quenched with H$_2$O (15 mL) and diluted with ethyl acetate (15 mL). The layers were separated, and the aqueous layer was extracted with ethyl acetate (3×5 mL). The combined organic fractions were dried over anhydrous Na$_2$SO$_4$, filtered, concentrated. The residue was purified via column chromatography (SiO$_2$, 20% hexanes/ethyl acetate to 100% ethyl acetate to 9:1:0.1 ethyl acetate/methanol/triethylamine) to provide the titled compound (2 g, 4.73 mmol, 53% yield). $^1$H NMR (500 MHz, DMSO-d$_6$) δ ppm 8.28 (dd, J=4.0, 0.8 Hz, 1H), 7.69 (td, J=7.8, 1.4 Hz, 1H), 7.63-7.53 (m, 2H), 7.51-7.42 (m, 2H), 7.29 (d, J=7.8 Hz, 1H), 7.27-7.25 (m, 1H), 4.64 (dd, J=4.5, 1.3 Hz, 1H), 4.33 (dt, J=9.9, 6.0 Hz, 1H), 4.07-3.98 (m, 1H), 3.98-3.85 (m, 2H), 3.80 (d, J=10.3 Hz, 1H), 3.59-3.36 (m, 2H), 3.32-3.09 (m, 2H), 2.44 (ddd, J=14.9, 7.3, 1.5 Hz, 1H), 2.32 (ddd, J=28.5, 14.9, 5.3 Hz, 1H), 1.11 (dd, J=8.2, 6.2 Hz, 3H); MS (ESI$^+$) m/z 423 [M+H]$^+$.

Example 35

(3aS,6aR)-2-[1-(2-fluorophenyl)-1H-indazol-4-yl]-5-(3-hydroxy-3-methylbutanoyl)hexahydropyrrolo[3,4-c]pyrrol-1(2H)-one To a solution of the product of Example 34C (1.36 g, 4.04 mmol), beta-hydroxyisovaleric acid (0.48 mL, 4.45 mmol) and N-ethyl-N-isopropylpropan-2-amine (2.8 mL, 16.2 mmol) in tetrahydrofuran (30 mL) was added (dimethylamino)-N,N-dimethyl(3-oxido-1H-[1,2,3]triazolo[4,5-b]pyridin-1-yl)methaniminium hexafluorophosphate (HATU, 1.69 g, 4.45 mmol) portionwise over 15 minutes. This mixture was allowed to stir at ambient temperature for 3 h and then was quenched with H$_2$O (10 mL) and diluted with ethyl acetate (10 mL). The layers were separated, and the aqueous layer was extracted with ethyl acetate (3×10 mL). The combined organic fractions were dried over anhydrous Na$_2$SO$_4$, filtered and concentrated. The residue was purified via column chromatography (SiO$_2$, 20% hexanes/ethyl acetate to 100% ethyl acetate to 15% methanol in ethyl acetate) to provide the titled compound (1.2 g, 2.75 mmol, 68% yield). $^1$H NMR (400 MHz, DMSO-d$_6$) δ ppm 8.27 (dd, J=2.9, 0.7 Hz, 1H), 7.68 (td, J=7.9, 1.5 Hz, 1H), 7.64-7.52 (m, 2H), 7.52-7.42 (m, 2H), 7.31-7.22 (m, 2H), 4.84 (d, J=11.3 Hz, 1H), 4.33 (ddd, J=9.9, 6.2, 3.8 Hz, 1H), 4.04-3.96 (m, 1H), 3.93-3.85 (m, 1H), 3.82-3.78 (m, 2H), 3.61-3.37 (m, 2H), 3.31-3.11 (m, 1H), 2.48-2.36 (m, 2H), 1.19 (t, J=5.7 Hz, 6H); MS (ESI$^-$) m/z 435 (M−H)$^-$.

Example 36

(3aR,6aS)-2-[1-(2-fluorophenyl)-1H-indazol-4-yl]-5-[(3S)-3-hydroxybutanoyl]hexahydropyrrolo[3,4-c]pyrrol-1(2H)-one To a solution of the product of Example 20E (0.2 g, 0.60 mmol), (S)-3-hydroxybutyric acid (0.068 g, 0.65 mmol) and Hunig's base (0.415 mL, 2.4 mmol) in tetrahydrofuran (5 mL) was added (dimethylamino)-N,N-dimethyl(3-oxido-1H-[1,2,3]triazolo[4,5-b]pyridin-1-yl)methaniminium hexafluorophosphate (HATU, 0.249 g, 0.654 mmol). This mixture was allowed to stir at ambient temperature for 16 h and then was quenched with H$_2$O (5 mL) and diluted with ethyl acetate (10 mL). The layers were separated, and the aqueous layer was extracted with ethyl acetate (3×5 mL). The combined organic fractions were dried over anhydrous Na$_2$SO$_4$, filtered and concentrated. The residue was purified via column chromatography (SiO$_2$, 20% hexanes/ethyl acetate to 100% ethyl acetate to 90% ethyl acetate/methanol) to provide the titled compound (0.10 g, 0.24 mmol, 40% yield). $^1$H NMR (400 MHz, DMSO-d$_6$) δ ppm 8.28 (dd, J=4.5, 0.7 Hz, 1H), 7.68 (t, J=7.8 Hz, 1H), 7.64-7.52 (m, 2H), 7.52-7.41 (m, 2H), 7.33-7.24 (m, 2H), 4.65 (dd, J=6.5, 4.5 Hz, 1H), 4.33 (dt, J=10.0, 6.0 Hz, 1H), 4.08-3.92 (m, 2H), 3.91-3.73 (m, 2H), 3.62-3.35 (m, 2H), 3.30-3.09 (m, 2H), 2.48-2.38 (m, 1H), 2.36-2.25 (m, 1H), 1.11 (dd, J=11.5, 6.2 Hz, 3H); MS (ESI$^+$) m/z 423 [M+H]$^+$.

Example 37

(3aR,6aS)-2-[1-(2-fluorophenyl)-1H-indazol-4-yl]-5-(3-hydroxy-3-methylbutanoyl)hexahydropyrrolo[3,4-c]pyrrol-1(2H)-one The product of Example 20E (0.23 g, 0.68 mmol), beta-hydroxyisovaleric acid (0.089 g, 0.75 mmol), N-ethyl-N- isopropylpropan-2-amine (0.48 mL, 2.74 mmol) and (dimethylamino)-N,N-dimethyl(3-oxido-1H-[1,2,3]triazolo[4,5-b]pyridin-1-yl)methaniminium hexafluorophosphate (HATU, 0.29 g, 075 mmol) in tetrahydrofuran (6 mL) were processed as described in Example 35 to provide the titled compound (0.15 g, 0.34 mmol, 50% yield). $^1$H NMR (500 MHz, DMSO-d$_6$) δ ppm 8.27 (d, J=3.6 Hz, 1H), 7.69 (t, J=7.3 Hz, 1H), 7.63-7.53 (m, 2H), 7.48 (dt, J=15.8, 4.3 Hz, 2H), 7.28 (dt, J=10.4, 5.3 Hz, 2H), 4.85 (d, J=14.3 Hz, 1H), 4.36-4.28 (m, 1H), 4.02-3.97 (m, 1H), 3.93-3.85 (m, 1H), 3.84-3.77 (m, 2H), 3.61-3.36 (m, 2H), 3.30-3.12 (m, 1H), 2.49-2.36 (m, 2H), 1.20 (d, J=8.7 Hz, 6H); MS (ESI$^-$) m/z 435 (M−H)$^-$.

Example 38

(3aS,6aR)-2-[1-(2-fluorophenyl)-1H-indazol-4-yl]-5-[(3R)-3-hydroxybutanoyl]hexahydropyrrolo[3,4-c]pyrrol-1(2H)-one To a solution of the product of Example 34C (0.22 g, 0.65 mmol), (R)-3-hydroxybutyric acid (0.075 g, 0.72 mmol) and triethylamine (0.365 mL, 2.62 mmol) in tetrahydrofuran (5 mL) at ambient temperature was added 2,4,6-tripropyl-1,3,5,2,4,6-trioxatriphosphinane 2,4,6-trioxide (T3P®, 50% weight in ethyl acetate, 0.58 mL, 0.98 mmol) dropwise. The mixture was allowed to stir at ambient temperature for 4 h. The mixture was quenched with water (5 mL) and diluted with ethyl acetate (5 mL). The layers were separated, and the aqueous layer was extracted with ethyl acetate (3×5 mL). The combined organic fractions were dried over anhydrous Na$_2$SO$_4$, filtered, concentrated under reduced pressure. The residue was purified via column chromatography (SiO$_2$, 10% ethyl acetate/heptanes to 100% ethyl acetate to 10% methanol/ethyl acetate) to give the titled compound (0.16 g, 0.38 mmol, 58% yield). $^1$H NMR (400 MHz, DMSO-d$_6$) δ ppm 8.28 (dd, J=4.5, 0.7 Hz, 1H), 7.69 (t, J=7.8 Hz, 1H), 7.65-7.52 (m, 2H), 7.52-7.41 (m, 2H), 7.33-7.22 (m, 2H), 4.65 (dd, J=6.6, 4.4 Hz, 1H), 4.33 (dt, J=10.1, 5.9 Hz, 1H), 4.09-3.93 (m, 2H), 3.92-3.72 (m, 2H), 3.60-3.36 (m, 2H), 3.31-3.09 (m, 2H), 2.48-2.38 (m, 1H), 2.30 (dt, J=14.8, 5.7 Hz, 1H), 1.11 (dd, J=11.4, 6.2 Hz, 3H); MS (ESI$^+$) m/z 423 [M+H]$^+$.

Example 39

(3aR,6aS)-2-[1-(2-fluorophenyl)-1H-indazol-4-yl]-5-[(3R)-3-hydroxybutanoyl]hexahydropyrrolo[3,4-c]pyrrol-1(2H)-one The product of Example 20E (0.23 g, 0.68 mmol), (R)-3-hydroxybutyric acid (0.078 g, 0.75 mmol), triethylamine (0.38 mL, 2.74 mmol) and 2,4,6-tripropyl-1,3,5,2,4,6-trioxatriphosphinane 2,4,6-trioxide (T3P®, 50% weight in ethyl acetate, 0.611 mL, 1.026 mmol) in tetrahydrofuran (5 mL) were processed as described in Example 38 to give the titled compound (0.17 g, 0.40 mmol, 59% yield). $^1$H NMR (500 MHz, DMSO-d$_6$) δ ppm 8.27 (d, J=4.0 Hz, 1H), 7.69 (t, J=7.3 Hz, 1H), 7.64-7.53 (m, 2H), 7.47 (dt, J=15.6, 7.6 Hz, 2H), 7.31-7.24 (m, 2H), 4.64 (d, J=3.7 Hz, 1H), 4.37-4.28 (m, 1H), 4.07-3.98 (m, 1H), 3.99-3.84 (m, 2H), 3.80 (d, J=10.2 Hz, 1H), 3.59-3.36 (m, 2H), 3.31-3.10 (m, 2H), 2.44 (dd, J=14.0, 7.4 Hz, 1H), 2.32 (ddd, J=28.3, 14.9, 5.3 Hz, 1H), 1.11 (dd, J=8.1, 6.3 Hz, 3H); MS (ESI$^+$) m/z 423 [M+H]$^+$.

Example 40

(3aR,6aS)-5-[(2,2-difluorocyclopropyl)carbonyl]-2-[1-(2-fluorophenyl)-1H-indazol-4-yl]hexahydropyrrolo[3,4-c]pyrrol-1(2H)-one The product of Example 20E (100 mg, 0.30 mmol), 2,2-difluorocyclopropanecarboxylic acid (Matrix, 73 mg, 0.60 mmol), 1-ethyl-3-(3-dimethylaminopropyl)carbodiimide (EDCI, 92 mg, 0.30 mmol) and ethyl (hydroxyimino)cyanoacetate (84 mg, 0.30 mmol) were combined with pyridine (2.0 mL). The reaction mixture was stirred at ambient temperature for 18 hours. The mixture was filtered through a glass microfiber frit and purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (93 mg, 0.21 mmol, 71% yield). $^1$H NMR (400 MHz, DMSO-d$_6$) δ ppm 8.33-8.15 (m, 1H), 7.78-7.66 (m, 1H), 7.64-7.53 (m, 2H), 7.55-7.41 (m, 2H), 7.34-7.23 (m, 2H), 4.41-4.15 (m, 2H), 4.03-3.70 (m, 3H), 3.67-3.37 (m, 2H), 3.28-2.92 (m, 2H), 2.09-1.79 (m, 2H); MS (ESI$^+$) m/z 441 [M+H]$^+$.

Example 41

(3aS,6aR)-2-[1-(2-fluorophenyl)-1H-indazol-4-yl]-5-(2-hydroxy-2-methylpropanoyl)hexahydropyrrolo[3,4-c]pyrrol-1(2H)-one The product of Example 34C (145 mg, 0.43 mmol), 2-hydroxy-2-methylpropanoic acid (90 mg, 0.86 mmol), 1-ethyl-3-(3-dimethylaminopropyl)carbodiimide (EDCI, 134 mg, 0.86 mmol) and ethyl (hydroxyimino)cyanoacetate (123 mg, 0.86 mmol) were combined with pyridine (3.0 mL). The reaction mixture was stirred at ambient temperature for 18 hours. The mixture was filtered through a glass microfiber frit and purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (73 mg, 0.17 mmol, 40% yield). $^1$H NMR (400 MHz, methanol-d$_4$) δ ppm 8.20 (s, 1H), 7.72-7.58 (m, 1H), 7.58-7.52 (m, 1H), 7.52-7.47 (m, 1H), 7.46-7.37 (m, 2H), 7.28 (dd, J=8.5, 2.8 Hz, 1H), 7.25-7.19 (m, J=7.6 Hz, 1H), 4.81-4.44 (m, 1H), 4.40 (dd, J=10.2, 6.3 Hz, 1H), 4.17-3.59 (m, 4H), 3.52-3.16 (m, 2H), 1.44 (s, 6H); MS (ESI$^+$) m/z 423 [M+H]$^+$.

Example 42

(3aS,6aR)-2-[1-(2-fluorophenyl)-1H-indazol-4-yl]-5-[(1-hydroxycyclopropyl)carbonyl]hexahydropyrrolo[3,4-c]pyrrol-1(2H)-one The product of Example 34C (145 mg, 0.43 mmol), 1-hydroxy-1-cyclopropanecarboxylic acid (88 mg, 0.86 mmol), 1-ethyl-3-(3-dimethylaminopropyl)carbodiimide (EDCI, 134 mg, 0.86 mmol) and ethyl (hydroxyimino)cyanoacetate (123 mg, 0.86 mmol) were combined with pyridine (2.0 mL). The reaction mixture was stirred at ambient temperature for 18 hours. The mixture was filtered through a glass microfiber frit and purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (91 mg, 0.22 mmol, 50% yield). $^1$H NMR (400 MHz, Methanol-$d_4$) δ ppm 8.21 (s, 1H), 7.72-7.59 (m, 1H), 7.59-7.53 (m, 1H), 7.53-7.47 (m, 1H), 7.46-7.38 (m, 2H), 7.29 (dd, J=8.4, 2.9 Hz, 1H), 7.23 (d, J=7.3 Hz, 1H), 4.73-4.47 (br s, 1H), 4.41 (dd, J=10.2, 6.3 Hz, 1H), 4.01 (br s, 2H), 3.84 (d, J=10.4 Hz, 1H), 3.77-3.58 (m, 1H), 3.54-3.25 (m, 2H), 1.27-1.15 (m, 1H), 1.10-0.83 (m, 3H); MS (ESI$^+$) m/z 421 [M+H]$^+$.

Example 43

(3aS,6aR)-5-[(3-chlorocyclobutyl)carbonyl]-2-[1-(2-fluorophenyl)-1H-indazol-4-yl]hexahydropyrrolo[3,4-c]pyrrol-1(2H)-one The product of Example 34C (145 mg, 0.43 mmol), 3-chlorocyclobutanecarboxylic acid (Goldenbridge, 116 mg, 0.86 mmol), 1-ethyl-3-(3-dimethylaminopropyl)carbodiimide (EDCI, 134 mg, 0.86 mmol) and ethyl (hydroxyimino)cyanoacetate (123 mg, 0.86 mmol) were combined with pyridine (2.0 mL). The reaction mixture was stirred at ambient temperature for 18 hours. The mixture was filtered through a glass microfiber frit and purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (64 mg, 0.14 mmol, 33% yield). $^1$H NMR (400 MHz, methanol-$d_4$) δ ppm 8.24-8.17 (m, J=10.7 Hz, 1H), 7.66-7.59 (m, 1H), 7.59-7.53 (m, 1H), 7.50 (t, J=8.1 Hz, 1H), 7.46-7.38 (m, 2H), 7.32-7.27 (m, 1H), 7.24 (dd, J=7.3, 1.8 Hz, 1H), 4.64-4.49 (m, 2H), 4.40 (ddd, J=10.3, 6.2, 2.1 Hz, 1H), 4.14-3.91 (m, 2H), 3.84 (t, J=9.92 Hz, 1H), 3.79-3.70 (m, 1H), 3.66-3.43 (m, 3H), 2.92-2.75 (m, 2H), 2.65-2.47 (m, 2H); MS (ESI$^+$) m/z 453 [M+H]$^+$.

Example 44

3-[(3aR,6aS)-5-[1-(2-fluorophenyl)-1H-indazol-4-yl]-4-oxohexahydropyrrolo[3,4-c]pyrrol-2(1H)-yl]-3-oxopropanamide A mixture of the product of Example 34C (0.21 g, 0.624 mmol), 3-amino-3-oxopropanoic acid (ChemBridge, 0.071 g, 0.69 mmol), N-ethyl-N-isopropylpropan-2-amine (0.44 mL, 2.5 mmol) and (dimethylamino)-N,N-dimethyl(3-oxido-1H-[1,2,3]triazolo[4,5-b]pyridin-1-yl)methaniminium hexafluorophosphate (HATU, 0.26 g, 0.69 mmol) in tetrahydrofuran (5 mL) was processed as described in Example 10B to give the titled compound (0.10 g, 0.24 mmol, 38% yield). $^1$H NMR (400 MHz, DMSO-$d_6$) δ ppm 8.31 (d, J=2.6 Hz, 1H), 7.68 (t, J=7.8 Hz, 1H), 7.65-7.52 (m, 3H), 7.52-7.41 (m, 2H), 7.36-7.21 (m, 2H), 7.03 (s, 1H), 4.33 (td, J=9.5, 6.3 Hz, 1H), 4.08-3.75 (m, 3H), 3.61-3.46 (m, 2H), 3.32-3.27 (m, 1H), 3.25 (d, J=4.8 Hz, 2H), 3.21-3.09 (m, 1H); MS (ESI$^+$) m/z 421 [M+H]$^+$.

Example 45

(3aS,6aR)-2-[1-(2-fluorophenyl)-1H-indazol-4-yl]-5-(3-hydroxypropanoyl)hexahydropyrrolo[3,4-c]pyrrol-1(2H)-one Example 45A 3-[(3aR,6aS)-5-[1-(2-fluorophenyl)-1H-indazol-4-yl]-4-oxohexahydropyrrolo[3,4-c]pyrrol-2(1H)-yl]-3-oxopropyl acrylate A mixture of the product of Example 34C (0.30 g, 0.89 mmol), 2-carboxyethyl acrylate (0.10 mL, 1.03 mmol), N-ethyl-N-isopropylpropan-2-amine (0.62 mL, 3.57 mmol) and (dimethylamino)-N,N-dimethyl(3-oxido-1H-[1,2,3]triazolo[4,5-b]pyridin-1-yl)methaniminium hexafluorophosphate (HATU, 0.37 g, 0.98 mmol) in tetrahydrofuran (5 mL) were processed as described in Example 10B to give the titled compound (0.19 g, 0.411 mmol, 46% yield). MS (ESI$^+$) m/z 463 [M+H]$^+$.

Example 45B (3aS,6aR)-2-[1-(2-fluorophenyl)-1H-indazol-4-yl]-5-(3-hydroxypropanoyl)hexahydropyrrolo[3,4-c]pyrrol-1(2H)-one To a solution of the product of Example 45A (0.19 g, 0.41 mmol) in tetrahydrofuran (7 mL) and methanol (7 mL) was added KOH (40% aqueous solution, 5 mL). This mixture was allowed to stir at ambient temperature for 6 h and then was concentrated under reduced pressure. The residue was partitioned between $CH_2Cl_2$ (10 mL) and $H_2O$ (7 mL). The layers were separated, and the aqueous layer was extracted with $CH_2Cl_2$ (3×5 mL). The combined organic fractions were dried over anhydrous $Na_2SO_4$, filtered, concentrated under reduced pressure. The residue was purified by preparative HPLC [Waters XBridge™ C18 5 μm OBD™ column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (20 mg, 0.049 mmol, 12% yield). $^1$H NMR (500 MHz, DMSO-$d_6$) δ ppm 8.28 (d, J=4.7 Hz, 1H), 7.68 (t, J=7.6 Hz, 1H), 7.63-7.53 (m, 2H), 7.52-7.42 (m, 2H), 7.30 (d, J=7.5 Hz, 1H), 7.27 (dd, J=8.8, 3.1 Hz, 1H), 4.54 (dt, J=7.9, 5.4 Hz, 1H), 4.37-4.28 (m, 1H), 3.99-3.90 (m, 1H), 3.91-3.84 (m, 1H), 3.81-3.78 (m, 1H), 3.69-3.61 (m, 2H), 3.61-3.36 (m, 2H), 3.30-3.08 (m, 2H), 2.46 (dd, J=14.0, 7.4 Hz, 2H).); MS (ESI$^+$) m/z 409 [M+H]$^+$.

Example 46

(3aS,6aR)-5-acetyl-2-[1-(2-fluorophenyl)-1H-indazol-4-yl]hexahydropyrrolo[3,4-c]pyrrol-1(2H)-one To a solution of beta-hydroxyisovaleric acid (3.59 mL, 33.4 mmol, 45% acetic acid impurity) and the product of Example 34C (10.2 g, 30.4 mmol) in N,N-dimethylformamide (130 mL) at 4° C. was added N,N-diisopropylethylamine (21.5 mL, 124 mmol) followed by (dimethylamino)-N,N-dimethyl(3-oxido-1H-[1,2,3]triazolo[4,5-b]pyridin-1-yl)methaniminium hexafluorophosphate (HATU, 12.7 g, 33.4 mmol) in N,N-dimethylformamide (100 mL) dropwise. The HATU was added over 60 minutes, and the temperature increased to 9.4° C. after the addition was complete. The reaction mixture was allowed to stir for 15 minutes and then was poured into saturated, aqueous $NaHCO_3$ (100 mL) and was stirred for 5 minutes. The layers were separated, and the aqueous layer was extracted with ethyl acetate (2×100 mL). The combined organic fractions were dried over anhydrous $Na_2SO_4$, filtered and concentrated under reduced pressure. The residue was purified via column chromatography ($SiO_2$, eluted with a gradient 0-100% ethyl acetate over 60 minutes with a 30 minute hold and then eluted with ethyl acetate/10% methanol for 45 minutes with a 60 minute hold) to give the titled compound (4.85 g, 12.82 mmol, 42% yield) from the acetic acid impurity in the beta-hydroxyisovaleric acid. $^1$H NMR (400 MHz, DMSO-$d_6$) δ ppm 8.27 (ddd, J=17.0, 3.7, 0.8 Hz, 1H), 7.81-7.38 (m, 5H), 7.36-7.19 (m, 2H), 4.39-4.20 (m, 1H), 4.10-3.99 (m, 1H), 3.84 (qdd, J=13.2, 10.8, 8.4 Hz, 2H), 3.69 (dd, J=9.7, 3.0 Hz, 1H), 3.61-3.40 (m, 1H), 3.28-3.08 (m, 1H), 2.00 (d, J=8.9 Hz, 3H), 1.28-1.00 (m, 1H); MS (ESI$^+$) m/z 379 [M+H]$^+$.

Example 47

(3aR,6aR)-5-[1-(2-fluorophenyl)-1H-indazol-4-yl]-1-(2-hydroxy-2-methylpropanoyl)hexahydropyrrolo[3,4-b]pyrrol-6(1H)-one To 2-hydroxyisobutyric acid (0.209 g, 2.01 mmol), the product of Example 1Q (0.45 g, 1.34 mmol) and triethylamine (0.224 mL, 1.61 mmol) in acetonitrile (10 mL) was added (dimethylamino)-N,N-dimethyl(3-oxido-1H-[1,2,3]triazolo[4,5-b]pyridin-1-yl)methaniminium hexafluorophosphate (HATU, 0.763 g, 2.007 mmol). The reaction was allowed to stir for 2 hours and then was diluted with ethyl acetate (20 mL) and transferred to an addition funnel. The material was washed with water (20 mL) and brine (20 mL), dried over anhydrous MgSO$_4$, filtered and concentrated under reduced pressure. The residue was purified by column chromatography (SiO$_2$, 10% methanol in ethyl acetate) to afford the titled compound (0.50 g, 1.18 mmol, 88% yield). $^1$H NMR (400 MHz, DMSO-d$_6$) δ ppm 8.32 (s, 1H), 7.69 (td, J=7.8, 1.7 Hz, 1H), 7.65-7.53 (m, 2H), 7.53-7.42 (m, 2H), 7.31 (s, 2H), 5.97-5.09 (m, 2H), 4.53-4.09 (m, 1H), 3.84-3.56 (m, 2H), 3.47 (s, 1H), 3.24-2.91 (m, 1H), 2.23 (s, 1H), 1.97-1.57 (m, 1H), 1.57-1.24 (m, 6H). MS (ESI$^+$) m/z 423 [M+H]$^+$.

Example 48

(3aR,6aR)-5-[1-(2-fluorophenyl)-1H-indazol-4-yl]-1-[(1-hydroxycyclopropyl)carbonyl]hexahydropyrrolo[3,4-b]pyrrol-6(1H)-one To 1-hydroxy-1-cyclopropanecarboxylic acid (0.228 g, 2.23 mmol), the product of Example 1Q (0.50 g, 1.49 mmol) and triethylamine (0.311 mL, 2.23 mmol) in acetonitrile (10 mL) was added (dimethylamino)-N,N-dimethyl(3-oxido-1H-[1,2,3]triazolo[4,5-b]pyridin-1-yl)methaniminium hexafluorophosphate (HATU, 0.85 g, 2.230 mmol). The reaction was allowed to stir for 2 hours and then was diluted with ethyl acetate (20 mL) and transferred to an addition funnel. The material was washed with water (15 mL) and brine (15 mL), dried over anhydrous MgSO$_4$, filtered and concentrated under reduced pressure. The residue was purified by column chromatography (SiO$_2$, 5% methanol in ethyl acetate) to afford the titled compound. (0.40 g, 0.951 mmol, 64% yield). $^1$H NMR (400 MHz, methanol-d$_4$) δ ppm 8.32-8.23 (m, 1H), 7.62 (td, J=7.6, 1.6 Hz, 1H), 7.60-7.46 (m, 2H), 7.46-7.38 (m, 2H), 7.36-7.23 (m, 2H), 5.93-5.65 (m, 1H), 4.39 (dd, J=10.4, 6.5 Hz, 1H), 4.22-3.94 (m, 1H), 3.82 (dd, J=10.1, 1.8 Hz, 1H), 3.74 (s, 1H), 3.49-3.07 (m, 1H), 2.36 (s, 1H), 2.13-1.85 (m, 1H), 1.51-1.21 (m, 2H), 1.12-0.77 (m, 2H); MS (ESI$^+$) m/z 421 [M+H]$^+$.

Example 49

(3aS,6aS)-5-[1-(2-fluorophenyl)-1H-indazol-4-yl]-1-(2-hydroxy-2-methylpropanoyl)hexahydropyrrolo[3,4-b]pyrrol-6(1H)-one To 2-hydroxyisobutyric acid (0.046 g, 0.446 mmol), the product of Example 2I (0.10 g, 0.297 mmol) and triethylamine (0.050 mL, 0.357 mmol) in acetonitrile (2.0 mL) was added (dimethylamino)-N,N-dimethyl(3-oxido-1H-[1,2,3]triazolo[4,5-b]pyridin-1-yl)methaniminium hexafluorophosphate (HATU, 0.17 g, 0.45 mmol). The reaction was allowed to stir for 2 hours and then was diluted with ethyl acetate (10 mL) and transferred to an addition funnel. The material was washed with water (5 mL) and brine (5 mL), dried over anhydrous MgSO$_4$, filtered and concentrated under reduced pressure. The residue was purified by column chromatography (SiO$_2$, 10% methanol in ethyl acetate) to afford the titled compound (0.10 g, 0.237 mmol, 80% yield). $^1$H NMR (400 MHz, DMSO-d$_6$) δ ppm 8.32 (s, 1H), 7.69 (td, J=7.8, 1.7 Hz, 1H), 7.65-7.55 (m, 2H), 7.55-7.42 (m, 2H), 7.36-7.22 (m, 2H), 5.94-5.10 (m, 2H), 4.43-4.15 (m, 1H), 3.74 (d, J=9.7 Hz, 1H), 3.70-3.38 (m, 1H), 3.11 (d, J=79.8 Hz, 1H), 2.23 (s, 1H), 1.97-1.66 (m, 1H), 1.61-1.23 (m, 6H); MS (ESI$^+$) m/z 423 [M+H]$^+$.

Determination of Biological Activity

Abbreviations: CC2-DMPE for N-(6-chloro-7-hydroxycoumarin-3-carbonyl)-dimyristoylphosphatidylethanolamine; DiSBAC$_2$(3) for bis(1,3-diethylthiobarbiturate) trimethine oxonol; DMEM for Dulbecco's Modified Eagle Media; EGTA for ethylene glycol tetraacetic acid; FBS for Fetal Bovine Serum; FLIPR® for Fluorometric Imaging Plate Reader; FRET for Fluorescence Resonance Energy Transfer; HI FBS for Heat-Inactivated Fetal Bovine Serum; HBSS for Hank's Balanced Salt Solution; HEPES for N-2-HydroxyEthylPiperazine-N'-2-Ethane Sulfonic acid; hERG for human Ether-á-go-go-Related Gene; K-aspartate for potassium aspartate; MEM for Minimal Essential Media; MgATP for magnesium adenosine triphosphate; and VABSC-1 for Voltage Assay Background Suppression Compound.

FRET-Based Membrane Potential Assays.

Recombinant, Human Sodium Channel, Na$_v$1.7.

Two days prior to the experiment, frozen HEK293 cells stably expressing recombinant human Na$_v$1.7 were quickly thawed and plated at 25,000 cells/well in growth medium [DMEM (Invitrogen #11965) with 10% HI FBS (Invitrogen #10082), 2 mM glutamine, 100 units/mL penicillin, 0.1 mg/mL streptomycin (PSG, Sigma #G1146), and 500 µg/mL Geneticin (Invitrogen #10131)] in black-walled, clear-bottom 384-well poly-D-lysine-coated assay plates (Greiner Bio-One, Frickenhausen, Germany) and incubated in a humidified 5% CO$_2$ incubator at 37° C. On the day of the assay, medium was removed by aspiration, and cells were washed with assay buffer [HBSS (Invitrogen, Carlsbad, Calif.) containing 20 mM HEPES (Invitrogen, Carlsbad, Calif.)]. After washing, 30 pt assay buffer containing the fluorescent voltage-sensor probe CC2-DMPE (Invitrogen, Carlsbad, Calif.) at 20 µM and 0.01% pluronic F-127 (Invitrogen, Carlsbad, Calif.) was added to the cells. Cells were incubated for 40 minutes at room temperature in the dark. Following the incubation, the cells were washed and 30 pt assay buffer containing 2.5 µM DiSBAC$_2$(3) substrate (Invitrogen, Carlsbad, Calif.) and 0.5 mM VABSC-1 (Invitrogen, Carlsbad, Calif.) was added to the cells. The cells were incubated for 90 minutes at room temperature in the dark. Fluorescence readings were made using a FLIPR®$^{TETRA}$ (Molecular Devices, Sunnyvale Calif.) equipped with voltage-sensor probe optics. At the start of each experiment the optimal (EC$_{80}$) concentration of depolarizing agent (veratridine) was determined by testing a dilution curve of assay buffer containing veratridine (Sigma-Aldrich, St. Louis, Mo.) and 1 mg/mL scorpion venom (SVqq, from Leiurus quinquestriatus; Sigma-Aldrich, St. Louis, Mo.). Compounds were dissolved in dimethyl sulfoxide, and 8-point, 1:3 dilution concentration-response curves were prepared in duplicate in dimethyl sulfoxide, followed by preparation of 0.8 μL/well daughter plates of the dilutions. Test compounds in the daughter plate were diluted to (~3×) solutions in assay buffer immediately before assaying. Using the FLIPR®$^{TETRA}$, 20 μL of the (3×) compound solutions were first added to the cells, then 20 μL of depolarizing solution (3×EC$_{80}$ veratridine+SVqq) were added 3 minutes later to activate the channel. Changes in fluorescence were measured at wavelengths of 440-480 nm and 565-625 nm over the course of the experimental run. Membrane depolarization was expressed as a ratio of the maximum $F_{440\text{-}480\ nm}/F_{565\text{-}625\ nm}$ reading above average baseline $F_{440\text{-}480\ nm}/F_{565\text{-}625\ nm}$ reading. IC$_{50}$ values were calculated from curve fits of the ratio data using a four-parameter logistic Hill equation (Accelrys Assay Explorer 3.3 Client, Accelrys, San Diego, Calif.) with percent inhibition plotted against compound concentration.

Data reported in Table 1.

Recombinant, Human Sodium Channel, Na$_v$1.8.

Two days prior to the experiment, frozen HEK293 cells stably expressing recombinant human Na$_v$1.8 (Essen, Ann Arbor, Mich.) were quickly thawed and plated at 22,500 cells/well in growth medium [MEM (Invitrogen #11095) with 10% FBS (Invitrogen #10082), 1 mM sodium pyruvate (Invitrogen, #C11360), 10 units/mL penicillin/10 U/mL streptomycin/29.2 μg/mL glutamine ((PSG 1%, Invitrogen #10378), 400 μg/mL zeocin (Invitrogen #R250) in black-walled, clear-bottom 384-well poly-D-lysine-coated assay plates (Greiner Bio-One, Frickenhausen, Germany) and incubated in a humidified 5% CO$_2$ incubator at 37° C. On the day of the assay, medium was removed by aspiration, and cells were washed with assay buffer [HBSS (Invitrogen, Carlsbad, Calif.) containing 20 mM HEPES (Invitrogen, Carlsbad, Calif.)]. After washing, 30 pt assay buffer containing the fluorescent voltage-sensor probe CC2-DMPE (Invitrogen, Carlsbad, Calif.) at 20 μM and 0.01% pluronic F-127 (Invitrogen, Carlsbad, Calif.) was added to the cells. Cells were incubated for 40 minutes at room temperature in the dark. Following the incubation, the cells were washed and 30 pt assay buffer containing 2.5 μM DiSBAC$_2$(3) substrate (Invitrogen, Carlsbad, Calif.) and 0.5 mM VABSC-1 (Invitrogen, Carlsbad, Calif.) was added to the cells. The cells were incubated for 60 minutes at room temperature in the dark. Fluorescence readings were made using a FLIPR®$^{TETRA}$ (Molecular Devices, Sunnyvale Calif.) equipped with voltage-sensor probe optics. The depolarizing agent, veratridine (Sigma-Aldrich, St. Louis, Mo.), was made up at 3× concentrations in assay buffer containing 1 mg/mL scorpion venom (SVqq, from Leiurus quinquestriatus; Sigma-Aldrich, St. Louis, Mo.). The assay agonist/opener concentration was determined each day using a 6-point veratridine concentration curve in duplicate, tested with three concentrations of tetracaine (0.1, 0.06, 0.01 μM all in 0.03% dimethyl sulfoxide) and 0.03% dimethyl sulfoxide control in assay buffer. The concentration of veratridine chosen for the assay, the "EC$_{80}$", was where the assay achieved maximum signal with the dimethyl sulfoxide control, minimal inhibition with 0.01 μM tetracaine, 50% inhibition with 0.06 μM tetracaine, and >50% inhibition with 0.1 μM tetracaine. Compounds were dissolved in dimethyl sulfoxide, and 8-point, 1:3 dilution concentration-response curves were prepared in duplicate in dimethyl sulfoxide, followed by preparation of 0.8 μL/well daughter plates of the dilutions. Test compounds in the daughter plate were diluted to (~3×) solutions in assay buffer immediately before assaying. Using the FLIPR®$^{TETRA}$, 20 μL of the (3×) compound solutions were first added to the cells, then 20 μL of depolarizing solution (3×EC$_{80}$ veratridine+SVqq) were added 3 minutes later to activate the channel. Changes in fluorescence were measured at wavelengths of 440-480 nm and 565-625 nm over the course of the experimental run. Membrane depolarization was expressed as a ratio of the maximum $F_{440\text{-}480\ nm}/F_{565\text{-}625\ nm}$ reading above average baseline $F_{440\text{-}480\ nm}/F_{565\text{-}625\ nm}$ reading. IC$_{50}$ values were calculated from curve fits of the ratio data using a four-parameter logistic Hill equation (Accelrys Assay Explorer 3.3 Client, Accelrys, San Diego, Calif.) with percent inhibition plotted against compound concentration.

Data reported in Table 1.

hERG QPatch Screening Protocol

Solutions and Compound Plates:

The bath solution contained (in mM): 140 NaCl, 5 KCl, 1 MgCl$_2$, 2 CaCl$_2$, 5 glucose, 20 HEPES, pH=7.4. The internal solution contained (in mM): 125 K-aspartate, 20 KCl, 10 EGTA, 5 MgATP, 1 MgCl$_2$, 5 HEPES, pH=7.3.

Compound plates were prepared with an acoustic liquid handler (Echo® 550, Labcyte), using 384-well source plates and 96-well destination plates. Compounds were delivered to the destination plates as 300 nL spots in half-log increments (1, 3, 10 and 30 mM), dissolved in dimethyl sulfoxide. Plates were solvated with bath solution (300 μL) to final concentrations (1, 3, 10 and 30 μM; 0.1% dimethyl sulfoxide) and added to the QPatch workstation.

Cells and Cell Preparation:

Human embryonic kidney (HEK-293) cells, stably transfected with the hERG channel, were obtained from Dr. C. W. January (Wisconsin Alumni Research Foundation). Cells were initially maintained at 37° C. (5% CO$_2$ atmosphere) in MEM supplemented media. Cells were cryo-preserved in 10% dimethyl sulfoxide, 90% fetal bovine serum at 10 M cells/mL. For electrophysiological studies, cells were thawed, resuspended in media at 1.0-1.5 M cells/mL and placed on the QPatch workstation.

QPatch Electrophysiology Workstation and Experimental Protocol:

Currents were recorded using QPatch HT (Sophion), an automated planar patch-clamp system. The QPatch uses forty-eight amplifiers and a 48-chamber QPlate positioned directly on top of the headstage. To obtain high resistant seals, cells are added to each chamber and allowed to settle for 10 seconds. Negative pressure is then applied to promote cell delivery to the patch chip openings on the chamber bottom. After formation of GΩ seals, negative pressure ramps are applied to obtain intracellular access. Access resistance was initially optimized by additional pressure ramps to assure the intracellular access was adequate for voltage clamp experiments (targeted access resistance <10 MΩ). Whole-cell compensation and series resistance compensation were used at 60% (both predicted and corrected). Experiments using QPatch were conducted at room temperature.

A single application of each concentration was applied to cells. During a five-minute wash-in period, a four-second depolarizing pulse to +20 mV, followed by a five-second repolarizing pulse to −50 mV was applied once every 15 seconds from a holding potential of −80 mV. Cells were exposed to four ascending concentrations of drug in half-log intervals.

Evaluation of hERG Current Block:

hERG tail current was measured as the difference in amplitude between a −50 mV pre-pulse and the end of a five-second test pulse to −50 mV, preceded by a four-second pulse to +20 mV. The hERG IC$_{50}$ values for compounds were determined from tail current analysis. The $IC_{50}$ was calculated with a logistic fitting routine using the following equation: $y=[(A_1-A_2)/(1+(x/IC_{50}))^p]A_2$, where $A_1$=initial× value, $A_2$=final×value and p=power.

Data reported in Table 1.

TABLE 1

FRET-Based membrane potential assays for human sodium channels, $Na_v1.7$ and $Na_v1.8$, and determination of hERG current block.

| Example | FRET-Membrane Potential Nav1.7 $IC_{50}$ (µM) | FRET-Membrane Potential Nav1.8 $IC_{50}$ (µM) | hERG QPatch Kv11.1 $IC_{50}$ (µM) |
|---|---|---|---|
| 1 | 1.88 | 2.79 | >30 |
| 2 | 2.09 | 2.38 | >30 |
| 3 | 1.93 | 5.4 | >30 |
| 4 | 1.95 | 2.86 | >30 |
| 5 | 1.68 | 2.64 | >30 |
| 6 | 13.09 | 14.67 | |
| 7 | 3.19 | 3.08 | >30 |
| 8 | 2.89 | | >30 |
| 9 | 0.578 | | 5.48 |
| 10 | 2.07 | | >30 |
| 11 | 3.95 | | >30 |
| 12 | 3.06 | | 13.7 |
| 13 | 11.05 | | |
| 14 | 1.95 | | >30 |
| 15 | 7.57 | | |
| 16 | 3.78 | | >30 |
| 17 | 8.93 | | |
| 18 | 7.64 | | |
| 19 | 3.48 | | >30 |
| 20 | 4.48 | | |
| 21 | 0.903 | | 14.2 |
| 22 | 6.72 | | |
| 23 | 2.93 | | >30 |
| 24 | 1.98 | 0.59 | 17 |
| 25 | 1.29 | | 4.31 |
| 26 | 2.94 | | >30 |
| 27 | 3.62 | | |
| 28 | 3.82 | | |
| 29 | 2.88 | | 26.5 |
| 30 | 3.62 | | |
| 31 | 0.463 | | 13.5 |
| 32 | 1.69 | | 7.43 |
| 33 | 13.35 | | |
| 34 | 9.91 | 8.36 | >30 |
| 35 | 3.85 | 5.34 | >30 |
| 36 | 11.45 | | |
| 37 | 11.53 | | |
| 38 | 6.4 | | |
| 39 | 14.64 | | |
| 40 | 10.44 | | |
| 41 | 13.06 | | |
| 42 | 8.89 | | |
| 43 | 3.03 | | >30 |
| 44 | >20 | >20 | |
| 45 | >20 | >20 | |
| 46 | 3.56 | | >30 |
| 47 | 3.06 | 17.2 | |
| 48 | 0.593 | 9.02 | |
| 49 | 0.397 | 4.03 | |

Osteoarthritic (OA) Pain Induced by Sodium Monoiodoacetate (MIA)

Pain behavior was assessed by measurement of hind limb grip force (GF) in adult osteoarthritic rats. Male Sprague Dawley rats, obtained from Charles River Laboratories, (Wilmington, Mass.), weighing 150-175 g, were injected in the unilateral knee join with a single intra-articular injection of sodium monoiodoacetate (MIA, 3 mg/rat). All rats were tested at 20 days following MIA injection. A behavioral measure of activity-induced pain was carried out. Measurements of the peak hind limb grip force were conducted by recording the maximum compressive force (CFmax), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at an approximately 2-3 minute interval to obtain a raw mean grip force (CFmax). This raw mean grip force data was in turn converted to a maximum hindlimb cumulative compressive force (CFmax), as the grams of force/kg of body weight, for each animal.

For evaluating the compound effects, the hind limb grip force was conducted 20 days following the intra-articular injection of MIA. A group of age-matched naïve (not injected with MIA) animals was added as a comparator to the drug-dosed groups. The vehicle control response for each group of MIA-treated animals was defined as the 0% response (0% effect), whereas the naïve control group was defined as the normal response and as 100% effect. The % effect for each dose group was expressed as % return of response to normalcy, compared to the naïve group. A percent maximal possible effect (% MPE) of testing compound was calculated according to the formula: (Treatment CFmax Vehicle CFmax)/Vehicle CFmax]×100). Higher % effect numbers indicate increased relief from the pain in the model, with 100% indicating a return to the level of response seen in normal (non-osteoarthritic) animals. All experiments evaluating drug effects in this model were conducted in a randomized blinded fashion.

The animals were housed in Association for Assessment and Accreditation of Laboratory Animal Care (AAALAC) approved facilities at AbbVie Inc. in a temperature-regulated environment under a controlled 12-hour light-dark cycle, with lights on at 6:00 a.m. Food and water were available ad libitum at all times except during testing. All testing was done following procedures outlined in protocols approved by AbbVie Inc.'s Institutional Animal Care and Use Committee.

Data reported in Table 2.

Rat Spinal Nerve Ligation (SNL) Model of Neuropathic Pain.

A model of spinal nerve ligation-induced (SNL model) neuropathic pain as originally described by Kim and Chung (Kim, S. H. and J. M. Chung, 1992, Pain 50, 355) was used to test a compound of the present application. The male Sprague Dawley rats (Charles River Laboratories, Wilmington, Mass.), weighing 150-175 g at the time of surgery, were placed under isoflurane anesthesia and a 1.5 cm incision was made dorsal to the lumbosacral plexus. The paraspinal muscles (left side) were separated from the spinous processes, the left L5 and L6 spinal nerves isolated, and tightly ligated with 5-0 silk suture distal to the dorsal root ganglion. Care was taken to avoid ligating the L4 spinal nerve. Following spinal nerve ligation, a minimum of 7 days of recovery and no more than 3 weeks was allowed prior to the behavioral testing (mechanical sensitivity). Only rats with threshold scores ≤4.5 g were considered allodynic and utilized in pharmacological experiments.

Mechanical sensitivity was measured using calibrated von Frey filaments (Stoelting, Wood Dale, Ill.). Paw withdrawal threshold (PWT) was determined by using the Dixon's up-down method (Dixon, W. J., 1980, Ann. Rev. Pharmacol. Toxicol., 20, 441). Rats were placed into inverted individual plastic containers (20×12.5×20 cm) on top of a suspended wire mesh with a 1 $cm^2$ grid to provide access to the ventral side of the hind paws, and acclimated to the test chambers for 20 minutes. The von Frey filaments were presented perpendicularly to the plantar surface of the selected hind paw, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, 1980). A percent maximal possible effect (% MPE) of testing compound was calculated according to the formula: (Log [compound–treated threshold]–Log [vehicle–treated threshold])/(Log [maximum threshold]–Log [vehicle-treated threshold])×100%, where the maximum threshold was equal to 15 g.

The animals were housed in Association for Assessment and Accreditation of Laboratory Animal Care (AAALAC) approved facilities at AbbVie Inc. in a temperature-regulated environment under a controlled 12-hour light-dark cycle, with lights on at 6:00 a.m. Food and water were available ad libitum at all times except during testing. All testing was done following procedures outlined in protocols approved by AbbVie Inc.s' Institutional Animal Care and Use Committee.

Data reported in Table 2.

TABLE 2

In vivo data for MIA-OA and SNL pain assays.

| Example | OA Dose (mg/kg) | OA MPE (%) | SNL Dose (mg/kg) | SNL MPE (%) |
|---|---|---|---|---|
| 1 | 30 | 70 | | |
| 2 | 30 | 62 | | |
| 10 | 10 | 74 | 100 | 59 |
| 11 | 10 | 56 | | |
| 24 | 10 | 66 | | |
| 32 | 10 | 9 | | |
| 34 | 30 | 85 | 100 | 60 |
| 35 | 30 | 99 | 100 | 40 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

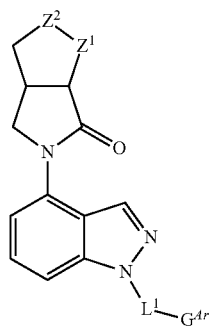

(I)

or a pharmaceutically acceptable salt or isotopically labelled form thereof, wherein:

one of $Z^1$ and $Z^2$ is $NR^1$ and the other of $Z^1$ and $Z^2$ is $CH_2$;

$R^1$ is selected from the group consisting of —$CH_2G^1$, —$CH_2G^2$, —C(O)-$G^1$, —C(O)-$G^2$, —C(O)—$R^2$, —C(O)N($R^a$)—$R^2$, —C(O)N($R^a$)($R^b$), —$SO_2$-$G^1$, —$SO_2$-$G^2$, —$SO_2$—$R^2$, —$SO_2$N($R^a$)—$R^2$, and —$SO_2$N($R^a$)($R^b$);

$R^2$ is selected from the group consisting of $C_1$-$C_6$-alkyl, $C_2$-$C_6$-alkenyl, $C_2$-$C_6$-alkynyl, —$(CR^{4a}R^{5a})_m$—$NO_2$, —$(CR^{4a}R^{5a})_m$—$OR^{1a}$, —$(CR^{4a}R^{5a})_m$—OC(O)$R^{1a}$, —$(CR^{4a}R^{5a})_m$—OC(O)N($R^b$)($R^{3a}$), —$(CR^{4a}R^{5a})_m$—$SR^{1a}$, —$(CR^{4a}R^{5a})_m$—S(O)$_2R^{2a}$, —$(CR^{4a}R^{5a})_m$—S(O)$_2$N($R^b$)($R^{3a}$), —$(CR^{4a}R^{5a})_m$—C(O)$R^{1a}$, —$(CR^{4a}R^{5a})_m$—C(O)O$R^{1a}$, —$(CR^{4a}R^{5a})_m$—C(O)N($R^b$)($R^{3a}$), —$(CR^{4a}R^{5a})_m$—N($R^b$)($R^{3a}$), —$(CR^{4a}R^{5a})_m$—N($R^a$)C(O)$R^{1a}$, —$(CR^{4a}R^{5a})_m$—N($R^a$)S(O)$_2R^{2a}$, —$(CR^{4a}R^{5a})_m$—N($R^a$)C(O)O($R^{1a}$), —$(CR^{4a}R^{5a})_m$—N($R^a$)C(O)N($R^b$)($R^{3a}$), —$(CR^{4a}R^{5a})_m$-$G^1$, —$(CR^{4a}R^{5a})_m$-$G^2$, cyano-$C_1$-$C_6$-alkyl, and halo-$C_1$-$C_6$-alkyl;

$R^a$ and $R^b$, at each occurrence, are each independently hydrogen, $C_1$-$C_6$-alkyl, or halo-$C_1$-$C_6$-alkyl;

$R^c$ at each occurrence, is independently hydrogen, $C_1$-$C_6$-alkyl, aryl, aryl-$C_1$-$C_6$-alkyl, cycloalkyl, cycloalkyl-$C_1$-$C_6$-alkyl, or halo-$C_1$-$C_6$-alkyl; wherein said aryl, the aryl of aryl-$C_1$-$C_6$-alkyl, the cycloalkyl, and the cycloalkyl of cycloalkyl-$C_1$-$C_6$-alkyl are independently unsubstituted or substituted with 1, 2 3, 4, or 5 substituents independently selected from the group consisting of $C_1$-$C_6$-alkyl, halo-$C_1$-$C_6$-alkyl, and halogen;

$R^d$ at each occurrence, is independently $C_1$-$C_6$-alkyl or halo-$C_1$-$C_6$-alkyl;

$R^{1a}$ and $R^{3a}$, at each occurrence, are each independently hydrogen, $C_1$-$C_6$-alkyl, -$G^1$, or —$(CR^{4a}R^{5a})_n$-$G^1$;

$R^{2a}$, at each occurrence, is independently $C_1$-$C_6$-alkyl, halo-$C_1$-$C_6$-alkyl, -$G^1$, or —$(CR^{4a}R^{5a})_n$-$G^1$;

$R^{4a}$ and $R^{5a}$, at each occurrence, are each independently hydrogen, halogen, $C_1$-$C_6$-alkyl, or halo-$C_1$-$C_6$-alkyl;

$G^{Ar}$ is phenyl or a 6-membered heteroaryl; wherein $G^{Ar}$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, and halogen;

$G^1$ is aryl or heteroaryl; wherein $G^1$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, —N($R^c$)$_2$, —N($R^c$)C(O)$R^c$, —O$R^c$, —C(O)$R^c$, —C(O)O$R^c$, —C(O)N($R^c$)$_2$, —$SO_2R^d$, —$SO_2$N($R^c$)$_2$, and —$CH_2G^3$;

$G^2$ is cycloalkyl, cycloalkenyl, or heterocycle; wherein $G^2$ is unsubstituted or substituted with 1, 2, 3, 4, or 5 substituents selected from the group consisting of $C_1$-$C_6$-alkyl, $C_2$-$C_6$-alkenyl, $C_2$-$C_6$-alkynyl, cyano, halo-$C_1$-$C_6$-alkyl, halogen, nitro, oxo, —N($R^c$)$_2$, —N($R^c$)C(O)$R^c$, —O$R^c$, —C(O)$R^c$, —C(O)O$R^c$, —C(O)N($R^c$)$_2$, —$SO_2R^d$, and —$SO_2$N($R^c$)$_2$;

$G^3$ is aryl, heteroaryl, heterocycle, cycloalkyl, or cycloalkenyl, wherein each $G^3$ is independently unsubstituted or substituted with 1, 2, 3, 4 or 5 substituents selected from the group consisting of $C_1$-$C_6$-alkyl, $C_2$-$C_6$-alkenyl, $C_2$-$C_6$-alkynyl, halogen, cyano, oxo, —$NO_2$, —OC(O)$R^{1a}$, —OC(O)N($R^b$)($R^{3a}$), —$SR^{1a}$, —S(O)$_2R^{2a}$, —S(O)$_2$N($R^b$)($R^{3a}$), —C(O)$R^{1a}$, —C(O)O$R^{1a}$, —C(O)N($R^b$)($R^{3a}$), —N($R^b$)($R^{3a}$), —N($R^a$)C(O)$R^{1a}$, —N($R^a$)S(O)$_2R^{2a}$, —N($R^a$)C(O)O($R^{1a}$), —N($R^a$)C(O)N($R^b$)($R^{3a}$), —$(CR^{4a}R^{5a})_m$—$NO_2$, —$(CR^{4a}R^{5a})_m$—$OR^{1a}$, —$(CR^{4a}R^{5a})_m$—OC(O)$R^{1a}$, —$(CR^{4a}R^{5a})_m$—OC(O)N($R^b$)($R^{3a}$), —$(CR^{4a}R^{5a})_m$—$SR^{1a}$, —$(CR^{4a}R^{5a})_m$—S(O)$_2R^{2a}$, —$(CR^{4a}R^{5a})_m$—S(O)$_2$N($R^b$)($R^{3a}$), —$(CR^{4a}R^{5a})_m$—C(O)$R^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)S(O)$_2$R$^{2a}$, —(CR$^{4a}$R$^{5a}$)$_m$N(R$^a$)C(O)O(R$^{1a}$), —(CR$^{4a}$R$^{5a}$)$_m$—N(R$^a$)C(O)N(R$^b$)(R$^{3a}$), cyano-C$_1$-C$_6$-alkyl, and halo-C$_1$-C$_6$-alkyl;

L$^1$ is a bond or —CH$_2$—; and m and n, at each occurrence, are each independently 1, 2, 3, 4, or 5.

2. The compound of claim 1, wherein
Z$^1$ is NR$^1$; and
Z$^2$ is CH$_2$.

3. The compound of claim 2, wherein, R$^1$ is selected from the group consisting of —CH$_2$G$^1$, —CH$_2$G$^2$, —SO$_2$-G$^1$, —SO$_2$-G$^2$, —SO$_2$—R$^2$, —SO$_2$N(R$^a$)—R$^2$, and —SO$_2$N(R$^a$)(R$^b$).

4. The compound of claim 2, wherein, R$^1$ is selected from the group consisting of —C(O)-G$^1$, —C(O)-G$^2$, —C(O)—R$^2$, —C(O)N(R$^a$)—R$^2$, and —C(O)N(R$^a$)(R$^b$).

5. The compound of claim 4, wherein,
R$^1$ is —C(O)-G$^2$;
G$^2$ is cycloalkyl or heterocycle; wherein G$^2$ is unsubstituted or substituted with 1, 2, 3, 4, or 5 substituents selected from the group consisting of C$_1$-C$_6$-alkyl, cyano, halo-C$_1$-C$_6$-alkyl, halogen, and —OR$^c$;
R$^c$ at each occurrence, is independently hydrogen or C$_1$-C$_6$-alkyl;
G$^{Ar}$ is phenyl; wherein G$^{Ar}$ is unsubstituted or substituted with 1, 2, or 3 substituents selected from the group consisting of C$_1$-C$_6$-alkyl, halo-C$_1$-C$_6$-alkyl, and halogen; and
L$^1$ is a bond.

6. The compound of claim 4, wherein,
R$^1$ is —C(O)—R$^2$; and
R$^2$ is selected from the group consisting of C$_1$-C$_6$-alkyl, C$_2$-C$_6$-alkenyl, C$_2$-C$_6$-alkynyl, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), and halo-C$_1$-C$_6$-alkyl.

7. The compound of claim 6, wherein,
R$^2$ is C$_1$-C$_6$-alkyl or —(CR$^{4a}$R$^{5a}$)$_m$—OR$^a$;
R$^{1a}$ is hydrogen or C$_1$-C$_6$-alkyl;
R$^{4a}$ and R$^{5a}$, at each occurrence, are each independently hydrogen, C$_1$-C$_6$-alkyl, or halo-C$_1$-C$_6$-alkyl;
G$^{Ar}$ is phenyl; wherein GA is unsubstituted or substituted with 1, 2, or 3 substituents selected from the group consisting of C$_1$-C$_6$-alkyl, halo-C$_1$-C$_6$-alkyl, and halogen;
L$^1$ is a bond; and
m at each occurrence is independently 1, 2, 3 or 4.

8. The compound of claim 1, wherein,
Z$^1$ is CH$_2$; and
Z$^2$ is NR.

9. The compound of claim 8, wherein,
R$^1$ is selected from the group consisting of —CH$_2$G$^1$ and —CH$_2$G$^2$.

10. The compound of claim 9, wherein,
R$^1$ is —CH$_2$G$^1$;
R$^c$ at each occurrence, is independently hydrogen or C$_1$-C$_6$-alkyl;
G$^1$ is aryl or heteroaryl; wherein G$^1$ is unsubstituted or substituted with 1, 2, 3, or 4 substituents selected from the group consisting of C$_1$-C$_6$-alkyl, halo-C$_1$-C$_6$-alkyl, halogen, and —OR$^c$;
G$^{Ar}$ is phenyl; wherein G$^{Ar}$ is unsubstituted or substituted with 1, 2, or 3 substituents selected from the group consisting of C$_1$-C$_6$-alkyl, halo-C$_1$-C$_6$-alkyl, and halogen; and
L$^1$ is a bond.

11. The compound of claim 8, wherein,
R$^1$ is selected from the group consisting of —C(O)-G$^1$, —C(O)-G$^2$, —C(O)—R$^2$, —C(O)N(R$^a$)—R$^2$, and —C(O)N(R$^a$)(R$^b$).

12. The compound of claim 11, wherein,
R$^1$ is selected from the group consisting of —C(O)-G$^1$, —C(O)-G$^2$, —C(O)—R$^2$, —C(O)N(R$^a$)—R$^2$, and —C(O)N(R$^a$)(R$^b$);
R$^2$ is selected from the group consisting of C$_1$-C$_6$-alkyl, —(CR$^{4a}$R$^{5a}$)$_m$—OR$^{1a}$, —(CR$^{4a}$R$^{5a}$)$_m$—C(O)R$^{1a}$, —(CR$^{4a}$R$^{5a}$)$_m$—C(O)N(R$^b$)(R$^{3a}$), —(CR$^{4a}$R$^{5a}$)$_m$—N(R$^a$)C(O)R$^{1a}$, —(CR$^{4a}$R$^{5a}$)$_m$-G$^1$, —(CR$^{4a}$R$^{5a}$)$_m$-G$^2$, and halo-C$_1$-C$_6$-alkyl;
R$^a$ and R$^b$, at each occurrence, are each independently hydrogen, C$_1$-C$_6$-alkyl, or halo-C$_1$-C$_6$-alkyl;
R$^c$ at each occurrence, is independently hydrogen or C$_1$-C$_6$-alkyl;
R$^{1a}$ and R$^{3a}$, at each occurrence, are each independently hydrogen, C$_1$-C$_6$-alkyl, or halo-C$_1$-C$_6$-alkyl;
R$^{4a}$ and R$^{5a}$, at each occurrence, are each independently hydrogen or C$_1$-C$_6$-alkyl, or halo-C$_1$-C$_6$-alkyl;
G$^1$ is aryl or heteroaryl; wherein G$^1$ is unsubstituted or substituted with 1, 2, 3, or 4 substituents selected from the group consisting of C$_1$-C$_6$-alkyl, halo-C$_1$-C$_6$-alkyl, halogen and —CH$_2$G$^3$;
G$^2$ is cycloalkyl or heterocycle; wherein G$^2$ is unsubstituted or substituted with 1, 2, 3, or 4 substituents selected from the group consisting of C$_1$-C$_6$-alkyl, halo-C$_1$-C$_6$-alkyl, halogen, and —OR$^c$;
G$^3$ is aryl, heteroaryl, heterocycle, or cycloalkyl, wherein each G$^3$ is independently unsubstituted or substituted with 1, 2, 3, 4 or 5 substituents selected from the group consisting of C$_1$-C$_6$-alkyl, halogen, —OR$^{1a}$, and halo-C$_1$-C$_6$-alkyl;
G$^{Ar}$ is phenyl; wherein G$^{Ar}$ is unsubstituted or substituted with 1, 2, or 3 substituents selected from the group consisting of C$_1$-C$_6$-alkyl, halo-C$_1$-C$_6$-alkyl, and halogen; and
L$^1$ is a bond; and
m, at each occurrence, is independently 1, 2, 3 or 4.

13. The compound of claim 8, wherein,
R$^1$ is selected from the group consisting of —SO$_2$-G$^1$, —SO$_2$-G$^2$, —SO$_2$—R$^2$, —SO$_2$N(R$^a$)—R$^2$, and —SO$_2$N(R$^a$)(R$^b$).

14. The compound of claim 13, wherein,
R$^1$ is selected from the group consisting of —SO$_2$-G$^1$, —SO$_2$-G$^2$ and —SO$_2$—R$^2$;
R$^2$ is selected from the group consisting of C$_1$-C$_6$-alkyl, —(CR$^{4a}$R$^{5a}$)$_m$—OR$^{1a}$, —(CR$^{4a}$R$^{5a}$)$_m$—C(O)R$^{1a}$, —(CR$^{4a}$R$^{5a}$)$_m$-G$^1$, —(CR$^{4a}$R$^{5a}$)$_m$-G$^2$, and halo-C$_1$-C$_6$-alkyl;
R$^c$ at each occurrence, is independently hydrogen or C$_1$-C$_6$-alkyl;
R$^{1a}$, at each occurrence, are each independently hydrogen, C$_1$-C$_6$-alkyl, or halo-C$_1$-C$_6$-alkyl;
R$^{4a}$ and R$^{5a}$, at each occurrence, are each independently hydrogen, C$_1$-C$_6$-alkyl, or halo-C$_1$-C$_6$-alkyl;
G$^1$ is aryl or heteroaryl; wherein G$^1$ is unsubstituted or substituted with 1, 2, 3, or 4 substituents selected from the group consisting of C$_1$-C$_6$-alkyl, halo-C$_1$-C$_6$-alkyl, and halogen;
G$^2$ is cycloalkyl or heterocycle; wherein G$^2$ is unsubstituted or substituted with 1, 2, 3, or 4 substituents selected from the group consisting of C$_1$-C$_6$-alkyl, halo-C$_1$-C$_6$-alkyl, halogen, —OR$^c$, —C(O)R$^c$, and —C(O)OR$^c$;

G$^{Ar}$ is phenyl; wherein G$^{Ar}$ is unsubstituted or substituted with 1, 2, or 3 substituents selected from the group consisting of C$_1$-C$_6$-alkyl, halo-C$_1$-C$_6$-alkyl, and halogen;

L$^1$ is a bond; and m, at each occurrence, is independently 1, 2, 3 or 4.

15. The compound of claim 1, selected from:

(3aS,6aS)-5-[1-(2-fluorophenyl)-1H-indazol-4-yl]-1-(3-hydroxy-3-methylbutanoyl)hexahydropyrrolo[3,4-b]pyrrol-6(1H)-one;

(3aR,6aR)-5-[1-(2-fluorophenyl)-1H-indazol-4-yl]-1-(3-hydroxy-3-methylbutanoyl)hexahydropyrrolo[3,4-b]pyrrol-6(1H)-one;

(3aR*,6aR*)-5-[1-(2-fluorophenyl)-1H-indazol-4-yl]-1-[(3R)-tetrahydrofuran-3-ylcarbonyl]hexahydropyrrolo[3,4-b]pyrrol-6(1H)-one;

rel-(3aR,6aR)-5-[1-(2-fluorophenyl)-1H-indazol-4-yl]-1-(2-hydroxy-2-methylpropanoyl)hexahydropyrrolo[3,4-b]pyrrol-6(1H)-one;

rel-(3aR,6aR)-5-[1-(2-fluorophenyl)-1H-indazol-4-yl]-1-[(1-hydroxycyclopropyl)carbonyl]hexahydropyrrolo[3,4-b]pyrrol-6(1H)-one;

rel-(3aR,6aR)-1-acetyl-5-[1-(2-fluorophenyl)-1H-indazol-4-yl]hexahydropyrrolo[3,4-b]pyrrol-6(1H)-one;

(3aR*,6aR*)-5-[1-(2-fluorophenyl)-1H-indazol-4-yl]-1-[(3R)-3-hydroxybutanoyl]hexahydropyrrolo[3,4-b]pyrrol-6(1H)-one;

rel-(3aR,6aR)-2-[1-(2-fluorophenyl)-1H-indazol-4-yl]-5-(3-methylbutanoyl)hexahydropyrrolo[3,4-c]pyrrol-1(2H)-one;

rel-(3aR,6aR)-5-benzyl-2-[1-(2-fluorophenyl)-1H-indazol-4-yl]hexahydropyrrolo[3,4-c]pyrrol-1(2H)-one;

rel-(3aR,6aR)-2-[1-(2-fluorophenyl)-1H-indazol-4-yl]-5-(tetrahydrofuran-2-ylacetyl)hexahydropyrrolo[3,4-c]pyrrol-1(2H)-one;

rel-(3aR,6aR)-2-[1-(2-fluorophenyl)-1H-indazol-4-yl]-5-(3-hydroxybutanoyl)hexahydropyrrolo[3,4-c]pyrrol-1(2H)-one;

rel-(3aR,6aR)-2-[1-(2-fluorophenyl)-1H-indazol-4-yl]-5-(1H-imidazol-1-ylcarbonyl)hexahydropyrrolo[3,4-c]pyrrol-1 (2H)-one;

rel-(3aR,6aR)-5-[1-(2-fluorophenyl)-1H-indazol-4-yl]-N-(1,3-oxazol-5-ylmethyl)-4-oxohexahydropyrrolo[3,4-c]pyrrole-2(1H)-carboxamide;

rel-(3aR,6aR)-2-[1-(2-fluorophenyl)-1H-indazol-4-yl]-5-[(5-methyl-1,2-oxazol-3-yl)carbonyl]hexahydropyrrolo[3,4-c]pyrrol-1 (2H)-one;

rel-(3aR,6aR)-5-[1-(2-fluorophenyl)-1H-indazol-4-yl]-N,N-dimethyl-4-oxohexahydropyrrolo[3,4-c]pyrrole-2(1H)-carboxamide;

rel-(3aR,6aR)-2-[1-(2-fluorophenyl)-1H-indazol-4-yl]-5-(1,3-oxazol-4-ylcarbonyl)hexahydropyrrolo[3,4-c]pyrrol-1(2H)-one;

rel-(3aR,6aR)-5-acetyl-2-[1-(2-fluorophenyl)-1H-indazol-4-yl]hexahydropyrrolo[3,4-c]pyrrol-1(2H)-one;

rel-(3aR,6aR)-2-[1-(2-fluorophenyl)-1H-indazol-4-yl]-5-(1,3-oxazol-2-ylmethyl)hexahydropyrrolo[3,4-c]pyrrol-1 (2H)-one;

rel-(3aR,6aR)-2-[1-(2-fluorophenyl)-1H-indazol-4-yl]-5-isobutyrylhexahydropyrrolo[3,4-c]pyrrol-1(2H)-one;

(3aR,6aS)-2-[1-(2-fluorophenyl)-1H-indazol-4-yl]-5-isobutyrylhexahydropyrrolo[3,4-c]pyrrol-1(2H)-one;

(3aS,6aS)-2-[1-(2-fluorophenyl)-1H-indazol-4-yl]-5-(isobutylsulfonyl)hexahydropyrrolo[3,4-c]pyrrol-1 (2H)-one;

(3aR,6aS)-2-[1-(2-fluorophenyl)-1H-indazol-4-yl]-5-[(2S)-tetrahydrofuran-2-ylacetyl]hexahydropyrrolo[3,4-c]pyrrol-1(2H)-one;

(3aS,6aS)-5-(ethyl sulfonyl)-2-[1-(2-fluorophenyl)-1H-indazol-4-yl]hexahydropyrrolo[3,4-c]pyrrol-1 (2H)-one;

(3aS,6aS)-2-[1-(2-fluorophenyl)-1H-indazol-4-yl]-5-(isopropylsulfonyl)hexahydropyrrolo[3,4-c]pyrrol-1 (2H)-one;

(3aR,6aS)-5-(1-benzofuran-3-ylacetyl)-2-[1-(2-fluorophenyl)-1H-indazol-4-yl]hexahydropyrrolo[3,4-c]pyrrol-1 (2H)-one;

(3aS,6aS)-2-[1-(2-fluorophenyl)-1H-indazol-4-yl]-5-[(3,3,3-trifluoropropyl)sulfonyl]hexahydropyrrolo[3,4-c]pyrrol-1 (2H)-one;

(3aS,6aS)-2-[1-(2-fluorophenyl)-1H-indazol-4-yl]-5-(pyridin-3-ylsulfonyl)hexahydropyrrolo[3,4-c]pyrrol-1 (2H)-one;

(3aS,6aS)-5-(cyclopropyl sulfonyl)-2-[1-(2-fluorophenyl)-1H-indazol-4-yl]hexahydropyrrolo[3,4-c]pyrrol-1 (2H)-one;

(3aS,6aS)-2-[1-(2-fluorophenyl)-1H-indazol-4-yl]-5-(phenylsulfonyl)hexahydropyrrolo[3,4-c]pyrrol-1 (2H)-one;

tert-butyl 4-{[(3aS,6aS)-5-[1-(2-fluorophenyl)-1H-indazol-4-yl]-4-oxohexahydropyrrolo[3,4-c]pyrrol-2(1H)-yl]sulfonyl}piperidine-1-carboxylate;

(3aR,6aS)-2-[1-(2-fluorophenyl)-1H-indazol-4-yl]-5-{[2-(pyrrolidin-1-ylmethyl)-1,3-oxazol-4-yl]carbonyl}hexahydropyrrolo[3,4-c]pyrrol-1 (2H)-one;

(3aR,6aS)-2-[1-(2-fluorophenyl)-1H-indazol-4-yl]-5-(tetrahydrofuran-3-ylcarbonyl)hexahydropyrrolo[3,4-c]pyrrol-1 (2H)-one;

(3aR,6aS)-5-[(3,5-dimethyl-1,2-oxazol-4-yl)acetyl]-2-[1-(2-fluorophenyl)-1H-indazol-4-yl]hexahydropyrrolo[3,4-c]pyrrol-1 (2H)-one;

(3aS,6aR)-2-[1-(2-fluorophenyl)-1H-indazol-4-yl]-5-[(3S)-3-hydroxybutanoyl]hexahydropyrrolo[3,4-c]pyrrol-1(2H)-one;

(3aR,6aS)-2-[1-(2-fluorophenyl)-1H-indazol-4-yl]-5-(3-hydroxy-3-methylbutanoyl)hexahydropyrrolo[3,4-c]pyrrol-1 (2H)-one;

(3aR,6aS)-2-[1-(2-fluorophenyl)-1H-indazol-4-yl]-5-[(3S)-3-hydroxybutanoyl]hexahydropyrrolo[3,4-c]pyrrol-1(2H)-one;

(3aR,6aS)-2-[1-(2-fluorophenyl)-1H-indazol-4-yl]-5-(3-hydroxy-3-methylbutanoyl)hexahydropyrrolo[3,4-c]pyrrol-1 (2H)-one;

(3aS,6aR)-2-[1-(2-fluorophenyl)-1H-indazol-4-yl]-5-[(3R)-3-hydroxybutanoyl]hexahydropyrrolo[3,4-c]pyrrol-1(2H)-one;

(3aR,6aS)-2-[1-(2-fluorophenyl)-1H-indazol-4-yl]-5-[(3R)-3-hydroxybutanoyl]hexahydropyrrolo[3,4-c]pyrrol-1(2H)-one;

(3aR,6aS)-5-[(2,2-difluorocyclopropyl)carbonyl]-2-[1-(2-fluorophenyl)-1H-indazol-4-yl]hexahydropyrrolo[3,4-c]pyrrol-1 (2H)-one;

(3aS,6aR)-2-[1-(2-fluorophenyl)-1H-indazol-4-yl]-5-(2-hydroxy-2-methylpropanoyl)hexahydropyrrolo[3,4-c]pyrrol-1(2H)-one;

(3aS,6aR)-2-[1-(2-fluorophenyl)-1H-indazol-4-yl]-5-[(1-hydroxycyclopropyl)carbonyl]hexahydropyrrolo[3,4-c]pyrrol-1(2H)-one;

(3aS,6aR)-5-[(3-chlorocyclobutyl)carbonyl]-2-[1-(2-fluorophenyl)-1H-indazol-4-yl]hexahydropyrrolo[3,4-c]pyrrol-1 (2H)-one;

3-[(3aR,6aS)-5-[1-(2-fluorophenyl)-1H-indazol-4-yl]-4-oxohexahydropyrrolo[3,4-c]pyrrol-2(1H)-yl]-3-oxopropanamide;

(3aS,6aR)-2-[1-(2-fluorophenyl)-1H-indazol-4-yl]-5-(3-hydroxypropanoyl)hexahydropyrrolo[3,4-c]pyrrol-1(2H)-one;

(3aS,6aR)-5-acetyl-2-[1-(2-fluorophenyl)-1H-indazol-4-yl]hexahydropyrrolo[3,4-c]pyrrol-1(2H)-one;

(3aR,6aR)-5-[1-(2-fluorophenyl)-1H-indazol-4-yl]-1-(2-hydroxy-2-methylpropanoyl)hexahydropyrrolo[3,4-b]pyrrol-6(1H)-one;

(3aR,6aR)-5-[1-(2-fluorophenyl)-1H-indazol-4-yl]-1-[(1-hydroxycyclopropyl)carbonyl]hexahydropyrrolo[3,4-b]pyrrol-6(1H)-one; and (3aS,6aS)-5-[1-(2-fluorophenyl)-1H-indazol-4-yl]-1-(2-hydroxy-2-methylpropanoyl)hexahydropyrrolo[3,4-b]pyrrol-6(1H)-one.

16. A pharmaceutical composition comprising a therapeutically effective amount of a compound of claim 1 in combination with a pharmaceutically acceptable carrier.

17. A method of selectively modulating the effects of pain in a mammal comprising administering an effective amount of a compound of claim 1.

18. A method of treating a condition or disorder modulated by the voltage-gated sodium channels $Na_v1.7$ and/or $Na_v1.8$ in a mammal comprising administering an effective amount of a compound of claim 1.

19. The method according to claim 18, wherein the condition or disorder is selected from the group consisting of pain, including osteoarthritis pain, joint pain (knee pain), neuropathic pain, post-surgical pain, low back pain, and diabetic neuropathy, pain during surgery, cancer pain, chemotherapy induced pain, headaches, including cluster headache, tension headache, migraine pain, trigeminal neuralgia, shingles pain, post-herpetic neuralgia, carpal tunnel syndrome, inflammatory pain, pain from rheumatoid arthritis, colitis, pain of interstitial cystitis, visceral pain, pain from kidney stone, pain from gallstone, angina, fibromyalgia, chronic pain syndrome, thalamic pain syndrome, pain from stroke, phantom limb pain, sunburn, radiculopathy, complex regional pain syndrome, HIV sensory neuropathy, central neuropathic pain syndromes, multiple sclerosis pain, Parkinson disease pain, spinal cord injury pain, menstrual pain, toothache, pain from bone metastasis, pain from endometriosis, pain from uterine fibroids, nociceptive pain, hyperalgesia, temporomandibular joint pain, inherited erythromelalgia (IEM), and paroxysmal extreme pain disorder (PEPD).

* * * * *